US011096624B2

(12) United States Patent
Mazlish et al.

(10) Patent No.: US 11,096,624 B2
(45) Date of Patent: Aug. 24, 2021

(54) ALARMS AND ALERTS FOR MEDICATION DELIVERY DEVICES AND SYSTEMS

(71) Applicant: Bigfoot Biomedical, Inc., Milpitas, CA (US)

(72) Inventors: Bryan Mazlish, Palo Alto, CA (US); Sabine Kabel-Eckes, Mountain View, CA (US); Shannon Sieber, Santa Clara, CA (US); Jeff Boissier, San Jose, CA (US); George Crothall, Oceanside, CA (US); Yean Wah Chan, Irvine, CA (US)

(73) Assignee: Bigfoot Biomedical, Inc., Milpitas, CA (US)

( * ) Notice: Subject to any disclaimer, the term of this patent is extended or adjusted under 35 U.S.C. 154(b) by 139 days.

(21) Appl. No.: 16/335,163

(22) PCT Filed: Dec. 12, 2017

(86) PCT No.: PCT/US2017/065894
§ 371 (c)(1),
(2) Date: Mar. 20, 2019

(87) PCT Pub. No.: WO2018/111928
PCT Pub. Date: Jun. 21, 2018

(65) Prior Publication Data
US 2019/0274624 A1 Sep. 12, 2019

Related U.S. Application Data

(60) Provisional application No. 62/433,124, filed on Dec. 12, 2016.

(51) Int. Cl.
*A61B 5/00* (2006.01)
*A61B 5/145* (2006.01)

(52) U.S. Cl.
CPC ............ *A61B 5/4839* (2013.01); *A61B 5/002* (2013.01); *A61B 5/14532* (2013.01); *A61B 5/746* (2013.01); *A61B 5/4848* (2013.01)

(58) Field of Classification Search
CPC ... A61B 5/002; A61B 5/0022; A61B 5/14532; A61B 5/4839; A61B 5/4848; A61B 5/6833; A61B 5/746
See application file for complete search history.

(56) References Cited

U.S. PATENT DOCUMENTS 2,605,765 A 8/1952 Kollsman
3,886,938 A 6/1975 Szabo et al.
(Continued)

FOREIGN PATENT DOCUMENTS

CA 2543545 A1 5/2005
DE 19627619 1/1998
(Continued)

OTHER PUBLICATIONS

Xilas Temp Touch, "The latest in high-tech and convenient devices," DOCNews, vol. 2, No. 7, Jul. 1, 2005, http://docnews.diabetesjournals.ordlcgi/contenl/foll/2/7i 13, 3 pages.
(Continued)

*Primary Examiner* — Deanna K Hall
(74) *Attorney, Agent, or Firm* — TraskBritt

(57) ABSTRACT

Systems, methods, and devices provide alarms and alerts in an on-body networked diabetes management system. Methods may include receiving glucose sensor data from a continuous glucose monitor and determining a dosage of insulin delivery based at least in part on the glucose sensor data. The method may include detecting an alarm or alert condition, and sending a wireless communication regarding the alarm or alert condition to a remote user-interface device. The method may include triggering an audible,
(Continued)

visual, or haptic alarm or alert on the insulin delivery device unless an acknowledgement of the alarm or alert condition is received within a predetermined period of time.

33 Claims, 23 Drawing Sheets

(56) References Cited

U.S. PATENT DOCUMENTS

| | | |
|---|---|---|
| 4,077,405 A | 3/1978 | Haerten et al. |
| 4,231,368 A | 11/1980 | Becker |
| 4,265,241 A | 5/1981 | Portner et al. |
| 4,300,554 A | 11/1981 | Hessberg et al. |
| 4,313,439 A | 2/1982 | Babb et al. |
| 4,398,908 A | 8/1983 | Siposs |
| 4,435,173 A | 3/1984 | Siposs et al. |
| 4,443,218 A | 4/1984 | DeCant et al. |
| 4,493,704 A | 1/1985 | Beard et al. |
| 4,529,401 A | 7/1985 | Leslie et al. |
| 4,681,569 A | 7/1987 | Coble et al. |
| 4,749,109 A | 6/1988 | Kamen |
| 4,838,857 A | 6/1989 | Strowe et al. |
| 4,850,817 A | 7/1989 | Nason et al. |
| 5,045,064 A | 9/1991 | Idriss |
| 5,088,981 A | 2/1992 | Howson et al. |
| 5,088,990 A | 2/1992 | Hivale et al. |
| D325,781 S | 4/1992 | Moller-Jensen |
| 5,190,522 A | 3/1993 | Wojcicki et al. |
| 5,225,763 A | 7/1993 | Krohn et al. |
| 5,250,027 A | 10/1993 | Lewis et al. |
| 5,261,882 A | 11/1993 | Sealfon |
| 5,314,412 A | 5/1994 | Rex |
| 5,335,994 A | 8/1994 | Weynant Nee Girones |
| 5,338,157 A | 8/1994 | Blomquist |
| 5,342,180 A | 8/1994 | Daoud |
| D351,469 S | 10/1994 | Okamoto |
| 5,389,078 A | 2/1995 | Zalesky et al. |
| 5,395,340 A | 3/1995 | Lee |
| 5,411,487 A | 5/1995 | Castagna |
| 5,545,143 A | 8/1996 | Fischell et al. |
| 5,551,850 A | 9/1996 | Williamson et al. |
| 5,554,123 A | 9/1996 | Herskowitz |
| 5,569,186 A | 10/1996 | Lord et al. |
| 5,626,566 A | 5/1997 | Petersen et al. |
| 5,637,095 A | 6/1997 | Nason et al. |
| 5,640,954 A | 6/1997 | Pfeiffer et al. |
| 5,665,065 A | 9/1997 | Colman et al. |
| 5,678,571 A | 10/1997 | Brown |
| 5,718,562 A | 2/1998 | Lawless et al. |
| D393,264 S | 4/1998 | Leung |
| 5,741,216 A | 4/1998 | Hemmingsen et al. |
| 5,766,155 A | 6/1998 | Hyman et al. |
| 5,772,635 A | 6/1998 | Dastur et al. |
| 5,816,306 A | 10/1998 | Giacomel |
| 5,852,803 A | 12/1998 | Ashby et al. |
| 5,858,001 A | 1/1999 | Tsals et al. |
| 5,918,603 A | 7/1999 | Brown |
| 5,919,167 A | 7/1999 | Mulhauser et al. |
| 5,925,018 A | 7/1999 | Ungerstedt |
| 5,928,201 A | 7/1999 | Poulsen et al. |
| 5,947,934 A | 9/1999 | Hansen et al. |
| 5,951,530 A | 9/1999 | Steengaard et al. |
| 5,957,889 A | 9/1999 | Poulsen et al. |
| 5,984,894 A | 11/1999 | Poulsen et al. |
| 5,984,897 A | 11/1999 | Petersen et al. |
| 5,997,475 A | 12/1999 | Bortz |
| 6,003,736 A | 12/1999 | Ljunggren |
| 6,010,485 A | 1/2000 | Buch-Rasmussen et al. |
| 6,032,119 A | 2/2000 | Brown et al. |
| 6,033,377 A | 3/2000 | Rasmussen et al. |
| 6,045,537 A | 4/2000 | Klitmose |
| D424,036 S | 5/2000 | Arora et al. |
| 6,056,728 A | 5/2000 | Von Schuckmann |
| 6,074,372 A | 6/2000 | Hansen |
| 6,110,149 A | 8/2000 | Klitgaard et al. |
| 6,156,014 A | 12/2000 | Petersen et al. |
| 6,171,276 B1 | 1/2001 | Lippe et al. |
| 6,231,540 B1 | 5/2001 | Smedegaard |
| 6,248,067 B1 | 6/2001 | Causey et al. |
| 6,248,090 B1 | 6/2001 | Jensen et al. |
| 6,248,093 B1 | 6/2001 | Moberg |
| 6,277,098 B1 | 8/2001 | Klitmose et al. |
| 6,302,855 B1 | 10/2001 | Lav et al. |
| 6,302,869 B1 | 10/2001 | Klitgaard |
| 6,354,996 B1 | 3/2002 | Drinan et al. |
| 6,368,314 B1 | 4/2002 | Kipfer et al. |
| 6,375,638 B2 | 4/2002 | Nason et al. |
| 6,379,339 B1 | 4/2002 | Klitgaard et al. |
| 6,381,496 B1 | 4/2002 | Meadows et al. |
| 6,404,098 B1 | 6/2002 | Kayama et al. |
| D460,053 S | 7/2002 | Choi |
| 6,427,088 B1 | 7/2002 | Bowman et al. |
| D461,241 S | 8/2002 | Moberg et al. |
| D461,891 S | 8/2002 | Moberg |
| 6,436,072 B1 | 8/2002 | Kullas et al. |
| 6,461,331 B1 | 10/2002 | Van Antwerp |
| 6,474,219 B2 | 11/2002 | Klitmose et al. |
| 6,485,461 B1 | 11/2002 | Mason et al. |
| 6,508,788 B2 | 1/2003 | Preuthun |
| 6,524,280 B2 | 2/2003 | Hansen et al. |
| 6,533,183 B2 | 3/2003 | Aasmul et al. |
| 6,537,251 B2 | 3/2003 | Klitmose |
| 6,540,672 B1 | 4/2003 | Simonsen et al. |
| 6,544,229 B1 | 4/2003 | Danby et al. |
| 6,547,764 B2 | 4/2003 | Larsen et al. |
| 6,551,276 B1 | 4/2003 | Mann et al. |
| 6,554,798 B1 | 4/2003 | Mann et al. |
| 6,554,800 B1 | 4/2003 | Nezhadian et al. |
| 6,558,320 B1 | 5/2003 | Causey et al. |
| 6,558,351 B1 | 5/2003 | Steil et al. |
| 6,562,001 B2 | 5/2003 | Lebel et al. |
| 6,562,011 B1 | 5/2003 | Buch-Rasmussen et al. |
| 6,564,105 B2 | 5/2003 | Starkweather et al. |
| 6,569,126 B1 | 5/2003 | Poulsen et al. |
| 6,571,128 B2 | 5/2003 | Lebel et al. |
| 6,577,899 B2 | 6/2003 | Lebel et al. |
| 6,582,404 B1 | 6/2003 | Klitgaard et al. |
| 6,585,644 B2 | 7/2003 | Lebel et al. |
| 6,585,699 B2 | 7/2003 | Ljunggreen et al. |
| 6,589,229 B1 | 7/2003 | Connelly et al. |
| 6,605,067 B1 | 8/2003 | Larsen |
| 6,613,019 B2 | 9/2003 | Munk |
| 6,641,533 B2 | 11/2003 | Causey et al. |
| 6,648,821 B2 | 11/2003 | Lebel et al. |
| 6,650,951 B1 | 11/2003 | Jones et al. |
| 6,656,158 B2 | 12/2003 | Mahoney et al. |
| 6,656,159 B2 | 12/2003 | Flaherty |
| 6,659,948 B2 | 12/2003 | Lebel et al. |
| 6,659,978 B1 | 12/2003 | Kasuga et al. |
| 6,659,980 B2 | 12/2003 | Moberg et al. |
| 6,663,602 B2 | 12/2003 | Moeller |
| 6,668,196 B1 | 12/2003 | Villegas et al. |
| 6,669,669 B2 | 12/2003 | Flaherty et al. |
| 6,687,546 B2 | 2/2004 | Lebel et al. |
| 6,690,192 B1 | 2/2004 | Wing |
| 6,691,043 B2 | 2/2004 | Ribeiro, Jr. |
| 6,692,457 B2 | 2/2004 | Flaherty |
| 6,692,472 B2 | 2/2004 | Hansen et al. |
| 6,694,191 B2 | 2/2004 | Starkweather et al. |
| 6,699,218 B2 | 3/2004 | Flaherty et al. |
| 6,702,779 B2 | 3/2004 | Connelly et al. |
| 6,715,516 B2 | 4/2004 | Ohms et al. |
| 6,716,198 B2 | 4/2004 | Larsen |
| 6,723,072 B2 | 4/2004 | Flaherty et al. |
| 6,733,446 B2 | 5/2004 | Lebel et al. |
| 6,736,796 B2 | 5/2004 | Shekalim |
| 6,740,059 B2 | 5/2004 | Flaherty |
| 6,740,072 B2 | 5/2004 | Starkweather et al. |
| 6,740,075 B2 | 5/2004 | Lebel et al. |
| 6,744,350 B2 | 6/2004 | Blomquist |
| 6,749,587 B2 | 6/2004 | Flaherty |
| 6,752,787 B1 | 6/2004 | Causey et al. |
| 6,758,810 B2 | 7/2004 | Lebel et al. |
| 6,768,425 B2 | 7/2004 | Flaherty et al. |

(56) References Cited

U.S. PATENT DOCUMENTS

| | | |
|---|---|---|
| 6,780,156 B2 | 8/2004 | Haueter et al. |
| 6,786,246 B2 | 9/2004 | Ohms et al. |
| 6,786,890 B2 | 9/2004 | Preuthun et al. |
| 6,796,970 B1 | 9/2004 | Klitmose et al. |
| 6,799,149 B2 | 9/2004 | Hartlaub |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman et al. |
| 6,813,519 B2 | 11/2004 | Lebel et al. |
| 6,827,702 B2 | 12/2004 | Lebel et al. |
| 6,830,558 B2 | 12/2004 | Flaherty et al. |
| 6,852,104 B2 | 2/2005 | Blomquist |
| 6,854,620 B2 | 2/2005 | Ramey |
| 6,854,653 B2 | 2/2005 | Eilersen |
| 6,855,129 B2 | 2/2005 | Jensen et al. |
| 6,872,200 B2 | 3/2005 | Mann et al. |
| 6,873,268 B2 | 3/2005 | Lebel et al. |
| 6,878,132 B2 | 4/2005 | Kipfer |
| 6,893,415 B2 | 5/2005 | Madsen et al. |
| 6,899,695 B2 | 5/2005 | Herrera |
| 6,899,699 B2 | 5/2005 | Enggaard |
| 6,922,590 B1 | 7/2005 | Whitehurst |
| 6,936,006 B2 | 8/2005 | Sabra |
| 6,936,029 B2 | 8/2005 | Mann et al. |
| 6,945,961 B2 | 9/2005 | Miller et al. |
| 6,948,918 B2 | 9/2005 | Hansen |
| 6,950,708 B2 | 9/2005 | Bowman et al. |
| 6,956,572 B2 | 10/2005 | Zaleski |
| 6,960,192 B1 | 11/2005 | Flaherty et al. |
| 6,979,326 B2 | 12/2005 | Mann et al. |
| 6,997,911 B2 | 2/2006 | Klitmose |
| 6,997,920 B2 | 2/2006 | Mann et al. |
| 7,005,078 B2 | 2/2006 | Van et al. |
| 7,008,399 B2 | 3/2006 | Larsen et al. |
| 7,014,625 B2 | 3/2006 | Bengtsson |
| 7,018,360 B2 | 3/2006 | Flaherty et al. |
| 7,025,743 B2 | 4/2006 | Mann et al. |
| 7,029,455 B2 | 4/2006 | Flaherty |
| 7,054,836 B2 | 5/2006 | Christensen et al. |
| 7,096,431 B2 | 8/2006 | Tambata et al. |
| 7,104,972 B2 | 9/2006 | Moller et al. |
| 7,109,878 B2 | 9/2006 | Mann et al. |
| 7,128,727 B2 | 10/2006 | Flaherty et al. |
| 7,133,329 B2 | 11/2006 | Skyggebjerg et al. |
| 7,232,423 B2 | 6/2007 | Mernoee |
| D545,837 S | 7/2007 | Haldimann et al. |
| 7,241,265 B2 | 7/2007 | Cummings et al. |
| D550,227 S | 9/2007 | Sato et al. |
| D553,625 S | 10/2007 | Burns et al. |
| D554,140 S | 10/2007 | Armendariz |
| 7,291,107 B2 | 11/2007 | Hellwig et al. |
| 7,343,197 B2 | 3/2008 | Shusterman |
| 7,454,359 B2 | 11/2008 | Rosenfeld et al. |
| 7,479,949 B2 | 1/2009 | Jobs et al. |
| D592,223 S | 5/2009 | Neuhaus |
| 7,534,226 B2 | 5/2009 | Mernoe et al. |
| 7,553,281 B2 | 6/2009 | Hellwig et al. |
| 7,555,727 B2 | 6/2009 | Hawkins et al. |
| 7,570,980 B2 | 8/2009 | Ginsberg |
| D600,341 S | 9/2009 | Loerwald |
| D603,421 S | 11/2009 | Ebeling et al. |
| D607,099 S | 12/2009 | Loerwald |
| 7,647,237 B2 | 1/2010 | Malave et al. |
| D614,587 S | 4/2010 | Yodfat et al. |
| 7,695,434 B2 | 4/2010 | Malecha |
| 7,708,717 B2 | 5/2010 | Estes et al. |
| 7,717,903 B2 | 5/2010 | Estes et al. |
| 7,751,907 B2 | 7/2010 | Blomquist |
| D623,753 S | 9/2010 | Saffer et al. |
| 7,789,859 B2 | 9/2010 | Estes et al. |
| 7,828,528 B2 | 11/2010 | Estes et al. |
| 7,837,647 B2 | 11/2010 | Estes et al. |
| 7,850,641 B2 | 12/2010 | Lebel et al. |
| 7,871,376 B2 | 1/2011 | Brown |
| D632,699 S | 2/2011 | Judy et al. |
| 7,878,975 B2 | 2/2011 | Liljeryd et al. |
| 7,887,512 B2 | 2/2011 | Estes et al. |
| 7,931,613 B2 | 4/2011 | Haueter et al. |
| 7,938,797 B2 | 5/2011 | Estes |
| D640,269 S | 6/2011 | Chen |
| 7,956,845 B2 | 6/2011 | Lee |
| D642,191 S | 7/2011 | Barnett et al. |
| 8,012,119 B2 | 9/2011 | Estes et al. |
| D648,804 S | 11/2011 | Coulter |
| D652,426 S | 1/2012 | Anzures |
| 8,132,101 B2 | 3/2012 | Buck et al. |
| D656,950 S | 4/2012 | Shallcross et al. |
| 8,156,070 B2 | 4/2012 | Buck et al. |
| D660,315 S | 5/2012 | Anzures |
| D661,701 S | 6/2012 | Brown et al. |
| 8,202,249 B2 | 6/2012 | Iio et al. |
| 8,217,946 B2 | 7/2012 | Halpern et al. |
| 8,219,222 B2 | 7/2012 | Blomquist |
| 8,221,345 B2 | 7/2012 | Blomquist |
| 8,221,359 B2 | 7/2012 | Kristensen et al. |
| 8,231,562 B2 | 7/2012 | Buck et al. |
| D665,409 S | 8/2012 | Gupta et al. |
| 8,237,715 B2 | 8/2012 | Buck et al. |
| 8,250,483 B2 | 8/2012 | Blomquist |
| 8,257,652 B2 | 9/2012 | Drucker et al. |
| 8,257,653 B2 | 9/2012 | Drucker et al. |
| 8,262,616 B2 | 9/2012 | Grant et al. |
| 8,273,296 B2 | 9/2012 | Drucker et al. |
| D669,165 S | 10/2012 | Estes et al. |
| D669,166 S | 10/2012 | Estes et al. |
| D669,167 S | 10/2012 | Estes et al. |
| 8,279,226 B2 | 10/2012 | Krieftewirth |
| 8,310,415 B2 | 11/2012 | McLaughlin et al. |
| 8,337,469 B2 | 12/2012 | Eberhart et al. |
| 8,357,091 B2 | 1/2013 | Say et al. |
| 8,365,065 B2 | 1/2013 | Gejdos et al. |
| 8,372,005 B2 | 2/2013 | Say et al. |
| D682,289 S | 5/2013 | Dijulio et al. |
| D682,304 S | 5/2013 | Mierau et al. |
| D682,305 S | 5/2013 | Mierau et al. |
| 8,439,834 B2 | 5/2013 | Schmelzeisen-Redeker et al. |
| D683,738 S | 6/2013 | Wujcik et al. |
| D687,062 S | 7/2013 | Gardner et al. |
| D687,541 S | 8/2013 | Estes et al. |
| 8,514,086 B2 | 8/2013 | Harper et al. |
| D689,087 S | 9/2013 | Fymat |
| D689,090 S | 9/2013 | Impas et al. |
| D689,523 S | 9/2013 | Galbraith et al. |
| D689,874 S | 9/2013 | Brinda et al. |
| 8,529,838 B2 | 9/2013 | Drucker et al. |
| 8,529,839 B2 | 9/2013 | Drucker et al. |
| 8,529,841 B2 | 9/2013 | Drucker et al. |
| D691,258 S | 10/2013 | Estes et al. |
| D691,259 S | 10/2013 | Estes et al. |
| D693,114 S | 11/2013 | Lemanski, Sr. |
| D693,365 S | 11/2013 | Gardner et al. |
| 8,579,815 B2 | 11/2013 | Galley et al. |
| 8,601,005 B2 | 12/2013 | Bousamra et al. |
| 8,615,366 B2 | 12/2013 | Galley et al. |
| D697,204 S | 1/2014 | Maier et al. |
| 8,622,906 B2 | 1/2014 | Say et al. |
| D698,808 S | 2/2014 | Funabashi et al. |
| D699,741 S | 2/2014 | Wantland et al. |
| 8,657,779 B2 | 2/2014 | Blomquist |
| D701,879 S | 4/2014 | Foit et al. |
| D702,258 S | 4/2014 | Wantland et al. |
| D705,261 S | 5/2014 | Holz et al. |
| 8,719,945 B2 | 5/2014 | Birtwhistle et al. |
| 8,756,074 B2 | 6/2014 | Brzustowicz |
| 8,761,940 B2 | 6/2014 | Long et al. |
| D709,080 S | 7/2014 | Kim |
| D709,183 S | 7/2014 | Kemlein |
| 8,774,887 B2 | 7/2014 | Say et al. |
| 8,816,862 B2 | 8/2014 | Harper et al. |
| 8,839,106 B2 | 9/2014 | Lee et al. |
| D714,816 S | 10/2014 | Varon |
| D715,835 S | 10/2014 | Montgomery et al. |
| D716,340 S | 10/2014 | Bresin et al. |

(56) References Cited

U.S. PATENT DOCUMENTS

| | | |
|---|---|---|
| D717,822 S | 11/2014 | Brotman et al. |
| D717,823 S | 11/2014 | Brotman et al. |
| D717,830 S | 11/2014 | Brinda et al. |
| D718,438 S | 11/2014 | Davis et al. |
| 8,895,315 B2 | 11/2014 | Batman et al. |
| D719,186 S | 12/2014 | Kim |
| 8,929,823 B2 | 1/2015 | Mears et al. |
| 8,961,465 B2 | 2/2015 | Blomquist |
| D724,616 S | 3/2015 | Jou |
| 8,992,464 B2 | 3/2015 | Bashan et al. |
| D727,336 S | 4/2015 | Allison et al. |
| 9,008,803 B2 | 4/2015 | Blomquist |
| 9,022,996 B2 | 5/2015 | Eberhart et al. |
| 9,033,877 B2 | 5/2015 | Werner et al. |
| 9,041,730 B2 | 5/2015 | Johnson et al. |
| D730,929 S | 6/2015 | Yu et al. |
| D733,175 S | 6/2015 | Bae |
| D733,179 S | 6/2015 | Kwon |
| 9,050,409 B2 | 6/2015 | Haueter et al. |
| 9,056,165 B2 | 6/2015 | Steil et al. |
| 9,072,477 B2 | 7/2015 | Say et al. |
| 9,076,107 B2 | 7/2015 | Cameron et al. |
| D736,792 S | 8/2015 | Brinda et al. |
| D737,278 S | 8/2015 | Shin et al. |
| D738,907 S | 9/2015 | Cabrera-Cordon et al. |
| D738,913 S | 9/2015 | Cabrera-Cordon et al. |
| D738,914 S | 9/2015 | Torres et al. |
| 9,134,823 B2 | 9/2015 | Grant et al. |
| 9,136,939 B2 | 9/2015 | Galley et al. |
| D741,891 S | 10/2015 | Gardner et al. |
| 9,159,148 B2 | 10/2015 | Boyer et al. |
| 9,171,343 B1 | 10/2015 | Fischell et al. |
| D743,435 S | 11/2015 | Herold et al. |
| 9,186,113 B2 | 11/2015 | Harper et al. |
| D744,505 S | 12/2015 | Wilberding et al. |
| D745,050 S | 12/2015 | Kwon |
| D745,543 S | 12/2015 | Kim et al. |
| D746,314 S | 12/2015 | Jung et al. |
| 9,198,623 B2 | 12/2015 | Fern et al. |
| D746,848 S | 1/2016 | Bovet et al. |
| D748,646 S | 2/2016 | Kim et al. |
| D749,097 S | 2/2016 | Zou et al. |
| D751,081 S | 3/2016 | Kim et al. |
| D751,090 S | 3/2016 | Hu et al. |
| D751,585 S | 3/2016 | Kaufthal et al. |
| D751,586 S | 3/2016 | Kaufthal et al. |
| D752,604 S | 3/2016 | Zhang |
| D752,736 S | 3/2016 | Chandrasenan et al. |
| D753,139 S | 4/2016 | Bovet |
| D753,177 S | 4/2016 | Mierau et al. |
| D753,685 S | 4/2016 | Zimmerman et al. |
| D754,670 S | 4/2016 | Park |
| D754,685 S | 4/2016 | Carlton et al. |
| D754,689 S | 4/2016 | Lee |
| D754,713 S | 4/2016 | Zhang et al. |
| D754,714 S | 4/2016 | Zhang et al. |
| D755,206 S | 5/2016 | Lee et al. |
| D755,830 S | 5/2016 | Chaudhri et al. |
| D757,026 S | 5/2016 | Lim et al. |
| D757,047 S | 5/2016 | Cornwell et al. |
| D758,433 S | 6/2016 | Lee et al. |
| D760,752 S | 7/2016 | Anzures et al. |
| D761,843 S | 7/2016 | Kim |
| D762,234 S | 7/2016 | Li et al. |
| D762,675 S | 8/2016 | Lim et al. |
| D763,285 S | 8/2016 | Chan et al. |
| D763,860 S | 8/2016 | Sunshine et al. |
| D763,921 S | 8/2016 | Dharwada et al. |
| D765,092 S | 8/2016 | Chaudhri et al. |
| D765,710 S | 9/2016 | Anzures et al. |
| D766,257 S | 9/2016 | Zhang et al. |
| D766,424 S | 9/2016 | Anderson et al. |
| D768,144 S | 10/2016 | Kim et al. |
| D768,687 S | 10/2016 | Bae et al. |
| D769,314 S | 10/2016 | Piroddi et al. |
| D769,322 S | 10/2016 | Rajeswaran et al. |
| D769,325 S | 10/2016 | Casalegno et al. |
| D771,672 S | 11/2016 | Tanabe et al. |
| D772,924 S | 11/2016 | Begin et al. |
| D773,510 S | 12/2016 | Foss et al. |
| D776,137 S | 1/2017 | Chaudhri et al. |
| D776,253 S | 1/2017 | Li |
| D776,702 S | 1/2017 | Huang et al. |
| D777,906 S | 1/2017 | Anderson et al. |
| D781,305 S | 3/2017 | Lau |
| D781,908 S | 3/2017 | Bhandari et al. |
| D783,652 S | 4/2017 | Guan et al. |
| D784,372 S | 4/2017 | Kovchiy |
| D786,266 S | 5/2017 | Van et al. |
| D786,270 S | 5/2017 | Barry et al. |
| D788,138 S | 5/2017 | Lee et al. |
| D788,140 S | 5/2017 | Hemsley et al. |
| D788,145 S | 5/2017 | Sullivan et al. |
| D788,808 S | 6/2017 | Chaudhri et al. |
| D789,419 S | 6/2017 | Chaudhri et al. |
| D790,562 S | 6/2017 | Nageli et al. |
| D790,583 S | 6/2017 | Kay et al. |
| D791,806 S | 7/2017 | Brewington et al. |
| 9,707,336 B2 | 7/2017 | Dang et al. |
| D794,649 S | 8/2017 | Niijima et al. |
| D795,284 S | 8/2017 | Miller et al. |
| D795,294 S | 8/2017 | Faulkner et al. |
| 9,717,849 B2 | 8/2017 | Mhatre et al. |
| D797,771 S | 9/2017 | Caporal et al. |
| D797,772 S | 9/2017 | Mizono et al. |
| D798,318 S | 9/2017 | Ferguson et al. |
| D798,895 S | 10/2017 | Kim et al. |
| D800,757 S | 10/2017 | Mullen et al. |
| D801,519 S | 10/2017 | Sabin et al. |
| D801,990 S | 11/2017 | Reissner et al. |
| D802,607 S | 11/2017 | Apodaca et al. |
| D803,850 S | 11/2017 | Chang et al. |
| D804,505 S | 12/2017 | Hoffman et al. |
| D805,541 S | 12/2017 | Juliano |
| D806,748 S | 1/2018 | Van et al. |
| D806,749 S | 1/2018 | Van et al. |
| D806,750 S | 1/2018 | Van et al. |
| D808,417 S | 1/2018 | Mander et al. |
| D808,974 S | 1/2018 | Chiappone et al. |
| D809,134 S | 1/2018 | Crothall |
| 9,878,097 B2 | 1/2018 | Estes |
| D810,095 S | 2/2018 | Vali et al. |
| D812,072 S | 3/2018 | Hoffman |
| D815,665 S | 4/2018 | Li et al. |
| D816,093 S | 4/2018 | Mazur et al. |
| 9,931,454 B2 | 4/2018 | Lo et al. |
| D816,708 S | 5/2018 | Riedel et al. |
| D816,709 S | 5/2018 | Riedel et al. |
| D816,713 S | 5/2018 | Kang |
| D819,065 S | 5/2018 | Xie et al. |
| D819,067 S | 5/2018 | Behzadi et al. |
| D819,646 S | 6/2018 | Jow et al. |
| D820,304 S | 6/2018 | Coffman et al. |
| D821,437 S | 6/2018 | Chaudhri et al. |
| D828,375 S | 9/2018 | Mok et al. |
| D828,377 S | 9/2018 | Dhide |
| D830,385 S | 10/2018 | Lepine et al. |
| D835,658 S | 12/2018 | Chan et al. |
| D835,659 S | 12/2018 | Anzures et al. |
| D837,809 S | 1/2019 | Kagatsume et al. |
| D839,294 S | 1/2019 | Mazlish et al. |
| 10,263,802 B2 | 4/2019 | Burns et al. |
| D852,837 S | 7/2019 | Mazlish et al. |
| D857,724 S | 8/2019 | Clediere et al. |
| D858,566 S | 9/2019 | Bacchus |
| D858,567 S | 9/2019 | Bacchus |
| D863,343 S | 10/2019 | Mazlish et al. |
| 10,426,896 B2 | 10/2019 | Desborough et al. |
| D870,767 S | 12/2019 | Villafane |
| D875,111 S | 2/2020 | Clediere |
| D875,124 S | 2/2020 | Yan |
| 10,572,107 B1 | 2/2020 | Beebe et al. |
| D883,319 S | 5/2020 | Caro et al. |
| D884,716 S | 5/2020 | Tan et al. |

(56) References Cited

U.S. PATENT DOCUMENTS

| | | |
|---|---|---|
| D886,850 S | 6/2020 | Kim et al. |
| D888,748 S | 6/2020 | Valladares et al. |
| D890,206 S | 7/2020 | Felkins et al. |
| 2001/0041869 A1 | 11/2001 | Causey et al. |
| 2001/0056262 A1 | 12/2001 | Cabiri et al. |
| 2002/0004651 A1 | 1/2002 | Ljunggreen et al. |
| 2002/0007154 A1 | 1/2002 | Hansen et al. |
| 2002/0040208 A1 | 4/2002 | Flaherty et al. |
| 2002/0091358 A1 | 7/2002 | Klitmose |
| 2002/0126036 A1 | 9/2002 | Flaherty et al. |
| 2002/0175931 A1 | 11/2002 | Holtz et al. |
| 2002/0177810 A1 | 11/2002 | Reilly et al. |
| 2003/0028089 A1 | 2/2003 | Galley et al. |
| 2003/0055380 A1 | 3/2003 | Flaherty |
| 2003/0065308 A1 | 4/2003 | Lebel et al. |
| 2003/0088238 A1 | 5/2003 | Poulsen et al. |
| 2003/0167035 A1 | 9/2003 | Flaherty et al. |
| 2003/0198558 A1 | 10/2003 | Nason et al. |
| 2003/0199825 A1 | 10/2003 | Flaherty |
| 2003/0216683 A1 | 11/2003 | Shekalim |
| 2004/0010207 A1 | 1/2004 | Flaherty et al. |
| 2004/0019325 A1 | 1/2004 | Shekalim |
| 2004/0064088 A1 | 4/2004 | Gorman et al. |
| 2004/0064096 A1 | 4/2004 | Flaherty et al. |
| 2004/0078028 A1 | 4/2004 | Flaherty et al. |
| 2004/0087894 A1 | 5/2004 | Flaherty |
| 2004/0092865 A1 | 5/2004 | Flaherty et al. |
| 2004/0092878 A1 | 5/2004 | Flaherty |
| 2004/0093331 A1 | 5/2004 | Garner et al. |
| 2004/0116866 A1 | 6/2004 | Gorman et al. |
| 2004/0127844 A1 | 7/2004 | Flaherty |
| 2004/0153032 A1 | 8/2004 | Garribotto et al. |
| 2004/0153257 A1 | 8/2004 | Munk |
| 2004/0171983 A1 | 9/2004 | Sparks et al. |
| 2004/0176727 A1 | 9/2004 | Shekalim |
| 2004/0204673 A1 | 10/2004 | Flaherty |
| 2004/0220551 A1 | 11/2004 | Flaherty et al. |
| 2004/0235446 A1 | 11/2004 | Flaherty et al. |
| 2004/0260233 A1 | 12/2004 | Garibotto et al. |
| 2005/0021005 A1 | 1/2005 | Flaherty et al. |
| 2005/0022274 A1 | 1/2005 | Campbell et al. |
| 2005/0038674 A1 | 2/2005 | Braig et al. |
| 2005/0044500 A1 | 2/2005 | Orimoto et al. |
| 2005/0065760 A1 | 3/2005 | Murtfeldt et al. |
| 2005/0090808 A1 | 4/2005 | Malave et al. |
| 2005/0090851 A1 | 4/2005 | Devlin |
| 2005/0095063 A1 | 5/2005 | Fathallah et al. |
| 2005/0114374 A1 | 5/2005 | Juszkiewicz et al. |
| 2005/0160858 A1 | 7/2005 | Mernoe |
| 2005/0171512 A1 | 8/2005 | Flaherty |
| 2005/0182366 A1 | 8/2005 | Vogt et al. |
| 2005/0192494 A1 | 9/2005 | Ginsberg |
| 2005/0192561 A1 | 9/2005 | Mernoe |
| 2005/0203461 A1 | 9/2005 | Flaherty et al. |
| 2005/0215982 A1 | 9/2005 | Malave et al. |
| 2005/0222645 A1 | 10/2005 | Malave et al. |
| 2005/0234404 A1 | 10/2005 | Vilks et al. |
| 2005/0238507 A1 | 10/2005 | Diianni et al. |
| 2005/0245878 A1 | 11/2005 | Mernoe et al. |
| 2005/0251097 A1 | 11/2005 | Mernoe |
| 2005/0267402 A1 | 12/2005 | Stewart et al. |
| 2005/0273059 A1 | 12/2005 | Mernoe et al. |
| 2006/0041229 A1 | 2/2006 | Garibotto et al. |
| 2006/0069382 A1 | 3/2006 | Pedersen |
| 2006/0074381 A1 | 4/2006 | Malave et al. |
| 2006/0095014 A1 | 5/2006 | Ethelfeld |
| 2006/0135913 A1 | 6/2006 | Ethelfeld |
| 2006/0142698 A1 | 6/2006 | Ethelfeld |
| 2006/0151545 A1 | 7/2006 | Imhof et al. |
| 2006/0178633 A1 | 8/2006 | Garibotto et al. |
| 2006/0184119 A1 | 8/2006 | Remde et al. |
| 2006/0200073 A1 | 9/2006 | Radmer et al. |
| 2006/0206054 A1 | 9/2006 | Shekalim |
| 2006/0247581 A1 | 11/2006 | Pedersen et al. |
| 2006/0276771 A1 | 12/2006 | Galley et al. |
| 2007/0073228 A1 | 3/2007 | Mernoe et al. |
| 2007/0073235 A1 | 3/2007 | Estes et al. |
| 2007/0073236 A1 | 3/2007 | Mernoe et al. |
| 2007/0088271 A1 | 4/2007 | Richards |
| 2007/0106218 A1 | 5/2007 | Yodfat et al. |
| 2007/0124002 A1 | 5/2007 | Estes et al. |
| 2007/0156092 A1 | 7/2007 | Estes et al. |
| 2007/0167905 A1 | 7/2007 | Estes et al. |
| 2007/0167912 A1 | 7/2007 | Causey et al. |
| 2007/0171087 A1 | 7/2007 | Shimazu et al. |
| 2007/0179444 A1 | 8/2007 | Causey et al. |
| 2007/0213657 A1 | 9/2007 | Jennewine et al. |
| 2007/0239116 A1 | 10/2007 | Follman et al. |
| 2008/0051716 A1 | 2/2008 | Stutz |
| 2008/0059158 A1 | 3/2008 | Matsuo et al. |
| 2008/0097381 A1 | 4/2008 | Moberg et al. |
| 2008/0119705 A1 | 5/2008 | Patel et al. |
| 2008/0172026 A1 | 7/2008 | Blomquist |
| 2008/0201325 A1 | 8/2008 | Doniger et al. |
| 2008/0208627 A1 | 8/2008 | Skyggebjerg |
| 2008/0220752 A1 | 9/2008 | Forstall et al. |
| 2008/0262469 A1 | 10/2008 | Brister et al. |
| 2008/0287755 A1 | 11/2008 | Sass et al. |
| 2008/0294094 A1 | 11/2008 | Mhatre et al. |
| 2008/0294108 A1 | 11/2008 | Briones et al. |
| 2008/0294109 A1 | 11/2008 | Estes et al. |
| 2008/0294142 A1 | 11/2008 | Patel et al. |
| 2008/0300534 A1 | 12/2008 | Blomquist |
| 2008/0306434 A1 | 12/2008 | Dobbles et al. |
| 2008/0319383 A1 | 12/2008 | Byland et al. |
| 2009/0054750 A1 | 2/2009 | Jennewine |
| 2009/0058823 A1 | 3/2009 | Kocienda |
| 2009/0067989 A1 | 3/2009 | Estes et al. |
| 2009/0069745 A1 | 3/2009 | Estes et al. |
| 2009/0069746 A1 | 3/2009 | Miller et al. |
| 2009/0069749 A1 | 3/2009 | Miller et al. |
| 2009/0069784 A1 | 3/2009 | Estes et al. |
| 2009/0069785 A1 | 3/2009 | Miller et al. |
| 2009/0069787 A1 | 3/2009 | Estes et al. |
| 2009/0089710 A1 | 4/2009 | Wood et al. |
| 2009/0099523 A1 | 4/2009 | Grant et al. |
| 2009/0156990 A1 | 6/2009 | Wenger et al. |
| 2009/0164239 A1 | 6/2009 | Hayter et al. |
| 2009/0197635 A1 | 8/2009 | Kim et al. |
| 2009/0204421 A1 | 8/2009 | Guimaraes |
| 2009/0253970 A1 | 10/2009 | Bashan et al. |
| 2009/0292247 A1 | 11/2009 | Basso et al. |
| 2010/0016700 A1 | 1/2010 | Sieh et al. |
| 2010/0048358 A1 | 2/2010 | Tchao et al. |
| 2010/0118037 A1 | 5/2010 | Sheikh et al. |
| 2010/0273610 A1 | 10/2010 | Johnson |
| 2010/0280329 A1 | 11/2010 | Pedersen et al. |
| 2010/0286601 A1 | 11/2010 | Yodfat et al. |
| 2010/0298765 A1 | 11/2010 | Budiman et al. |
| 2010/0305965 A1 | 12/2010 | Benjamin et al. |
| 2010/0315359 A1 | 12/2010 | Seong et al. |
| 2011/0009846 A1* | 1/2011 | Istoc ............. A61M 5/142 604/500 |
| 2011/0040247 A1 | 2/2011 | Mandro et al. |
| 2011/0092788 A1 | 4/2011 | Long et al. |
| 2011/0152657 A1 | 6/2011 | Bielawa et al. |
| 2011/0160555 A1 | 6/2011 | Reifman et al. |
| 2011/0201911 A1 | 8/2011 | Johnson et al. |
| 2011/0238520 A1 | 9/2011 | Selley |
| 2011/0273388 A1 | 11/2011 | Joo et al. |
| 2011/0313349 A1 | 12/2011 | Krulevitch et al. |
| 2011/0319322 A1 | 12/2011 | Bashan et al. |
| 2012/0022496 A1 | 1/2012 | Causey et al. |
| 2012/0053560 A1 | 3/2012 | Kawamura |
| 2012/0159328 A1 | 6/2012 | Millington et al. |
| 2012/0215201 A1 | 8/2012 | Brauker et al. |
| 2012/0232520 A1 | 9/2012 | Sloan et al. |
| 2012/0238999 A1 | 9/2012 | Estes et al. |
| 2012/0330270 A1 | 12/2012 | Colton |
| 2013/0165901 A1 | 6/2013 | Ruchti et al. |
| 2013/0172710 A1 | 7/2013 | Mears et al. |
| 2013/0184547 A1 | 7/2013 | Taub et al. |
| 2013/0245545 A1 | 9/2013 | Arnold et al. |
| 2013/0318439 A1 | 11/2013 | Landis et al. |

(56) References Cited

U.S. PATENT DOCUMENTS

| | | |
|---|---|---|
| 2013/0324941 A1* | 12/2013 | Mann .............. A61M 5/14244 604/246 |
| 2013/0331659 A1 | 12/2013 | Koski et al. |
| 2013/0338453 A1 | 12/2013 | Duke et al. |
| 2014/0012117 A1 | 1/2014 | Mensinger et al. |
| 2014/0025400 A1 | 1/2014 | Galley et al. |
| 2014/0039383 A1 | 2/2014 | Dobbles et al. |
| 2014/0058749 A1 | 2/2014 | Galley et al. |
| 2014/0068487 A1 | 3/2014 | Steiger et al. |
| 2014/0073892 A1 | 3/2014 | Randloev et al. |
| 2014/0154987 A1 | 6/2014 | Lee et al. |
| 2014/0160078 A1 | 6/2014 | Seo et al. |
| 2014/0309615 A1 | 10/2014 | Mazlish |
| 2014/0317546 A1 | 10/2014 | Jacobson et al. |
| 2014/0344280 A1 | 11/2014 | Wei et al. |
| 2014/0358082 A1 | 12/2014 | Ohzawa |
| 2014/0380218 A1 | 12/2014 | Johnnie |
| 2015/0025498 A1 | 1/2015 | Estes |
| 2015/0067527 A1 | 3/2015 | Gardner et al. |
| 2015/0073337 A1 | 3/2015 | Saint et al. |
| 2015/0073754 A1 | 3/2015 | Okkonen et al. |
| 2015/0080842 A1 | 3/2015 | Mathys |
| 2015/0112264 A1* | 4/2015 | Kamen .............. G16H 40/67 604/151 |
| 2015/0141912 A1 | 5/2015 | Estes |
| 2015/0173674 A1* | 6/2015 | Hayes .............. A61B 5/7278 600/301 |
| 2015/0277722 A1 | 10/2015 | Masterson et al. |
| 2016/0000998 A1 | 1/2016 | Estes |
| 2016/0038675 A1 | 2/2016 | Estes et al. |
| 2016/0058939 A1 | 3/2016 | Brewer et al. |
| 2016/0072841 A1 | 3/2016 | Caporal et al. |
| 2016/0089491 A1 | 3/2016 | Smith |
| 2016/0110064 A1 | 4/2016 | Shapira |
| 2016/0139671 A1 | 5/2016 | Jun et al. |
| 2016/0235913 A1 | 8/2016 | Smith et al. |
| 2016/0250422 A1 | 9/2016 | Koch et al. |
| 2016/0317743 A1 | 11/2016 | Estes |
| 2016/0357371 A1 | 12/2016 | Lee |
| 2016/0361494 A1 | 12/2016 | Jurg et al. |
| 2017/0003848 A1 | 1/2017 | Wakayanagi et al. |
| 2017/0017374 A1 | 1/2017 | Herz |
| 2017/0049957 A1 | 2/2017 | Michaud |
| 2017/0056591 A1 | 3/2017 | Breton et al. |
| 2017/0100538 A1 | 4/2017 | Mhatre et al. |
| 2017/0165416 A1 | 6/2017 | Saint |
| 2017/0173262 A1 | 6/2017 | Veltz |
| 2017/0176952 A1 | 6/2017 | Misaki et al. |
| 2017/0189614 A1 | 7/2017 | Mazlish et al. |
| 2017/0193184 A1 | 7/2017 | Hayter et al. |
| 2017/0199985 A1 | 7/2017 | Mazlish et al. |
| 2017/0203030 A1 | 7/2017 | Brewer et al. |
| 2017/0203036 A1 | 7/2017 | Mazlish et al. |
| 2017/0203037 A1 | 7/2017 | Desborough et al. |
| 2017/0203038 A1 | 7/2017 | Desborough et al. |
| 2017/0203039 A1 | 7/2017 | Desborough et al. |
| 2017/0216524 A1 | 8/2017 | Haider et al. |
| 2017/0224910 A1 | 8/2017 | Yodfat et al. |
| 2017/0232195 A1 | 8/2017 | Desborough et al. |
| 2017/0242975 A1 | 8/2017 | Kahlbaugh |
| 2017/0255771 A1 | 9/2017 | Miyakawa |
| 2017/0316592 A1 | 11/2017 | Kamath et al. |
| 2017/0332952 A1 | 11/2017 | Desborough et al. |
| 2017/0351842 A1 | 12/2017 | Booth et al. |
| 2018/0001006 A1 | 1/2018 | Schade et al. |
| 2018/0036495 A1 | 2/2018 | Searle et al. |
| 2018/0089395 A1 | 3/2018 | Desborough et al. |
| 2018/0101297 A1 | 4/2018 | Yang et al. |
| 2018/0133397 A1 | 5/2018 | Estes |
| 2018/0147362 A1 | 5/2018 | Arenas et al. |
| 2018/0150614 A1 | 5/2018 | Sokolovsim et al. |
| 2018/0161499 A1 | 6/2018 | Al-Ali et al. |
| 2018/0200435 A1 | 7/2018 | Mazlish et al. |
| 2018/0200436 A1 | 7/2018 | Mazlish et al. |
| 2018/0200437 A1 | 7/2018 | Mazlish et al. |
| 2018/0200438 A1 | 7/2018 | Mazlish et al. |
| 2018/0200439 A1 | 7/2018 | Mazlish et al. |
| 2018/0200441 A1 | 7/2018 | Desborough et al. |
| 2018/0207380 A1 | 7/2018 | Lantz et al. |
| 2018/0361060 A9 | 12/2018 | Rosinko |
| 2019/0001067 A1 | 1/2019 | Berey et al. |
| 2019/0015024 A1 | 1/2019 | Desborough et al. |
| 2019/0175841 A1 | 6/2019 | Sjolund et al. |
| 2019/0183434 A1 | 6/2019 | Sjolund et al. |
| 2019/0184111 A1 | 6/2019 | Sjolund et al. |
| 2019/0265871 A1 | 8/2019 | Eim et al. |
| 2019/0274624 A1 | 9/2019 | Mazlish et al. |
| 2019/0348166 A1 | 11/2019 | Booth et al. |
| 2020/0042166 A1 | 2/2020 | Burns |
| 2020/0097131 A1 | 3/2020 | Bowden |
| 2020/0201494 A1 | 6/2020 | Allington et al. |
| 2020/0236212 A1 | 7/2020 | Vinna et al. |

FOREIGN PATENT DOCUMENTS

| | | |
|---|---|---|
| DE | 10236669 A1 | 2/2004 |
| EM | 0006276170001 | 1/2007 |
| EM | 0006276170002 | 1/2007 |
| EM | 0006276170003 | 1/2007 |
| EM | 0007326490001 | 6/2007 |
| EM | 0007326490002 | 6/2007 |
| EM | 0031267050001 | 7/2016 |
| EM | 0031267050002 | 7/2016 |
| EM | 0031267050003 | 7/2016 |
| EM | 0031267050004 | 7/2016 |
| EP | 0062974 A1 | 10/1982 |
| EP | 0275213 A2 | 7/1988 |
| EP | 0496141 A1 | 7/1992 |
| EP | 0580723 A1 | 2/1994 |
| EP | 0612004 A1 | 8/1994 |
| EP | 0721358 A1 | 7/1996 |
| EP | 1045146 A2 | 10/2000 |
| EP | 1136698 A1 | 9/2001 |
| EP | 1177802 A1 | 2/2002 |
| EP | 1495775 A1 | 1/2005 |
| EP | 1527792 A1 | 5/2005 |
| EP | 1754498 A1 | 2/2007 |
| EP | 1818664 A1 | 8/2007 |
| EP | 2585252 A1 | 5/2013 |
| FR | 2585252 A1 | 1/1987 |
| GB | 0747701 | 4/1956 |
| GB | 2218831 A | 11/1989 |
| WO | 90/15928 A1 | 12/1990 |
| WO | 95/09021 A1 | 4/1995 |
| WO | 97/21457 A1 | 6/1997 |
| WO | 98/04301 A1 | 2/1998 |
| WO | 98/11927 A1 | 3/1998 |
| WO | 98/57683 A1 | 12/1998 |
| WO | 99/21596 A1 | 5/1999 |
| WO | 99/39118 A1 | 8/1999 |
| WO | 99/48546 A1 | 9/1999 |
| WO | 01/72360 A1 | 10/2001 |
| WO | 01/91822 A1 | 12/2001 |
| WO | 01/91833 A1 | 12/2001 |
| WO | 02/40083 A2 | 5/2002 |
| WO | 02/57627 A1 | 7/2002 |
| WO | 02/68015 A2 | 9/2002 |
| WO | 02/84336 A2 | 10/2002 |
| WO | 2002/100469 A2 | 12/2002 |
| WO | 03/26726 A1 | 4/2003 |
| WO | 2003/103763 A1 | 12/2003 |
| WO | 2004/056412 A2 | 7/2004 |
| WO | 2004/110526 A1 | 12/2004 |
| WO | 2005/002652 A2 | 1/2005 |
| WO | 2005/039673 A2 | 5/2005 |
| WO | 2005/072794 A2 | 8/2005 |
| WO | 2005/072795 A2 | 8/2005 |
| WO | 2006/067217 A2 | 6/2006 |
| WO | 2006/097453 A1 | 9/2006 |
| WO | 2006/105792 A1 | 10/2006 |
| WO | 2006/105793 A1 | 10/2006 |
| WO | 2006/105794 A1 | 10/2006 |

(56) References Cited

FOREIGN PATENT DOCUMENTS

| | | |
|---|---|---|
| WO | 2007/141786 A1 | 12/2007 |
| WO | 2011/163450 A1 | 12/2011 |
| WO | 2017/009724 | 1/2017 |

OTHER PUBLICATIONS

The Medtronic Diabetes Connection, 2006, 6 pages.
t:slimx2 Insulin Pump User Guide, Tandem Diabetes Care, Jul. 22, 2016.
Synchronise, IOS 7 Interface Symbol. By Flaticon. Freepik.com. Date: 2015. Retrieved from Internet: <https://www.freepik.com/free-icon/synchronise-ios-7-interface-symbol_751804.htm#term=arrows&page=69&position=14> (Year: 2015).
Smart et al., "Can children with type 1 diabetes and their caregivers estimate the carbohydrate content of meals and snacks?" Diabetic Medicine, 27, No. 3 (2010) pp. 38-353.
Sindaco et al., Use of the Short-acting Insulin Analogue Lispro in Intensive Treatment of Type 1 Diabetes Mellitus: Importance of Appropriate Replacement of Basal Insulin and Time-interval Injection-meal, Diabetic Medicine 1998, pp. 592-600. (Year: 1998).
Sara Krugman, Bionic Pancreas User Interface (3/4): Interface Details, Tidepool.org, Jul. 20, 2015.
Samuel Vozeh and Jean-Louis Steimer, Feedback Control Methods for Drug Dosage Optimisation, Concepts, Classification and Clinical Application, Clinical Pharmacokinelics, 10(6), pp. 457-476, Nov.-Dec. 1985.
Refreshing. By Flaticon. Freepik.com. Date: 2016. Retrieved from Internet: <https://www.freepik.com/free-icon/refreshing_807573.htm#term=arrows&page=26&position=26> (Year: 2016).
Refresh Arrow Loop. By Flaticon. Freepik.com. Date:2014. Retrieved from Internet: <https://www.freepik.com/free-icon/refresh-arrow-loop 705291 .htm#term=arrows&page=49&position=43> (Year: 2014).
Patent Abstracts of Japan, vol. 1999, No. 04, and JP 11 010036, Apr. 30, 1999 and Jan. 19, 1999, Toray Ind. Inc.
OmniPod Quick Start Guide, 2007, 2 pages.
OmniPod Insulin Management System-Investor Relations—Press Release, Feb. 1, 2005, http://investors.insulel.com/phoenix.zhlml?c=209336&p=irol-newsArticle&ID=988708&highlight= 1 page.
Michele Schiavon, Chiara Dalla Man, Yogish C. Kudva, Ananda Basu, and Claudio Cobelli, Quantitative Estimation of Insulin Sensitivity in Type 1 Diabetic Subjects Wearing a Sensor-Augmented Insulin Pump, Diabetes Care, vol. 37, pp. 1216-1223, May 2014.
Medtronic News Release, "Medtronic Receives FDA Approval for World's First Insulin Pump with Real-time Continuous Glucose Monitoring," Apr. 13, 2006, 3 pages.
Kuwayama, Yasaburo. Trademarks & Symbols. vol. 2: Symbolical Designs. Van Nostrand Reinhold Company. Date published: 1973. p. 136. (Year: 1973).
JDRF, Statistics: JDRF and Diabetes, http://jdrf.org/aboul-jdr/facl-sheels/jdrf-anddiabeles-statistics/, 2014.
International Written Opinion for International Application No. PCT/US17/065894, dated Mar 7, 2018, 7 pages.
International Search Report for International Application No. PCT/US17/065894, dated Mar 7, 2018, 2 pages.
Hurley, Dan. Artificial Pancreas Makers Race to Markel. Discover. Date published: Apr. 12, 2016. <http://discovermagazine.com/2016/may/13-priming-the-pump>.
Hoskins, Mike, News: Bigfoot Closed Loop, Jul. 17, 2017, Healthline.com [online], [visited Jan. 22, 2019]. Internet: https://web.archive.org/web/20170810052840/https://www.diabetesdaily.com/blog/bigfoot-biomedical-aims-to-take-multiple-daily-injections-to-the-next-level-with-timesulin-acquisition (Year: 2017).
Guy A. Dumont, Feedback Control for Clinicians, Springer Science+Media, Apr. 12, 2013, New York.
Fischer et al., In Vivo Comparison of Different Algorithms for the Artificial Beta-Cell, Artificial Organs, 9(2), International Society for Artificial Organs, May 1985, New York.
E. Salzsieder, G. Albrecht, E. Jutzi, and U. Fischer, Estimation of Individually Adapted Control Parameten for an Artificial Beta Cell, Biomedica Biochimica Acta. 43(5) pp. 585-96, May 1984.
Dreyfuss, Henry. Symbol Sourcebook. Van Nostrand Reinhold Company. Date published: 1984. p. 28. (Year: 1984).
Delaney, Chelsey, "4 apps for tracking your fertility" Jun. 6, 2016, Bedsider, site visited Oct. 19, 2018: https://www.bedsider.org/features/647-4-apps-for-tracking-your-fertility.
Debiotech News Release, "Debiotech reveals its new miniaturized Disposable Insulin Nanopump™ for Diabetes therapy," available at http://www.debiotech.com/news/nw 159.html Apr. 24, 2006, 3 pages.
David A. Copp, Ravi Gondhalekar, and Joao P. Hespanha, Simultaneous Model Predictive Control and Moving Horizon Estimation for Blood Glucose Regulation in Type 1 Diabetes, Optimal Control Applications and Methods, Wiley InterScience, DOI: 10.1002/oca, pp. 1-15, Oct. 2016.
Dassau and Associates, 12-Week 24/7 Ambulatory Artificial Pancreas With Weekly Adaptation of Insulin Delivery Settings: Effect on Hemoglobin A1C and Hypoglycemia, Diabetes Care, Oct. 13, 2017.
Curved Arrow to the Right. By Flaticon. Freepik.com. Date: 2015. Retrieved from Internet: <https://www.freepik.com/free-icon/curved-arrow-to-the-right 735735.htm#term=arrows&page=59&position=69> (Year: 2015).
Collins and Lee, "Microfluidic flow transducer based on the measurement of electrical admittance," Lab Chip, 2004,4:7-10.
Centers for Disease Control and Prevention, Number (in Millions) of Adults with Diabetes by Diabetes Medication Status, United States, 1997-2011, http://www.cdc.gov/diabetes/statistics/meduse/fig1.him, 2013.
Bigfoot Biomedical Reveals its Automated Insulin Delivery System. diaTribe. Date published: Jan. 25, 2016 <https://diatribe.org/bigfoot-biomedical-reveals-its-automated-insulin-delivery-system>.
Bhalla, Raveesh, Understanding Material Design Part II, Sep 28, 2014, Medium.com [online], [site visited Apr. 11, 2018], Available from Internet: https://medium.eom/@raveeshbhalla/understanding-material-design-cf2d60a16de3 (Year: 2014).
Baruah, Insulin Pens: The Modern Delivery Devices, Google Scholar 2011, pp. 38-40. (Year: 2011).
Arrows, Couple, IOS 7 Interface Symbol. By Flaticon. Freepik.com. Date: 2015. Retrieved from Internet: <https://www.freepik.com/free-icon/arrows-couple-ios-7-interface-symbo_751266.htm#term=arrows&page=68&position=43> (Year: 2015).
Arrows Curves Forming an Oval Shape. By Flaticon. Freepik.com. Date: 2015. Retrieved from Internet: <https://www.freepik.com/free-icon/arrows-curves-forming-an-oval-shape_746143.htm> (Year: 2015).
Arrow Repeat. By Flaticon. Freepik.com. Date: 2014. Retrieved from Internet: <https://www.freepik.com/free-icon/arrow-repeat_694329.htm#term=arrows&page=47&position=67> (Year: 2014).
Accu-Chek Spirit, "Pump Therapy Made for You," Roche, 2006, 6 pages.
"Omnipod Horizon: Automated Glucose Control" Jun. 2017, 2 pages.
"Clean Toggle Button Navigation Menu PSD" Jan. 24, 2014, WeLoveSoLo, site visited Oct. 19, 2018: https://www.welovesolo.com/clean-toggle-button-navigation-menu-psd/.
Eren-Oruklu et al., Adaptive Control Strategy for Regulation of Blood Glucose Levels in Patients with Type 1 Diabetes, ScienceDirect2009, pp. 1333-1346. (Year: 2009).
Owens et al., Run-to-Run Control of Blood Glucose Concentrations for People with Type 1 Diabetes Mellitus, IEEE 2006, pp. 996-1005. (Year: 2006).
"Medical Set." iconfinder.com. Added Apr. 7, 2017. Accessed Jan. 27, 2020. Available online at URL: https://www.iconfinder.com/iconsets/medical-set-5 (Year: 2017).
"Three icons—Ready, Set and Go" Nov. 29, 2015, depositphotos, site visited Apr. 21, 2020: https://depositphotos.com/91436542/stock-illustration-countdown-ready-set-go-colorful.html (Year: 2015).
Ansyari, Nazurrudin. "Circle Badge Set." iconfinder.com. Added Aug. 15, 2016. Accessed Jan. 27, 2020. Available online at URL: https://www.iconfinder.com/iconsets/circle-badge-set (Year: 2016).

(56) References Cited

OTHER PUBLICATIONS

Bode et al., Diabetes Management in the New Millennium Using Insulin Pump Therapy, Wiley Inter Science 2002, pp. 514-520. (Year: 2002).

Dreyfus, Henry. Symbol Source Book. New York, McGraw-Hill, 1972. pp. 52, 180, and 184. (Year: 1972).

European search report dated Dec. 5, 2019 for EP Application No. 17882173.

Grill et al., Exercise and Postprandial Lipid Metabolism: an Update on Potential Mechanisms and Interactions with High-Carbohydrate Diets/(Review), Elsevier 2003, pp. 122-132. (Year: 2003).

Harvey et al., Quest for the Artificial Pancreas, IEEE 2010, pp. 53-62. (Year: 2010).

Karnes, Chris. "Kids Mental Health App." dribbble.com. Feb. 1, 2020. Accessed May 7, 2020. Available online at URL: https://dribbble.com/shots/9841070-Kids-Mental-Health-App (Year: 2020).

Kumar, Rohit. "Health App." dribbble.com. May 14, 2015. Accessed May 7, 2020. Available online at URL: https://dribbble.com/shots/2062723-Health-App (Year: 2015).

Pearson, Practical Aspect of Insulin Pen Devices, Journal of Diabetes Science and Technology 2010, pp. 522-531. (Year: 2010).

Shishir, Shahidl Islam. "Med-i App | Splash Home and Logo." dribbble.com. Jul. 28, 2019. Accessed May 7, 2020. Available online at URL: https://dribbble.com/shots/6852974-Med-i-App-I-Splash-Home-and-Logo (Year: 2019).

Simmons, Cory, "How to Make Your Own Button UI Kil with Super-Clean Syntax" Dec. 23, 2014, envato tuts+, site visited Sep. 19, 2019: https://webdesign.lutsplus.com/lutorials/how-lo-make-your-0wn-button-ui-kil-wilh-super-clean-syntax-cms-22946.

Zhang et al., Second Insulin Pump Safety Meeting: Summary Report, Journal of Diabetes Science and Technology 2010, pp. 488-493. (Year: 2010).

\* cited by examiner

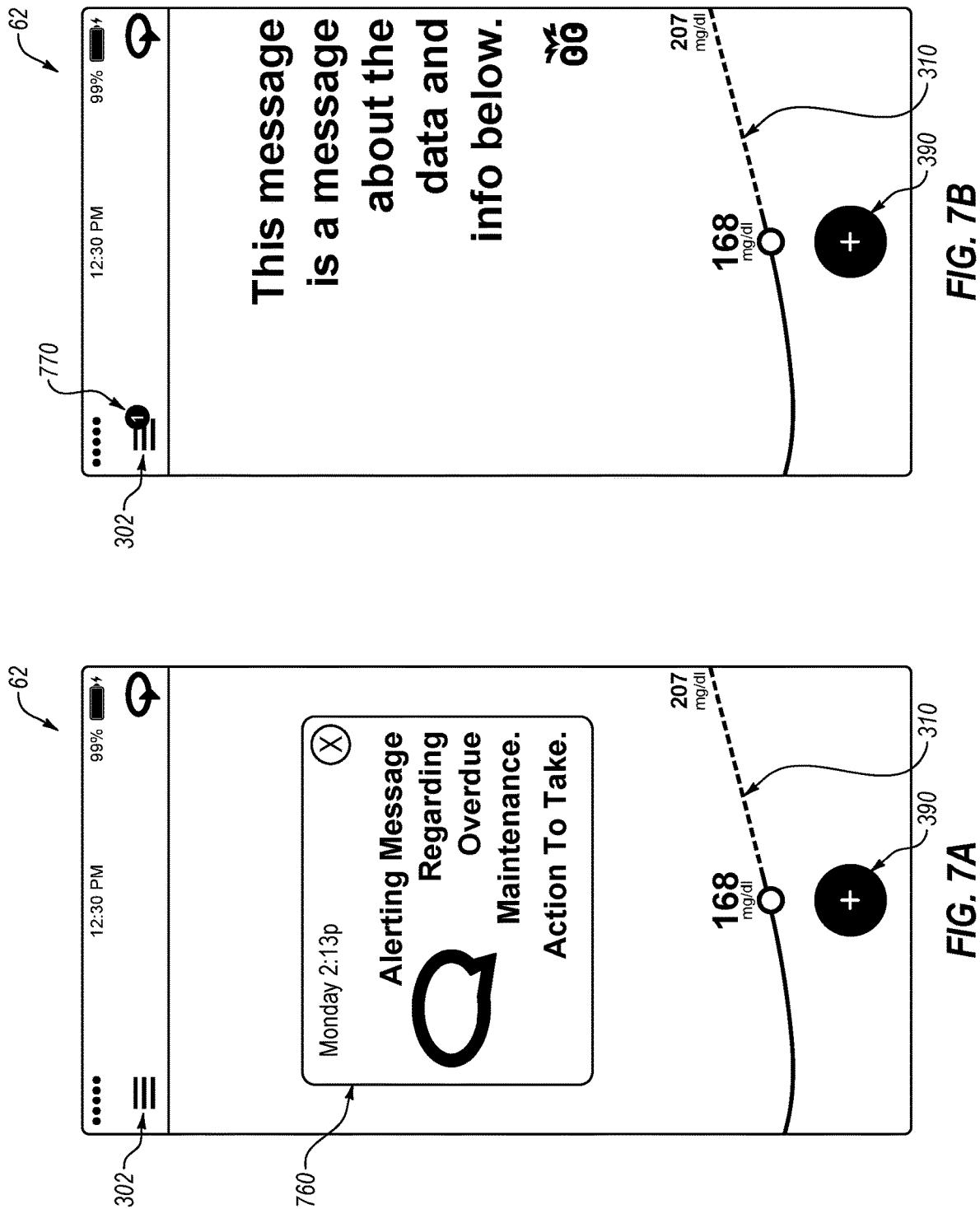

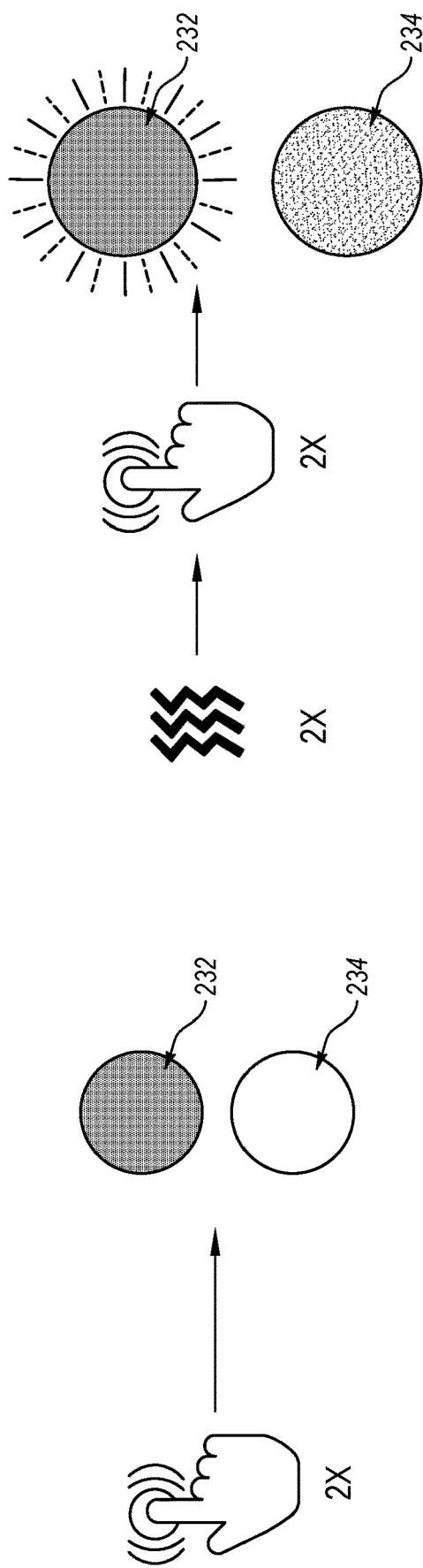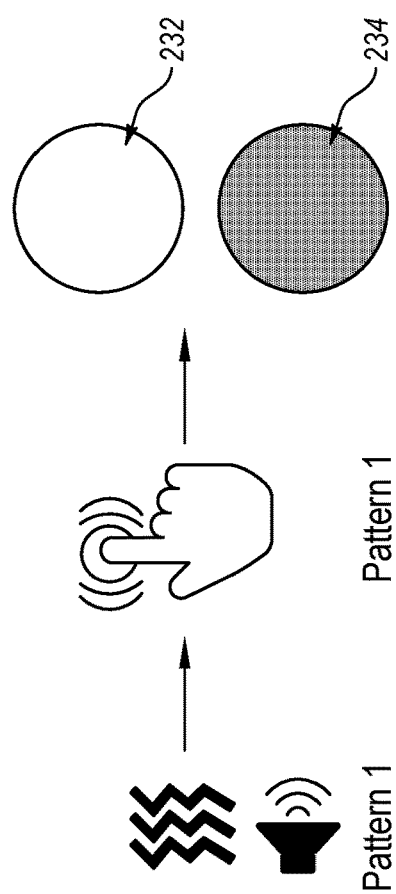
FIG. 15A
FIG. 15B
FIG. 15C

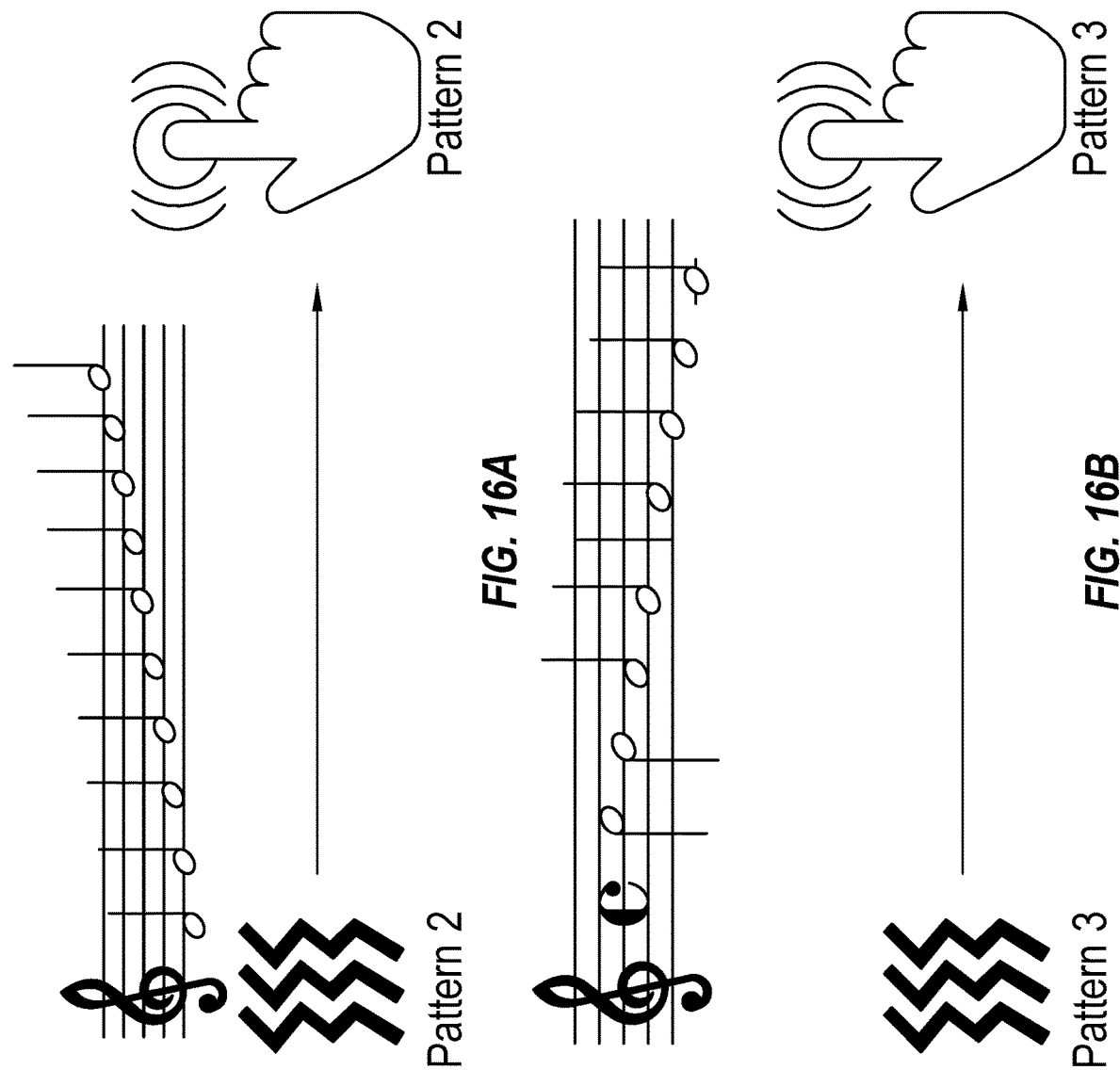

ALARMS AND ALERTS FOR MEDICATION DELIVERY DEVICES AND SYSTEMS

CROSS-REFERENCE TO RELATED APPLICATIONS

This application is a national phase entry under 35 U.S.C. § 371 of International Patent Application PCT/US2017/065894, filed Dec. 12, 2017, designating the United States of America and published in English as International Patent Publication WO2018/111927 A1 on Jun. 21, 2018, which claims the benefit under Article 8 of the Patent Cooperation Treaty to U.S. Provisional Patent Application Ser. No. 62/433,124, filed Dec. 12, 2016, the disclosure of each of which is hereby incorporated herein in its entirety by this reference.

TECHNICAL FIELD

This disclosure relates to alarms and alerts for medication delivery devices and systems, particularly for medication delivery systems that have a medication delivery device that communicates with a primary user-interface for the medication delivery device and related systems and methods.

BACKGROUND

People with Type I, Type II, or gestational diabetes must track their blood glucose levels and sometimes treat their condition to maintain appropriate blood glucose levels. Control of diabetes can include the monitoring of blood glucose levels using a blood glucose monitor (BGM) and sometimes a continuous glucose monitor (CGM). People with Type I, and some people with Type II or gestational diabetes, require insulin or an analog thereof. Because it cannot be taken orally, insulin is injected with a syringe or delivered subcutaneously by an external infusion pump. Excessive insulin delivery, however, can result in acute hypoglycemia, which can result in severe bodily injury and/or death. The failure to administer an appropriate amount of insulin to a person with diabetes, however, results in hyperglycemia, which can result in severe bodily injury and/or death. Because of the grave risks associated with diabetes, CGMs and insulin infusion pump systems typically provide a series of alarms and alerts that draw attention to the user's current glycemic condition, system conditions, and/or other potential issues, but these alarms and alerts can result in alert fatigue. Users having alert fatigue may start to ignore alarms or alerts or discontinue use of a CGM or insulin infusion pump, thus reducing the quality of their treatment. Moreover, users may wish to keep their external infusion pump or CGM concealed from view in order to avoid unwanted attention. Accordingly, there is a need for an improved system for providing diabetes-related information, alerts, and alarms.

DISCLOSURE

Medication delivery systems, methods, and devices provided herein include at least a medication delivery device (e.g., an insulin delivery device) and a remote user-interface device (e.g., a smartphone having an installed app) in communication (e.g., wireless communication) with each other. In some cases, the remote user-interface device can serve as the primary user interface for interacting with the medication delivery device, but the medication delivery device can be adapted to provide audible, visual, or haptic feedback under certain conditions. In some cases, methods, devices, and systems provided herein can have a controller in the medication delivery device detect an alarm or alert condition and send a wireless communication intended for a remote user-interface device prior to issuing an alarm or alert on the medication delivery device. In some cases, methods, devices, and systems provided herein can include a controller in the medication delivery device adapted to receive and a remote user-interface device adapted to send a wireless communication indicating that a user has acknowledged an alarm or alert condition. In some cases, methods, devices, and systems provided herein can include a controller in the medication delivery device adapted to cause the medication delivery device to provide an audible, visual, and/or haptic alarm or alert if the controller does not receive a user acknowledgement within a predetermined period of time after sending the wireless communication, which can ensure that the user is able to receive communications from the remote user-interface device. For example, in some cases, a remote user-interface device can be programmed by the user to not provide audible alarms, or the remote user-interface device may be too far away from the medication delivery device or may have a depleted battery. In some cases, the user acknowledgement can come to the controller via a wireless communication from the remote user-interface device or via user interaction with the medication delivery device.

Devices, methods, and systems provided herein can permit a user to stop or quiet an alarm or alert on the remote user-interface device and/or the medication delivery device by pressing one or more appropriate keys or user-selectable icons on the remote user-interface device (e.g., a snooze button) or the medication delivery device, or taking some other interactive action with the remote user-interface device and/or the medication delivery device (e.g., moving the remote user-interface device in a predetermined motion or series of motions). After an alarm or alert is stopped, in some cases, a controller in the medication delivery device may wait a predetermined snooze period of time before re-triggering an alarm or alert by sending a wireless communication intended for the remote user-interface device for the same alarm or alert condition. In some cases, a user will take appropriate action so that the alarm or alert condition is resolved or resolving such that the alarm or alert condition will not be present after the snooze period. In some cases, different alarm or alert conditions will have different predetermined periods of time based on a danger associated with the alarm or alert condition. In some cases, each alarm or alert condition will have the same predetermined periods of time regardless of the danger associated with the alarm or alert condition. For example, in some cases, an alarm for severe hypoglycemia may only be snoozed for a limited amount of time ((e.g., between 5 and 10 minutes), while an alarm for hypoglycemia may be snoozed for a relatively longer period of time (e.g., between 15 and 30 minutes). In some cases, a user can snooze and/or acknowledge an alarm or alert condition via a button on the housing of the medication delivery device. In some cases, medication delivery devices provided herein can include a tap detector and/or a proximity sensor and a user can snooze and/or acknowledge an alarm or alert condition by tapping on the housing of the medication delivery device and/or by motioning (e.g., with the user's hand) within a selected proximity of the delivery device). In some cases, medication delivery devices provided herein will only recognize an acknowledgement via the medication delivery device if there is a predetermined number or pattern of taps, button pushes, or gestures, which can prevent inadvertent button presses or jostling of the medication delivery device from silencing an important alarm. In some cases, alarms or alerts on either the medication delivery device, the remote user-interface device, and/or another remote device can be acknowledged/silenced from one or more of the devices. For example, in some cases a user may hear an audible tone from their remote user-interface device and wish to silence it via quick button press or tap on the medication delivery device even before any audible, visual, or haptic alarm or alert is issued on the medication delivery device. In such cases, the controller in the medication delivery device can send a wireless communication of the acknowledgement to the remote user-interface device to stop the alarm tone. In some cases, the snooze period can depend on the type of alarm or alert. In cases, the snooze period can be the same length of time for all alarm or alert conditions. In some cases, the snooze period can be for a selected period of time, for example, between about 5 minutes and about 30 minutes, between about 10 minutes and about 20 minutes, or about 15 minutes.

A remote user-interface device of systems and methods provided herein can be an intended primary user interface, to provide users with the convenience and discretion offered by the use of remote user-interface devices, such as the user's smartphone. In some cases, methods and systems provided herein can limit the ability of a user to control the medication delivery device without the presence of the remote user-interface device. For example, in some cases, a user will not be able to instruct the medication delivery device to deliver additional medication (e.g., a bolus of medication) without the remote user-interface device. In some cases, the primary user interface can be an application downloadable onto a user's smartphone and adapted to be paired to the medication delivery devices provided herein. Restricting the ability of a user to control the medication delivery device directly may seem counter-intuitive, but redirecting the user's attention to a remote user-interface device can conserve the power supply in the medication delivery device by reducing the power needed to power a robust user interface, as the medication delivery device may be a medication infusion device, intended to be worn on the user's body to provide regular, near continuous, or continuous delivery of medication to the user based on the user's needs, which can make the recharging of a battery in the medication delivery device inconvenient to a user. Remote user-interface devices, such as a smartphone, however, can be more convenient to recharge, and thus can be used to provide better graphics, better sound, and a more intuitive user experience. Additionally, a more robust user experience provided on a remote user-interface device can reduce the opportunity for a user to make a mistake in the delivery of medication. Also, a remote user-interface devices can permit users to check the status of a medication delivery system provided herein without needing to directly access their medication delivery devices.

In some cases, methods, devices, and systems provided herein can additionally include an analyte sensor. For example, in some cases, an insulin delivery system can include a continuous glucose monitor. In some cases, an analyte sensor can be in wireless communication with the medication delivery device and/or the remote user-interface device. In other cases, an analyte sensor can be part of a medication delivery device. In some cases, medication delivery methods, devices, and systems provided herein can automate the delivery of medication to the user based on data from one or more analyte sensors. Automating medication delivery based on feedback from an analyte sensor, however, is only possible if the analyte sensor is providing actionable data. Accordingly, in some cases, methods, devices, and systems provided herein can include a medication delivery device having multiple modes of operation including at least one automation mode (e.g., where medication dosages or rates are changed depending at least in part on data from the analyte sensor) and at least one non-automation mode (e.g., where medication is delivered according to a programmed rate or dosage schedule). Accordingly, medication delivery methods, devices, and systems provided herein can include a medication delivery device adapted to inform the user regarding a current mode of operation even without the presence of the remote user-interface device. For example, in the case of a person with diabetes (PWD) using an insulin delivery system having an automated mode that changes basal rates based on data from a continuous glucose monitor (CGM) and a mode that simply delivers according to a schedule, the PWD may want to be more cognizant of their blood glucose levels if that PWD knows that the system is not actively adjusting basal rates based on CGM data. Additionally, methods, devices, and systems provided herein can be configured to indicate whether actionable data from the CGM is being received by the medication delivery device on the medication delivery device. In some cases, a housing of the medication delivery device can include a light that indicates the current mode of the medication delivery device. In some cases, the light can be adjacent to a mode icon or can illuminate a mode icon.

In some case, methods, devices, and systems provided herein can alert the user to a need to take additional action to correct for an analyte condition based on data from an analyte sensor. For example, in some cases, an insulin delivery system provided herein in wireless communication with a continuous glucose monitor can provide a PWD with a notice regarding a need to correct a current or anticipated hypoglycemic condition by consuming carbohydrates or a notice regarding a need to administer additional insulin to correct a current or anticipated hyperglycemic condition. In some cases, methods, devices, and systems provided herein may include a user interface on the medication delivery device that does not provide a specific or relative analyte concentration, but instead simply provides an indication regarding a recommended corrective action. In other cases, methods, devices, and systems provided herein can provide a generalized indication of whether the user has a high or low analyte concentration, but not display a specific concentration. In either case, methods and systems provided herein can permit the user to see more specific analyte sensor data, such as specific concentrations, by accessing the remote user-interface device. By limiting the ability of the medication delivery device to display specific analyte sensor data, medication delivery methods and systems provided herein can ensure that the remote user-interface device remains the primary user interface, yet ensure that a user is alerted to safety concerns in a timely manner so that the user can take appropriate corrective action. Additional information that may be displayed on the medication delivery device may include an indication that the amount of medication in the medication delivery device is below a threshold or completely depleted, an indication that an amount of power remaining in a battery in the medication delivery device is below a threshold, an indication that the fluid path for the medication is occluded, or an indication that a message is awaiting the user on the remote user-interface device.

In some cases, methods and systems provided herein can have icons on the medication delivery device that match icons used in the remote user-interface device for communicating alarm or alert conditions. Having matching icons on the medication delivery device and on the remote user-interface device can reinforce the meaning behind these icons as the user uses the system. Additionally, matching icons may provide a user with a more robust explanation of an icon at the remote user-interface device.

In some cases, a remote user-interface device can be adapted to permit the user to enter contextual information regarding the user (e.g., about their condition, about their physical attributes, etc.), and the remote user-interface device can wirelessly communicate the contextual information to a controller in the medication delivery device for use in automating the delivery of medication to the user when in an automated mode. For example, in the case of a person with diabetes (PWD) using an insulin delivery system provided herein, the remote user-interface device can be configured to permit the PWD to enter a meal (e.g., enter an amount of carbohydrates consumed by the PWD). In some cases, a PWD can issue a command for the insulin delivery device to deliver a bolus of insulin for a meal. In some cases, insulin delivery methods and systems provided herein can include a remote user-interface device adapted to permit a user to enter exercise, sickness, menses, other medications (e.g., acetaminophen), exogenous insulin, or any other condition that may impact blood glucose levels or the validity of glucose sensor data. In some case, medication delivery devices provided herein may not permit the entry of such contextual information, which can reinforce the use of the remote user-interface device as the primary user interface.

Medication delivery devices provided herein can include the controller that determines an amount of medication to deliver, rather than merely being directed to deliver certain amounts of medication by a controller on a remote device, in order to minimize missed or inappropriate medication deliveries due to a faulty wireless connection between components of systems provided herein. Accordingly, in some cases, systems and methods provided herein can have a controller in the medication delivery device be the center of an on-body network and the source of truth such that any inconsistencies or conflicting instructions are resolved based on the controller in the medication delivery device. In some cases, a medication delivery device can include a programmed schedule of medication deliveries or rates and/or other user-specific dosage parameters that determine appropriate dosages of medication. In some cases, the controller in the medication delivery device can update or personalize these schedules and/or dosage parameters over time and send these updated schedules and/or dosage parameters to the remote user-interface device for viewing or use by the user. In some cases, a medication delivery device receiving a command to deliver a bolus of medication can double check the command to see if the dosage is appropriate and/or safe for the user and/or whether the remote user-interface device may have used the wrong schedule or dosage parameters in making a recommendation to the user based on user entered data. In some cases, methods, devices, and systems provided herein may require a user to confirm a desire to deliver a bolus by pushing a button or tapping the medication delivery device under certain conditions. For example, in an insulin delivery system provided herein, a user entering an extremely large meal bolus for that user, or entering multiple bolus amounts within a short period of time, may be required to confirm the bolus by pressing the button or tapping on the housing of the insulin delivery device.

Medication delivery devices provided herein can include a sound emitter adapted to play one or more alarm or alert tones, a vibration motor, and/or one or more indicator lights and/or illuminable icons, where the sound emitter, vibration motor, indicator lights or icons, or any combinations thereof are adapted to indicate whether the medication delivery device is delivering medication, whether a medication delivery rate or amount is being determined at least in part on real-time data from the analyte sensor, whether real-time data is available to the medication delivery device, whether the medication delivery device is low or out of medication, whether the medication delivery device is low on power, and/or whether a message is awaiting the user on the remote user-interface device. In some cases, the medication delivery device can be an insulin pump having a sound emitter, a vibration motor, indicator lights and/or icons, or any combinations thereof and can be adapted to indicate that the user needs to consume a meal and/or that the user should administer a bolus. For example, in some cases, a predictive algorithm in an insulin pump can predict a dangerously low blood glucose level that will not be corrected by suspending insulin delivery, and thus the insulin pump provided herein can indicate to the user that the user should consume carbohydrates. In some cases, an insulin pump provided herein can predict that a maximum administration of basal insulin allowed by the programming of the pump will not return the user to a target blood glucose value or range within a predetermined amount of time, and thus the insulin pump provided herein can indicate that the user should administer a corrective bolus. In some cases, an insulin pump provided herein may use data from a continuous glucose monitor to detect a possible meal that was not accompanied by a bolus, and may indicate that the user should administer a bolus.

In some cases, methods, systems, and devices provided herein can include a button on the medication delivery device, which can be used, in addition to acknowledging/snoozing alarms and alerts, to check the status of the medication delivery device (e.g., check to see if it is delivering medication, a current mode, and see if there are any outstanding messages). For example, if a user wishes to know the current mode of the medication delivery device, the user can double press the button, and an indication light or icon can illuminate to indicate the current mode of operation (e.g., automated mode or non-automated mode). In some cases, additional icons may illuminate or flash to indicate other conditions or messages awaiting the user on the remote user-interface device. For example, if an amount of medication remaining is below an alert threshold level, but not below an alarm threshold level (e.g., at a level where corrective action may be advisable, but not necessary), pressing the button may cause a message icon to light and/or for an insulin depleted or low icon to flash. In some cases, in order for a user to know that all of the lights or illuminable icons are working properly, certain conditions may cause all of the lights to flash on (e.g., an instruction from the remote user-interface device during a systems check process or whenever medication delivery device receives a new supply of medication). Moreover, the lights or illuminable icons can flash when a user acknowledges or snoozes an alarm using the medication delivery device. Additionally or alternatively, a tap detector can be used to detect a desire from the user to see the system status on the medication delivery device. In some cases, a tap detecting device can be an accelerometer.

In some cases, methods, systems, and devices provided herein can provide audible, visual, and/or haptic alarms via an analyte sensor worn by the user, which can be in addition to or instead of the alarms or alerts provided by the medication delivery device.

One or more cases of the present disclosure may include an on-body networked medication-delivery system. Such a system may include an analyte sensor adapted to generate analyte data for a user and wirelessly transmit the analyte data, and a medication delivery device in wireless communication with the analyte sensor. The medication delivery device can include a medication reservoir or a space to receive a medication reservoir, a drive system adapted to meter the administration of medication out of the medication delivery device, and a feedback feature or features to provide audible, visual, or haptic feedback to a user. The medication delivery device can include a controller adapted to change a dosage of medication based at least in part on the analyte sensor data and can be adapted to issue alarm and alert wireless communications based on a detection of an alarm or alert condition, and a tap detector or button adapted to permit the user to check the status of the medication delivery device or to acknowledge the alert or alarm conditions. The on-body networked medication-delivery system can include a remote user-interface device in wireless communication with the medication delivery device. The remote user-interface device can be adapted to receive the alarm and alert wireless communications from the controller and provide an audible, visual, or haptic alarm or alert message to the user and can permit the user to acknowledge an associated alarm or alert condition. In some cases, the remote user-interface device can be adapted to wirelessly communicate each acknowledgement to the controller. In some cases, the controller can be adapted to trigger an audible, visual, or haptic alarm or alert message via the feedback feature to provide audible, visual, or haptic feedback if the controller fails to receive an acknowledgement of the alert or alarm condition within a predetermined period of time after the controller issues the alarm and alert wireless communication.

In one or more methods, systems, or devices of the present disclosure, the system can be a diabetes management system, and the medication delivery device can be an insulin pump, and the analyte sensor can be a continuous glucose monitor.

In one or more methods, systems, or devices, of the present disclosure, the medication delivery device can be a patch pump.

In one or more methods, systems, or devices, of the present disclosure, the medication delivery device can be an insulin pen or pens.

In one or more methods, systems, or devices of the present disclosure, the medication delivery device can include a durable controller and a disposable pump body, each having a housing and being removably connectable. In such cases, the disposable pump body can include at least the medication reservoir or a space to receive a medication reservoir and the durable controller can include at least the feature to provide audible, visual, or haptic feedback, the controller, and the tap detector or button.

In one or more methods, systems, or devices of the present disclosure, the medication delivery device can include a button.

In one or more methods, systems, or devices of the present disclosure, the feature(s) to provide audible, visual, or haptic feedback to a user can include at least one light associated with an icon.

In one or more methods, systems, or devices of the present disclosure, the remote user-interface device can be adapted to present the icon for an alarm or alert condition.

In one or more methods, systems, or devices, of the present disclosure, the at least one light associated with the icon may not illuminate on the housing until the tap detector detects a tap, or the button is pressed, or until the predetermined period of time.

In one or more methods, systems, or devices of the present disclosure, a user can acknowledge an audible, visual, or haptic alarm or alert message provided by a remote user-interface device by tapping the medication delivery device or pressing the button on the medication delivery device even before the medication delivery device triggers the audible, visual, or haptic alarm or alert message via the feature(s) to provide audible, visual, or haptic feedback.

In one or more methods, systems, or devices of the present disclosure, feature(s) to provide audible, visual, or haptic feedback can include a vibration motor adapted to provide haptic feedback, and the controller can be adapted to provide haptic feedback or audible feedback, upon issuing the alarm and alert wireless communications. Additionally, the audible alarm or alert message that can be triggered if the controller fails to receive an acknowledgement of the alert or alarm condition within a predetermined period of time can be louder or longer in duration than the haptic feedback or audible feedback provided when the controller issues the alarm and alert wireless communications.

In one or more methods, systems, or devices of the present disclosure, the predetermined period of time can be at least 30 seconds and no greater than 1 hour, between 1 minute and 30 minutes, between 3 minutes and 20 minutes, or between 5 minutes and 15 minutes, and the predetermined period of time for an alarm or alert condition can depend on the alarm or alert condition.

In one or more methods, systems, or devices of the present disclosure, an acknowledgement of an alarm or alert may quiet audible or haptic feedback for the alarm or alert condition for a predetermined snooze period of time, and the controller can be adapted to issue new alarm and alert wireless communications after the predetermined snooze period of time if the alarm or alert condition is still detected as being present.

In one or more methods, systems, or devices of the present disclosure, the remote user-interface device can be adapted to present the user with troubleshooting instructions using text, audio, or video to remove the alarm or alert condition, and the medication delivery device may not present any troubleshooting instructions using text, audio, or video.

In one or more methods, systems, or devices of the present disclosure, the medication delivery device can include a housing that contains a non-rechargeable, non-replaceable battery.

In one or more methods, systems, or devices of the present disclosure, the remote user-interface device can be adapted to allow a user to send instructions to the medication delivery device using the remote user-interface device, and the remote user-interface device can prompt the user to confirm the instructions by pressing the button or tapping the controller under certain conditions.

In one or more methods, systems, or devices of the present disclosure, the controller can be adapted to require a user to confirm a bolus delivery by pressing the button or tapping the controller if the dosage is determined by the controller to be unusual based on typical dosage amounts administered by the user, based on the timing the dosage or the timing of a previous dosage, or based on a prediction of how the dosage will change analyte levels for the user.

In one or more methods, systems, or devices of the present disclosure, the medication delivery device can include one or more icons, and one or more lights associated with those one or more icons, indicating whether the medication is being delivered based on the analyte sensor or not or whether there is an error with the analyte sensor.

In one or more methods, systems, or devices of the present disclosure, the medication delivery device can include one or more icons, and one or more lights associated with those one or more icons, indicating that an amount of medication in the medication delivery device is below a threshold level.

In one or more methods, systems, or devices of the present disclosure, the medication delivery device can include one or more icons, and one or more lights associated with those one or more icons, indicating that the user should administer more medication or consume carbohydrates.

In one or more methods, systems, or devices of the present disclosure, the medication delivery device can include one or more icons, and one or more lights associated with those one or more icons, indicating that a more detailed message for the user is awaiting the user on the remote user-interface device.

One or more cases of the present disclosure can include a method for issuing alarms and alerts in an on-body networked diabetes management system. The method can include receiving glucose sensor data from a continuous glucose monitor, and determining a dosage of insulin delivery based at least in part on the glucose sensor data. The method can include detecting an alarm or alert condition, and sending a wireless communication regarding the alarm or alert condition to a remote user-interface device. The method can additionally include triggering an audible, visual, or haptic alarm or alert on the insulin delivery device if the insulin delivery device does not receive an acknowledgement of the alarm or alert condition within a predetermined period of time.

In one or more methods, systems, or devices of the present disclosure, the user can acknowledge the alarm by pressing a button on the insulin delivery device or by tapping the insulin delivery device and by interacting with the remote user-interface device, and the insulin delivery device can receive an acknowledgement of the alarm or alert condition as part of a wireless communication from the remote user-interface device.

In one or more methods, systems, or devices of the present disclosure, such a method can include triggering audible or haptic feedback of the insulin delivery device when sending the wireless communication regarding the alarm or alert condition to the remote user-interface device, and the audible, visual, or haptic alarm or alert on the insulin delivery device after the predetermined period of time can be louder or longer in duration than the feedback initiated when sending the wireless communication.

In one or more methods, systems, or devices of the present disclosure, such a method can include stopping the audible, visual, or haptic alarm or alert on the insulin delivery device when a button on the insulin delivery device is pressed.

In one or more methods, systems, or devices of the present disclosure, the button must be pressed at least twice during a predetermined period of time or according to a predetermined pattern for the audible, visual, or haptic alarm or alert to be stopped.

In one or more methods, systems, or devices of the present disclosure, stopping the audible, visual, or haptic alarm or alert on the insulin delivery device can prevent the triggering of any audible, visual, or haptic alarms or alerts regarding that alarm or alert condition or the sending of any wireless communication regarding the alarm or alert condition for a predetermined period of time. Additionally, one or more methods or processes of the present disclosure can repeat after the predetermined period of time if the alarm or alert condition is present after the predetermined period of time.

In one or more methods, systems, or devices of the present disclosure, the alarm or alert condition can indicate a change from a first mode of operation to a second mode of operation.

In one or more methods, systems, or devices of the present disclosure, the alarm or alert condition can be an indication of an amount of insulin remaining in the insulin delivery device being below a threshold level.

In one or more methods, systems, or devices of the present disclosure, the alarm or alert condition can be an indication of a low glucose condition or a high glucose condition.

In one or more methods, systems, or devices of the present disclosure, the audible, visual, haptic alarm or alert on the insulin delivery device can include the illumination of an icon or next to an icon indicating that the user should eat or should administer insulin.

In one or more methods, systems, or devices of the present disclosure, the alarm or alert condition can be a notice that the continuous glucose monitor is not working, not in range, or not reliable.

In one or more methods, systems, or devices of the present disclosure, the alarm or alert condition can be a notice about a possible occlusion, a possible air bubble, a possible missed meal announcement, a possible need to change an infusion set, a possible need to calibrate a CGM, a possible need to replace the CGM, or a possible need to check ketone levels, and the audible, visual, haptic alarm or alert on the insulin delivery device can include the illumination of an icon or next to an icon indicating that the user should check the remote user-interface device for information about the alert.

One or more cases of the present disclosure can include an insulin delivery device adapted for wireless communication with a continuous glucose monitor and a remote user-interface device. The insulin delivery device can include an insulin reservoir or a space to receive an insulin reservoir, and a drive system adapted to meter the administration of insulin out of the insulin delivery device. The insulin delivery device can include a wireless transmitter and receiver adapted to send and receive wireless communications from at least a continuous glucose monitor and a remote user-interface device, and a controller adapted to change a dosage of medication based at least in part on data from the continuous glucose monitor and adapted to issue alarm and alert wireless communications based on a detection of an alarm or alert condition. The insulin delivery device can additionally include a housing containing at least the controller and the wireless transmitter and receiver, a tap detector within the housing or a button on the housing adapted to permit the user to check the status of the insulin delivery device or to acknowledge alert or alarm conditions, and one or more lights adapted to illuminate icons or adjacent to icons on the housing indicating a mode of operation of the insulin delivery device and whether insulin is being delivered to the user.

In one or more methods, systems, or devices of the present disclosure, an insulin delivery device can include one or more lights or another visual or audio cue adapted to illuminate icons or adjacent to icons on the housing indicating that a message is awaiting the user on the remote user-interface device.

In one or more methods, systems, or devices of the present disclosure, an insulin delivery device can include one or more lights adapted to illuminate icons or adjacent to icons on the housing indicating that the user has a blood glucose condition requiring the consumption of carbohydrates or the administration of additional insulin.

In one or more methods, systems, or devices of the present disclosure, the user cannot administer additional insulin using the insulin delivery device without accessing the remote user-interface device.

In one or more methods, systems, or devices of the present disclosure, the controller can be adapted to evaluate whether a wireless communication from a remote user-interface device is within one or more predefined parameters.

In one or more methods, systems, or devices of the present disclosure, the controller can be adapted to send a wireless communication to the remote user-interface device indicating that a bolus is outside of one or more predefined parameters, or indicating the user must confirm the bolus on the insulin delivery device by tapping or pressing the button.

In one or more methods, systems, or devices of the present disclosure, an insulin delivery device can include one or more lights adapted to illuminate icons or adjacent to icons on the housing indicating that there is a problem with the data being received, or a lack of data being received, from the continuous glucose monitor.

One or more cases of the present disclosure can include a medication delivery system that includes a medication delivery device and a remote user-interface device, where the medication delivery device and the remote user-interface device can be in wireless communication. The medication delivery device can be adapted to automatically administer medication according to a programmed rate, a programmed schedule, or based on analyte sensor data without user input. The remote user-interface device can be adapted to receive user commands for the medication delivery device to administer additional doses of medication, adjust the programmed delivery rate or schedule, or adjust an algorithm that determines a dosage based on the analyte sensor data. Additionally, both the remote user-interface device and the medication delivery device can be adapted to provide audible, visual, or haptic feedback to issue an alarm or alert regarding the ability of the medication delivery device to deliver medication. The medication delivery device can be adapted to detect a condition that prevents the delivery of medication and send an alarm wireless communication to the remote user-interface device regarding the condition. The remote user-interface device can issue an audible, visual, or haptic alarm when the alarm wireless communication is received, and can provide a feature for the user to acknowledge the alarm. The remote user-interface device can send an acknowledgement wireless communication to the medication delivery device upon the user acknowledging the alarm, and the medication delivery device can be adapted to issue an audible, visual, or haptic alarm after a predetermined period of time after the alarm wireless communication is sent unless the medication delivery device receives the acknowledgement wireless communication during the predetermined period of time.

In one or more methods, systems, or devices of the present disclosure, the medication delivery device can include a feature to receive a user's acknowledgement an audible, visual, or haptic alarm to silence the alarm.

In one or more methods, systems, or devices of the present disclosure, the medication delivery device can include an insulin infusion pump, the medication can be insulin, and the remote user-interface device can be a smartphone.

In one or more methods, systems, or devices of the present disclosure, such a system can include a continuous glucose monitor in wireless communication with the insulin infusion pump, and the insulin infusion pump can deliver different amounts or rates of insulin based on glucose data from the continuous glucose monitor.

In one or more methods, systems, or devices of the present disclosure, the insulin infusion pump may not be adapted to display specific concentrations of the glucose data, but can be adapted to send glucose data wireless communications to the smartphone, and the smartphone can be adapted to display specific concentrations of the glucose data.

In one or more methods, systems, or devices of the present disclosure, the insulin infusion pump can be adapted to illuminate one or more icons, or a light next to one or more icons, that indicate that the user is in or expected to experience hypoglycemic state or a hyperglycemic state, that indicate that the user should administer more insulin, or that indicate that the user should consume food, and that light can become illuminated when the insulin infusion pump issues an issue an audible, visual, or haptic alarm or when the user acknowledges the alarm on the insulin infusion pump.

In one or more methods, systems, or devices of the present disclosure, the insulin infusion pump can be adapted to illuminate one or more icons, or a light next to one or more icons, that indicate that the user is in out of insulin, wherein the light becomes illuminated when the insulin infusion pump issues an issue an audible, visual, or haptic alarm or when the user acknowledges the alarm on the insulin infusion pump.

The details of one or more implementations of the disclosure are set forth in the accompanying drawings and the description below. Other features, objects, and advantages of the disclosure will be apparent from the description and drawings, and from the claims.

DESCRIPTION OF DRAWINGS

FIG. 5A depicts a visual indication for the alarm on an insulin delivery device. FIGS. 5B and 5C depict a visual indication for the alarm on a remote user-interface device.

FIG. 7A depicts an example of how an alert may appear on a remote user-interface device.

FIG. 7B depicts an example of how a notification may appear on a remote user-interface device.

FIGS. 15A-15C illustrate how example notification lights on an automated medication infusion pump can inform a user about the status of the medication delivery system.

FIGS. 16A and 16B illustrate example alarms and how a user can snooze the alarms.

Like reference symbols in the various drawings may indicate like elements.

MODE(S) FOR CARRYING OUT THE INVENTION

Methods, devices, and systems provided herein can be used to deliver any appropriate medication for the treatment of any appropriate disease or condition. The embodiments described below relates to an insulin delivery system for the management of diabetes, however, the delivery of other types of medications for other diseases are also contemplated. For example, in addition to diabetes, methods, devices, and systems provided herein can be used to treat unresponsive infections, cancer, cancer-related pain, chronic pain, gastrointestinal diseases or disorders, congestive heart failure, hemophilia, immune deficiencies, multiple sclerosis, and rheumatoid arthritis. In some cases, methods, devices, and systems provided herein can use analyte sensor data to automate the delivery of medication. Although the example embodiments described below are specific to an insulin delivery device adapted to automate basal insulin deliveries based on data from a continuous glucose monitor, medication delivery systems that do not include and/or consider data from an analyte sensor are also contemplated.

As used herein, the term "substantially" in reference to a given parameter feature(s) and includes to a degree that one skilled in the art would understand that the given parameter, property, or condition is met with a small degree of variance, such as within acceptable manufacturing tolerances. For example, a parameter that is substantially met may be at least about 90% met, at least about 95% met, or even at least about 99% met.

Figure 1A:
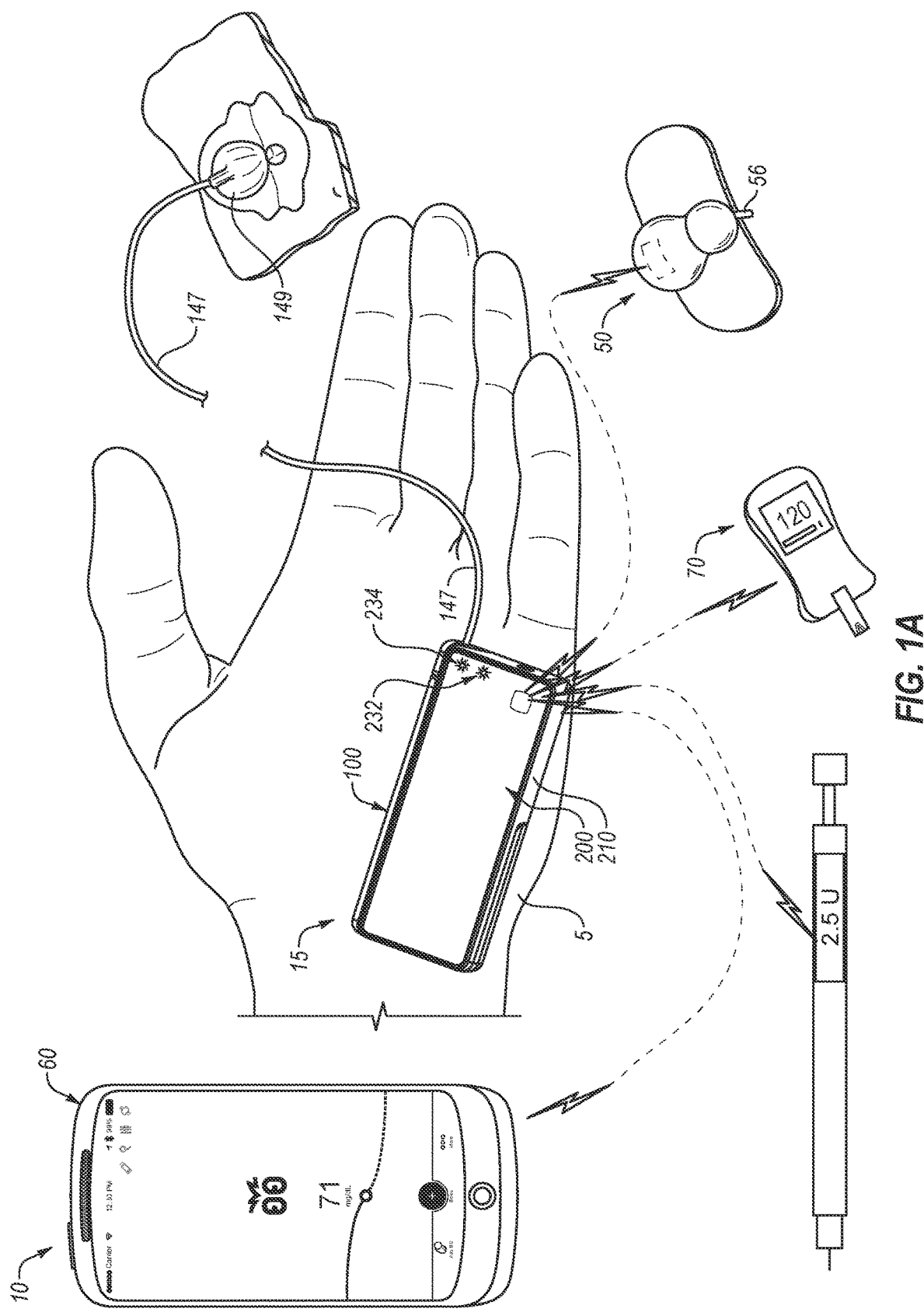
FIG. 1A is a perspective view of a first example medication delivery system including a module medication delivery device, at least one analyte sensor, and a remote user-interface device.

FIG. 1A depicts an example medication delivery system provided herein, which includes at least a medication delivery device 15 and a remote user-interface device 10. As shown, the medication delivery device 15 is an insulin delivery device, more specifically an insulin infusion pump. As shown, the medication delivery device 15 can be sized to fit within an adult human's hand 5. In some embodiments, the medication delivery system depicted in FIG. 1A may be similar to or the same as that disclosed in U.S. Patent Application Publication No. US 2017/0203037 A1, published Jul. 20, 2017, the disclosure of which is hereby incorporated herein in its entirety by this reference.

FIG. 1A further depicts analyte sensor 50, which are shown as both being in wireless communication with the medication delivery device 15. Analyte sensor 50 can be a continuous glucose monitor (CGM, and may be referred to as CGM 50) adapted to have a sensor probe 56 sit subcutaneously on a user's skin and provide regular (e.g., every 1 minute, every 3 minutes, every 5 minutes, every 10 minutes, every 30 minutes, or at some interval in between) or irregular (e.g., variable depending on one or more previous blood glucose readings) blood glucose readings. The medication delivery device 15 can then use the data from CGM 50 to alter medication dosages or delivery rates. Although the incorporated by reference U.S. Patent Application Publication No. US 2017/0203037 A1 describes certain techniques for changing between basal rates of 0×, 1×, and 2× (and optionally 3× or other multipliers) of a baseline basal rate, other techniques for using CGM to automate basal insulin delivery rates or provide microboluses of insulin to a user are contemplated and known in the art. In some cases, the medication delivery device 15 can use the CGM data in a proportional-integral (PI) controller, a derivative controller, a proportional-integral-derivative (PID) controller, a model predictive controller, etc. Additionally, as described in the incorporated by reference U.S. Patent Application Publication No. US 2017/0203037 A1, the medication delivery device 15 can have multiple modes, including an automated mode and a non-automated mode (e.g., a personalized mode), which can be entered and exited based on the availability of actionable CGM data (and optionally other conditions) and/or one or more user preferences. Accordingly, the medication delivery device 15 can include indicator lights 232 and 234, which can be used to indicate a mode of operation, and optionally certain error conditions. Additional details about possible indicator lights and arrangements are described below in relationship to FIGS. 2-15.

Figure 1B:
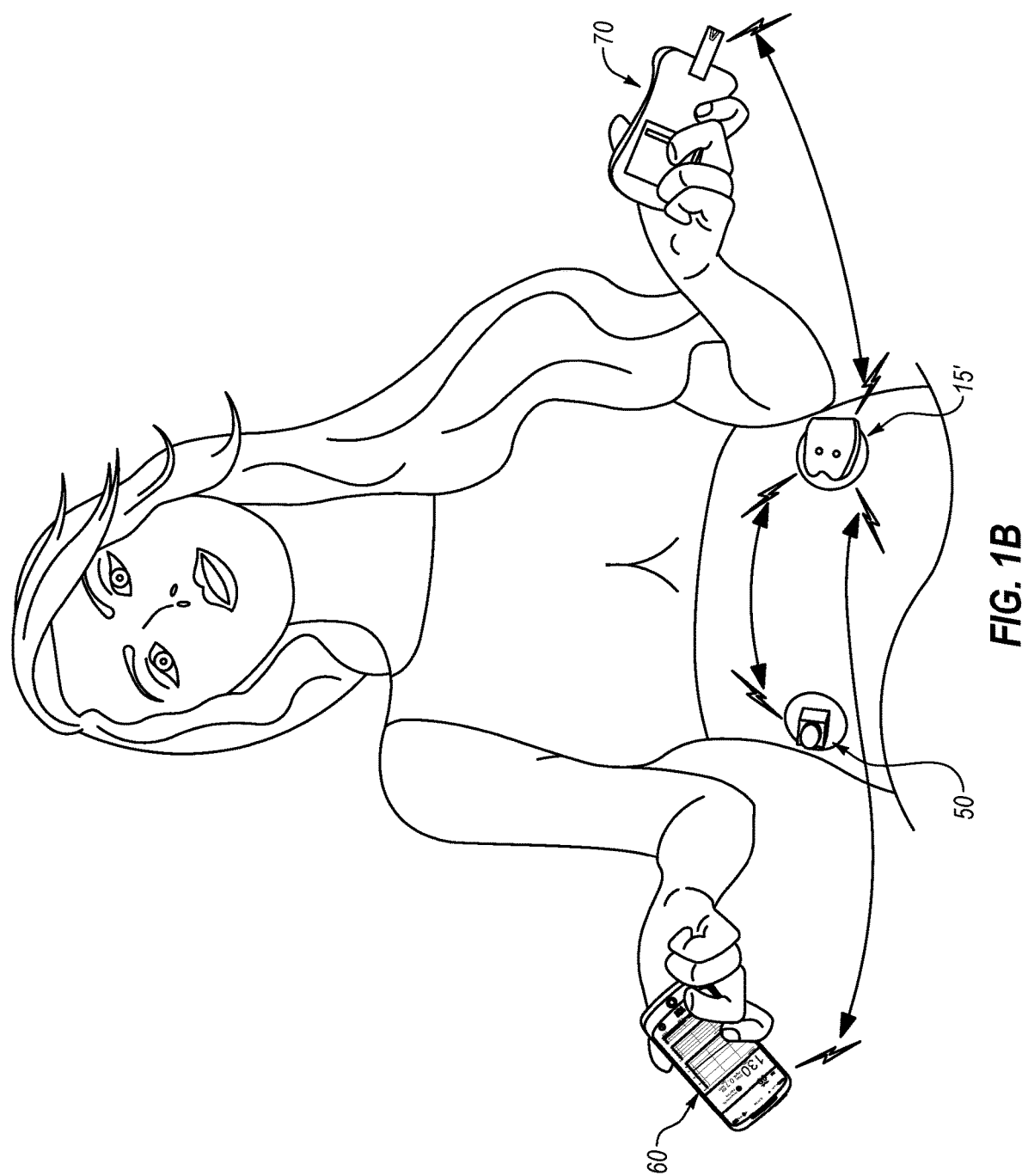
FIG. 1B is a perspective view of a second example medication delivery system including a patch pump-type medication delivery device, at least one sensor, and a remote user-interface device.

FIG. 1B depicts a medication delivery system according to a second embodiment where a medication delivery device is a patch pump 15', which also can be used to deliver insulin in an insulin delivery system and can use CGM data from CGM 50 to automate insulin dosages or rates. As shown, patch pump 15' also includes indicator lights. Although FIGS. 2-15 show a medication delivery device user interface on a medication delivery device similar to that of FIG. 1A, the features shown and described below are equally applicable to patch pumps or other suitable delivery devices. Also as shown, patch pump 15' can include a wireless receiver and transmitter to send and receive wireless communications from a remote user-interface device 60, the CGM 50, and a blood glucose meter 70, and can include a controller adapted to automate insulin based at least in part on CGM data using any appropriate control algorithm.

Figure 2:
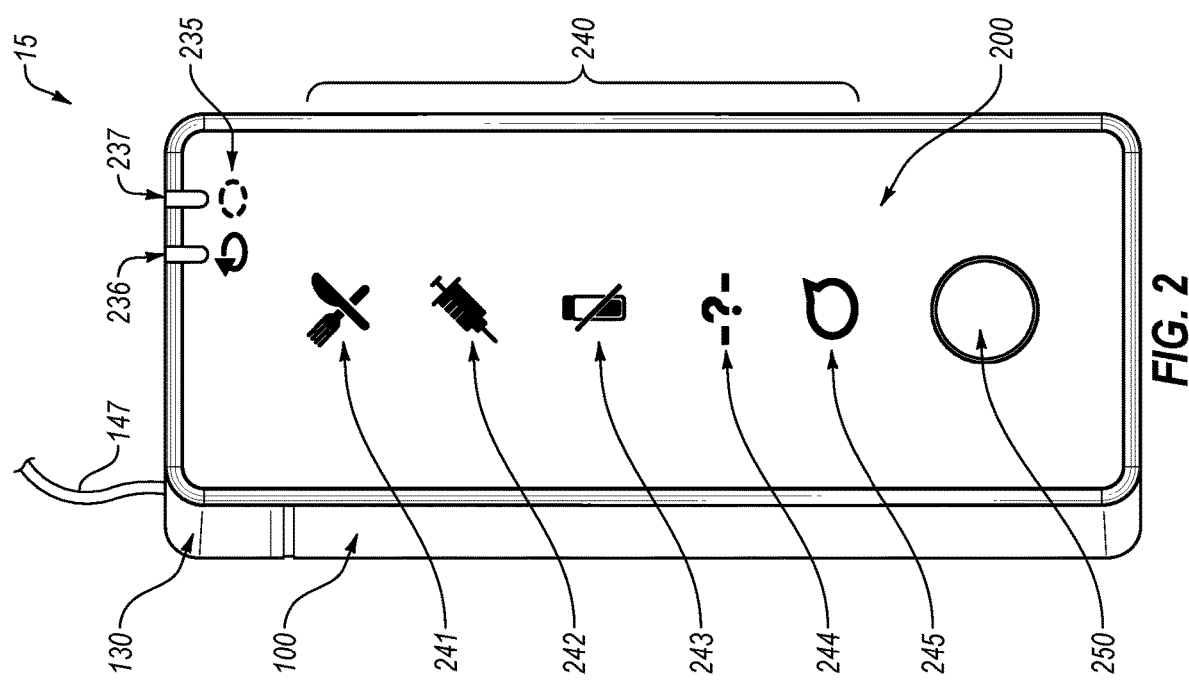
FIG. 2 is an example view of a module medication delivery device showing an example medication delivery device user interface.

FIG. 2 depicts an example user interface for the medication delivery device 15, specifically for an insulin infusion pump. In some cases, the medication delivery device 15 can be a modular medication delivery device including a disposable pump body 100 and a durable controller 200, as described in the incorporated by reference U.S. Patent Application Publication No. US 2017/0203037 A1. However, this user interface can be applied to unitary medication delivery devices, as well as to patch pumps (such as those shown in FIG. 1B) and any other suitable medication delivery device, particularly those used to deliver insulin. As shown, a front face of medication delivery device 15 can include a button 250. In some cases, medication delivery devices provided herein can include only one button. In some cases, medication delivery devices provided herein can have a plurality of buttons. In some cases, medication delivery devices provided herein can only have buttons capable of snoozing, quieting, or acknowledging alarms, alerts, or notifications and for checking the system status.

The user interface can additionally include a plurality of indicator lights and/or illuminable icons. As shown, indicator lights 236 and 237 can be positioned adjacent to icons 235. As shown, lights and icons 235-237 can inform the user whether the user is in an automated (e.g., closed-loop, open-loop, partially closed-loop, etc.) mode or a non-automated (e.g., personalized) mode. The illumination of light 236 indicates an automated mode and the illumination of light 237 indicates a non-automated mode. In some cases, additional mode lights can be used to indication other modes. In some cases, a single light can be used to indicate a mode (e.g., a color, flashing pattern, or other light characteristic) can be used to indicate the current mode. In some cases, a plurality of alarm or alert illuminable icons 240 can be positioned on the housing to indicate the need for the user to take certain actions. Although the mode lights 236 and 237 are depicted as being adjacent to icons and icons 241-245 being indicated as being illuminable, the opposite is also a contemplated design, and all icons could have an adjacent light or all icons could be illuminable. As shown, illuminable icon 241 is illuminated, while the other icons 242-245 are not illuminated. Illuminable icon 241 represents a need to eat, illuminable icon 242 indicates a need to take insulin, illuminable icon 243 indicates a depletion of insulin in the medication delivery device 15, illuminable icon 244 indicates an error with CGM data, and illuminable icon 245 indicates that a message awaits the user on the remote user-interface device. Although specific icons are depicted, other icons are also contemplated.

Figure 3:
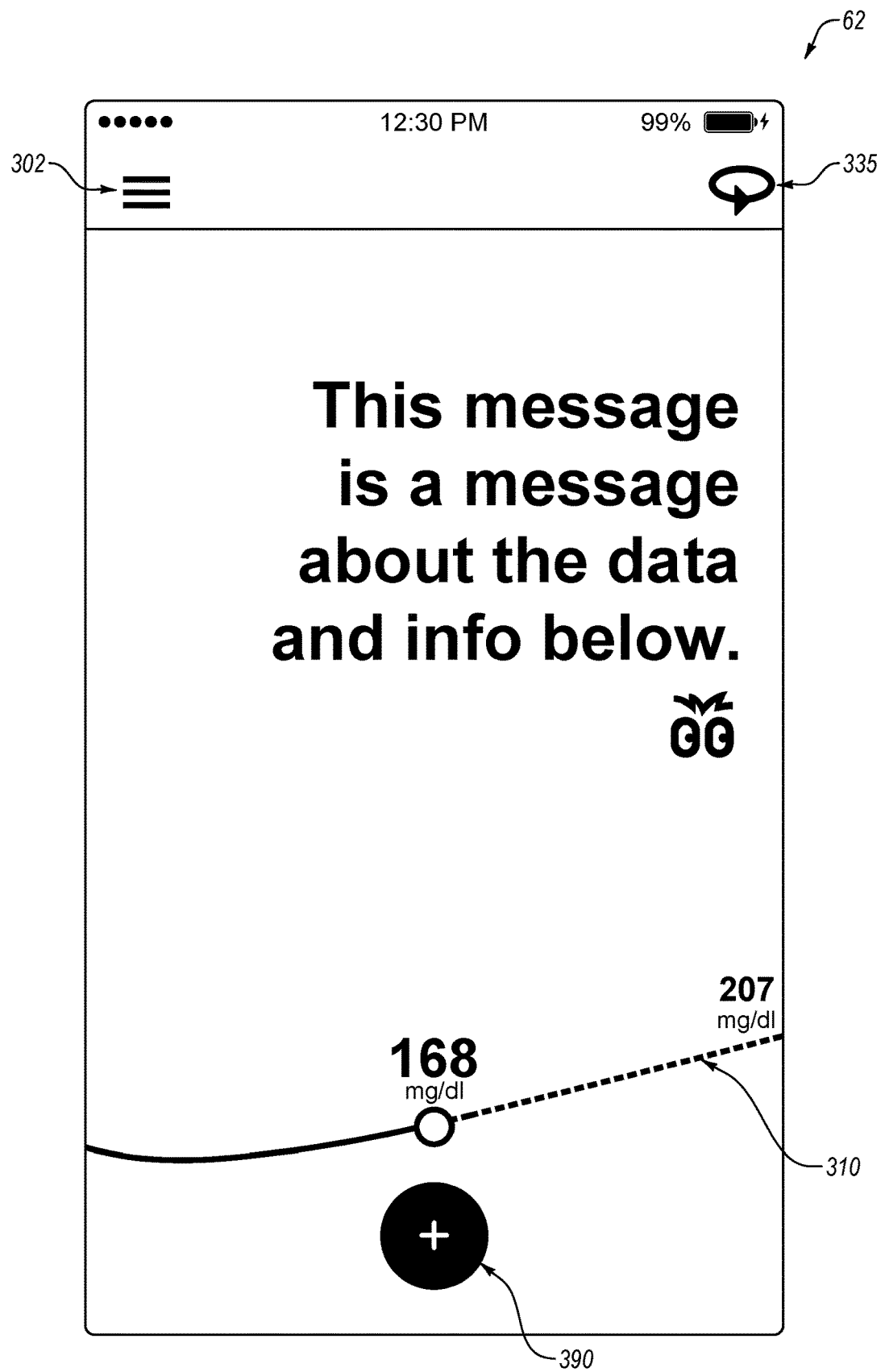
FIG. 3 depicts an example user interface landing home screen for a remote user-interface device.

FIG. 3 depicts an example home landing screen 62 for remote user-interface device 10. As described in the incorporated by reference U.S. Patent Application Publication No. US 2017/0203037 A1 (using a different name), remote user-interface device 10 can be a smartphone or any other suitable remote device having a suitable display and robust data entry capabilities (e.g., a PDA, a tablet computer, a music-playing device). In some cases, the remote user-interface device 10 has an application stored in memory to execute the user interfaces and user experience provided herein. As shown, the remote user interface 60 includes a navigation menu 302, a mode indicator icon 335, a message, blood glucose data display 310 illustrated with a blood glucose value, a blood glucose trend line, and a blood glucose prediction, and a bolus button/user-selectable icon 390. As shown, mode indicator icon 335 can resemble or match an icon 235 on the medication delivery device housing 210, which can reinforce the meaning of the icon. In some cases, if a user taps on the icon in the remote user interface 60, a message can appear explaining the meaning of the icon. If a user taps on the blood glucose data display 310, a message can appear providing an explanation of the display and/or bring the user to a more specific display of blood glucose data and/or insulin delivery data.

Examples of more detailed chart displays of blood glucose data aligned with insulin delivery data are depicted and described in the incorporated by reference U.S. Patent Application Publication No. US 2017/0203037 A1. Navigation menu 302 can be pressed or tapped by the user to access other functions of the remote user-interface device, such as instructional videos on performing certain tasks, entering other contextual information, setting up personal preferences, etc. Bolus button/user-selectable icon 390 can be prominent on the home screen because it can be one of the most important functionalities of the remote user-interface device 10 with respect to controlling the operation of the medication delivery device 15. An additional important function of the remote user-interface device 10 being to provide the user with actionable information regarding alarms, alerts, and other notifications useful for managing/treating diabetes. In some cases, pressing the bolus button 390 can bring the user to a bolus calculator that helps the user determine a bolus based on entered food information, blood glucose data, stored personal dosage parameters (e.g., an insulin sensitivity factor and a carbohydrate-to-insulin ratio), and an estimation of unacted insulin delivered (e.g., insulin on board (IOB)).

Figure 4:
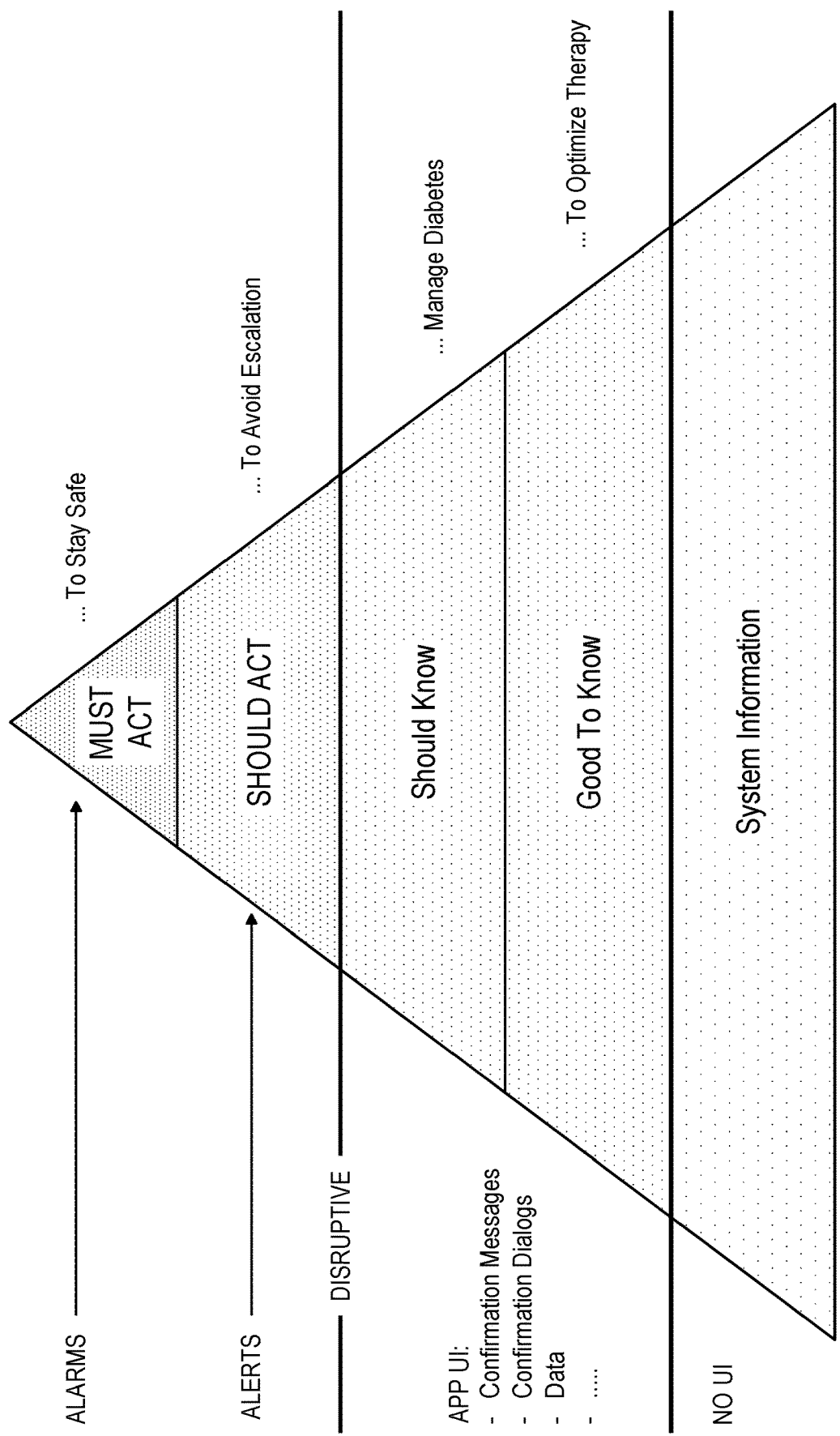
FIG. 4 is an infographic regarding alarms, alerts, and other notices used in a diabetes management system.

FIG. 4 depicts an infographic depicting conceptually a distinction between alarms, alerts, and notifications, as those terms are used in the present disclosure. In some cases, a notification regarding a condition, if not acted upon by a user, can result in that condition triggering an alert or an alarm. In general, an alarm condition is something that requires a user's attention to stay safe, or in other words, a condition that could result in personal injury or other health complications if the condition is not addressed. An example alarm might be triggered by a severe hypoglycemic event. An alarm event might also be triggered if the medication delivery device has a nearly dead battery or is totally depleted of insulin or if there is an occlusion in an infusion catheter 147. In many cases, an alarm condition may typically be avoided if a user takes action based on the triggering of alerts. An alert condition is something that could lead to an alarm condition, or that needs attention. However, an alert condition does not have the same urgency or immediacy as an alarm condition. For example, a predicted hypoglycemic event may trigger a potential hypoglycemic event alert using different threshold criteria than the severe hypoglycemic event condition so that a user can take corrective action before blood glucose levels drop to a level triggering an alarm event. Other possible alerts may include hyperglycemic events, a failure to receive actionable CGM data, a need to calibrate the CGM, an amount of insulin being below a higher alert threshold, and/or a need to conduct system maintenance or replace system components based on their recommended user life. Alarms and alerts should be disruptive to the user because the user should or must act to remain safe, thus methods, systems, and devices provided herein ensure that a user receives prompt notice of these alarm or alert conditions even if the remote user-interface device is not immediately available to the user. The non-disruptive notifications, however, are things that a user can use to better manage or optimize their treatment of diabetes, but are not urgent, thus they can remain accessible upon demand by the user on the remote user-interface device. Such information might be data about past, current, or predicted blood glucose values that are in a safe range, past and current insulin doses and basal delivery rates, previously entered meal sizes, etc. Additionally, there is system information unrelated to the treatment of diabetes, which can be hidden from the user.

Figure 5C:
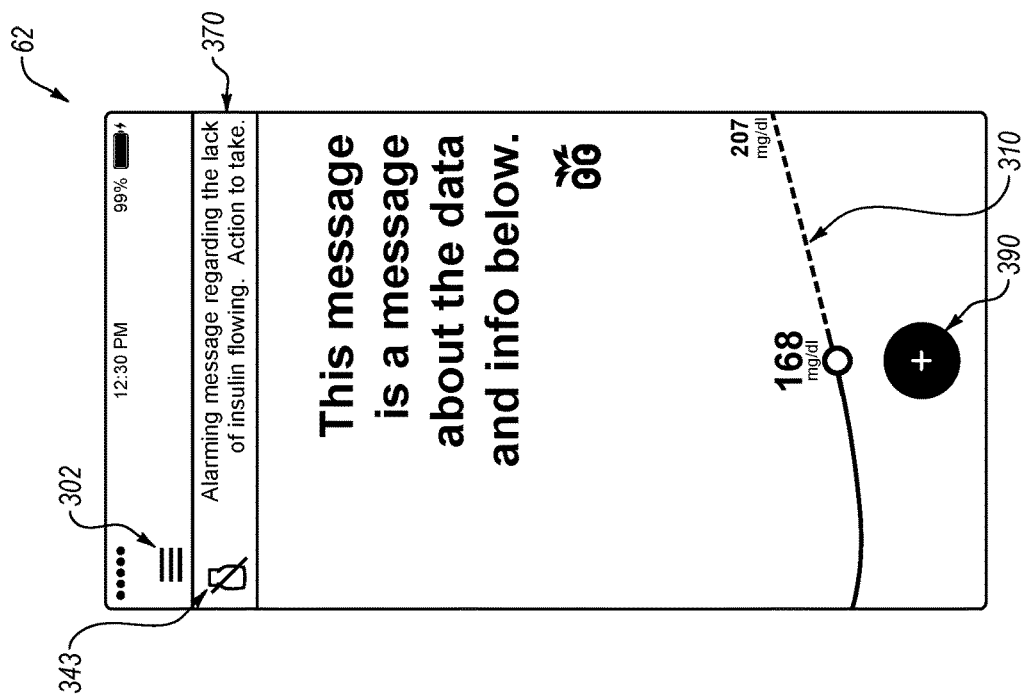
FIGS. 5A-5C depict example alarms for a lack of insulin flowing in an insulin delivery system provided herein.
Figure 5B:
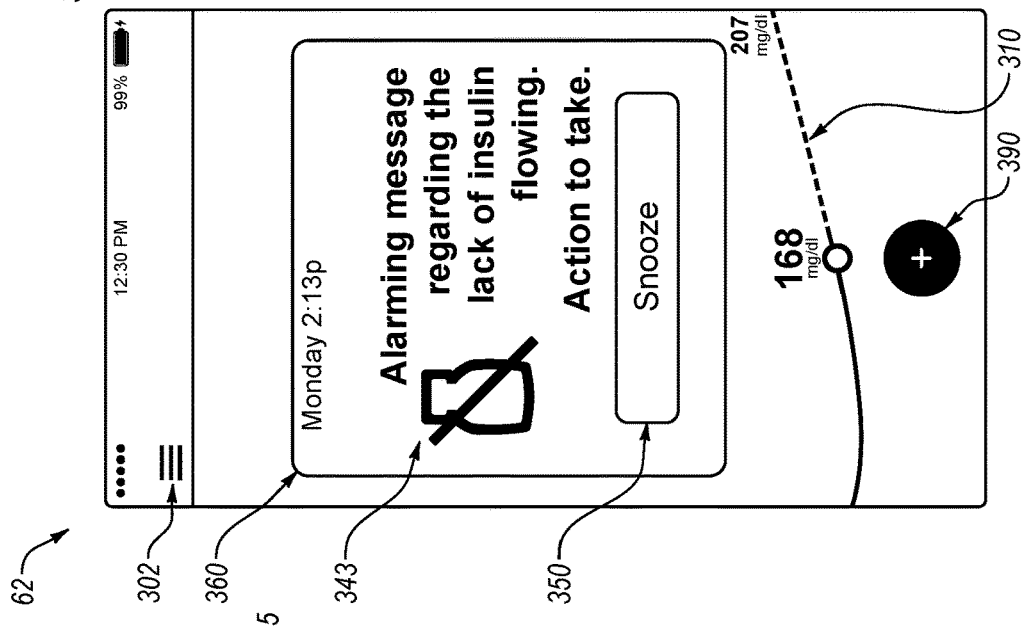
Figure 5A:
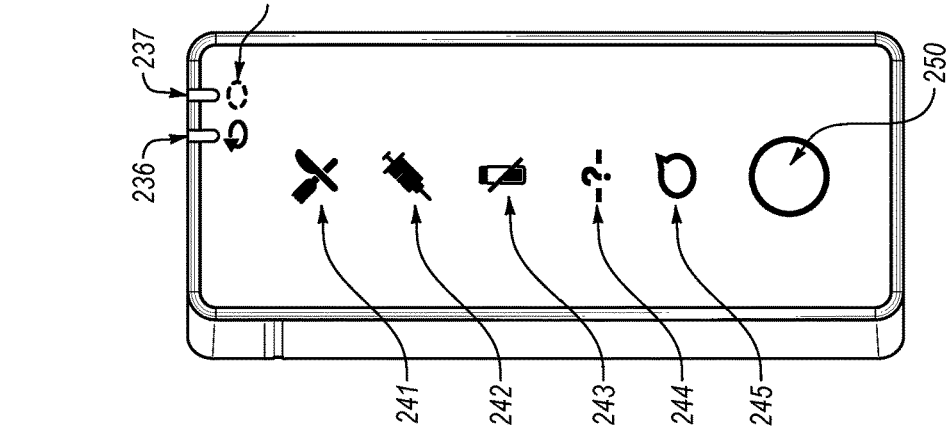

FIGS. 5A, 5B, and 5C illustrate how an alarm condition related to a lack of insulin flowing can be displayed on the medication delivery device 15 (FIG. 5A) and on the remote user-interface device (FIGS. 5B and 5C). In each case, the visual indicators shown can be accompanied with an audible alarm tone and/or haptic feedback. As shown, the icon 243 for this alarm condition on the medication delivery device 15 matches an icon 343 displayed on the remote user-interface device (FIGS. 5B and 5C). As shown in FIG. 5B, an alarm notification box 360 can pop up when the user accesses an app on a smartphone. By pressing snooze button 350, the user can stop the audible alarm tone and/or haptic feedback. Similarly, by pressing button 250 on medication delivery device 15, any audible alarm tone sounding from the medication delivery device 15 can be stopped. In some cases, pressing button 250 can result in the medication delivery device 15 sending a wireless communication to remote user-interface device 10 to stop an audible alarm tones or haptic feedback, and vice-versa regarding using button 350 to stop alarm tones and haptic feedback on the medication delivery device. Regarding FIG. 5A, illuminating icon 243 can in some case be illuminated as soon as audible and/or haptic alarming occurs on the medication delivery device 15, or can be illuminated at the point in time when the user presses button 250 to silence the audible/haptic alarm to show the user the reason for the alarm. In either cases, illuminating icon 243 can remain illuminated after snoozing the alarm for at least a predetermined period of time (e.g., between 1 second and 5 minutes, or between 2 seconds and 1 minute, or between 5 seconds and 30 seconds). Referring back to FIG. 5B, alarm notification box 360 can appear over the home landing screen of the remote user-interface device, but can appear over other screens of the user interface.

Figure 6:
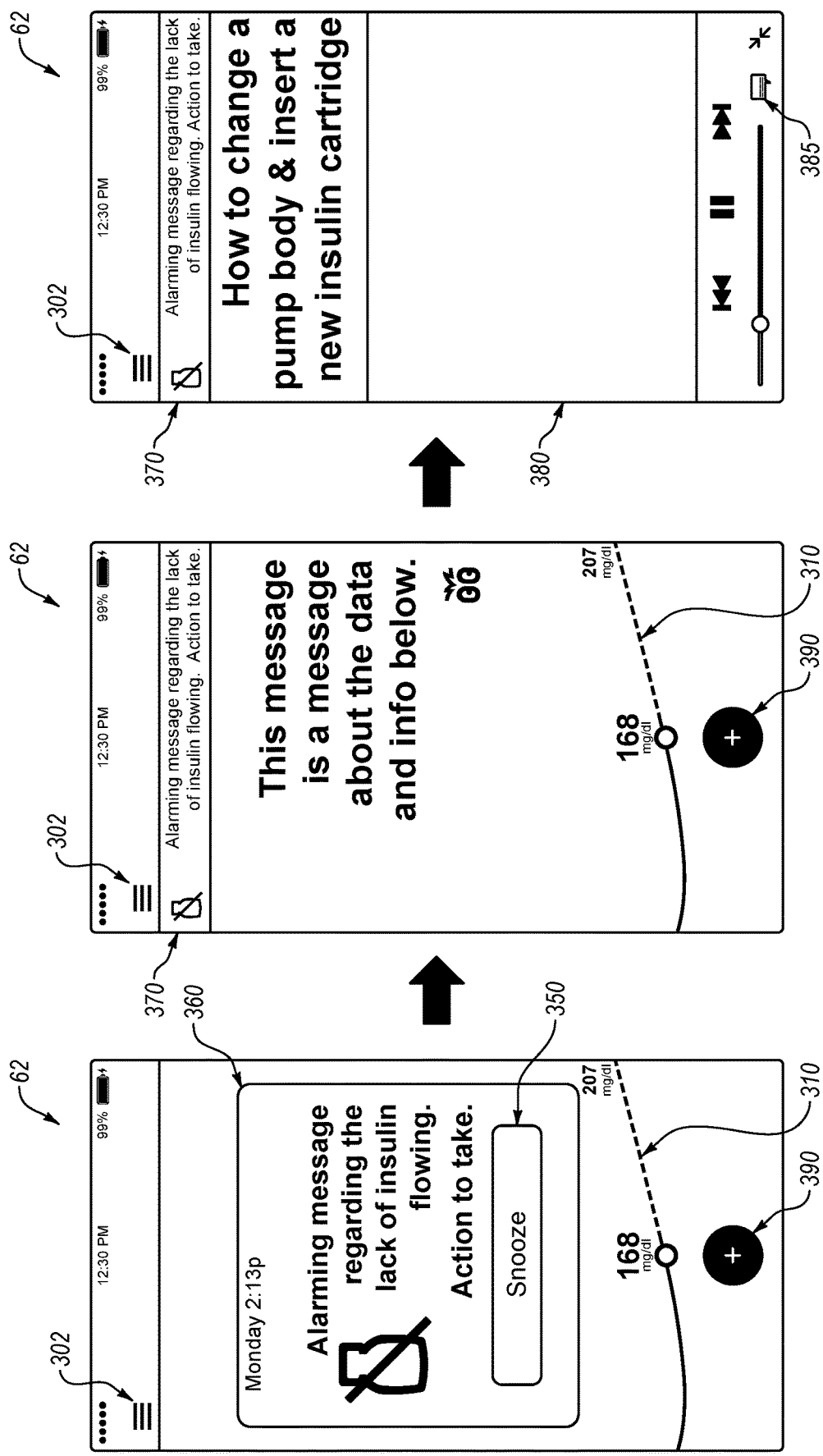
FIG. 6 depicts an example of how the alarms of FIGS. 5A-5C can progress on the remote user-interface device to a tutorial on how to resolve the alarm condition.

As shown in FIG. 6, after an alarm is snoozed by pressing button 350 on the user interface of remote user-interface device 10, the alarm notification box may become an alarm notification banner, still retaining the same icon 343. In some cases, a user may click on this banner 370 to find out additional information about how to resolve the alarm condition (as indicated in FIG. 6). FIG. 6 shows the flow of where a user may push or tap banner 370 to be taken to a screen that includes a troubleshooting view 380, which may optionally include a chat icon 385 to allow the user to live chat with an expert on using the medication delivery system to help the user troubleshoot the problem.

FIG. 7A depicts an example of how an alert may appear on a remote user-interface device. As shown, an alert may appear as an alert box 760, which may be acknowledged by the user, similar to the way that an alarm can be acknowledged by a user. As shown, the icon in alert box 760 mirrors illuminable icon 245, which can indicate that there is a message available for the user on the remote user-interface device. By having icons mirrored between the remote user-interface and the medication delivery device, the messages associated with each of icons 241-245 can be reinforced in the user's mind. As shown, the message can be about an overdue maintenance task, such as changing any infusion set 149.

FIG. 7B depicts an example of how a notification may appear on a remote user-interface device. Because notifications do not require immediate action, they can appear as a notation 770 on the navigation menu 302 to indicate to the user that a non-urgent message is available for them. In some cases, a snoozed alert can become a notification message available as a notation 770 until such time as an alert snooze time period runs out or the alert condition escalates to a different alarm condition. In some cases, certain alert conditions can become banners after being snoozed.

Figure 8B:
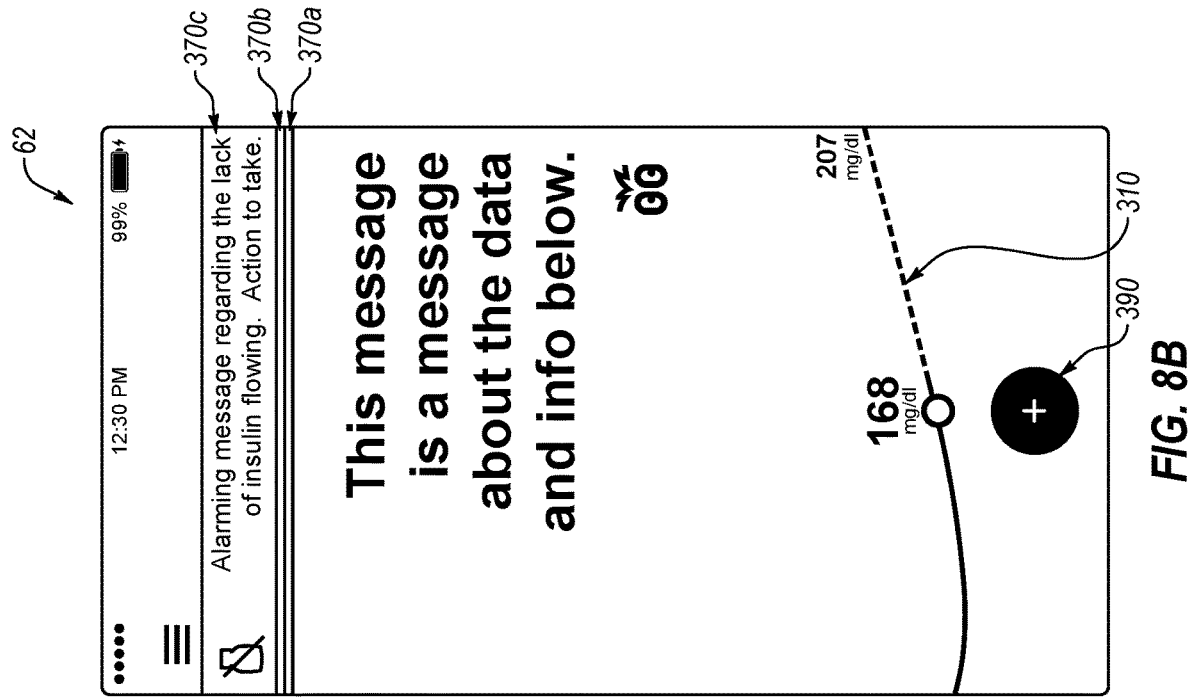
FIGS. 8A and 8B depict examples of how multiple alarms may appear on a remote user-interface device.
Figure 8A:
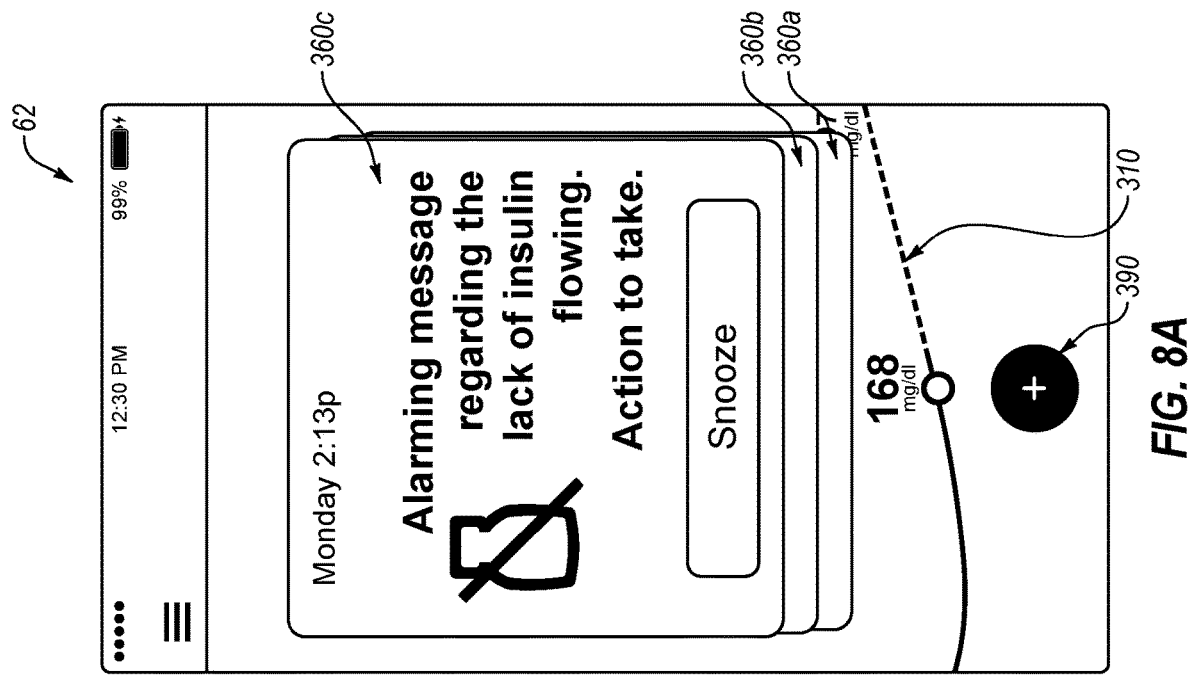

FIGS. 8A and 8B depict examples of how multiple alarms may appear on a remote user-interface device. FIG. 8A depicts multiple alarm boxes 360a, 360b, and 360c stacked on top of each other. As each is cleared, the box underneath is revealed, and each becomes a banner 370a, 370b, 370c, each stacked on top of each other until the user resolves the alarm condition. In some cases, the most recently triggered alarm is stacked on top. In some cases, alarm conditions can have an order of priority and the most urgent alarm condition can be stacked on top. In some cases, alert boxes 760 can be in a stack of boxes. In some cases, alarm and alert boxes can be distinguished by color and/or size. In some cases, the alert boxes 760 may be staggered along the screen (e.g., vertically staggered) such that at least a portion (e.g., an entirety) of each alert box 760 is visible.

Figure 9A:
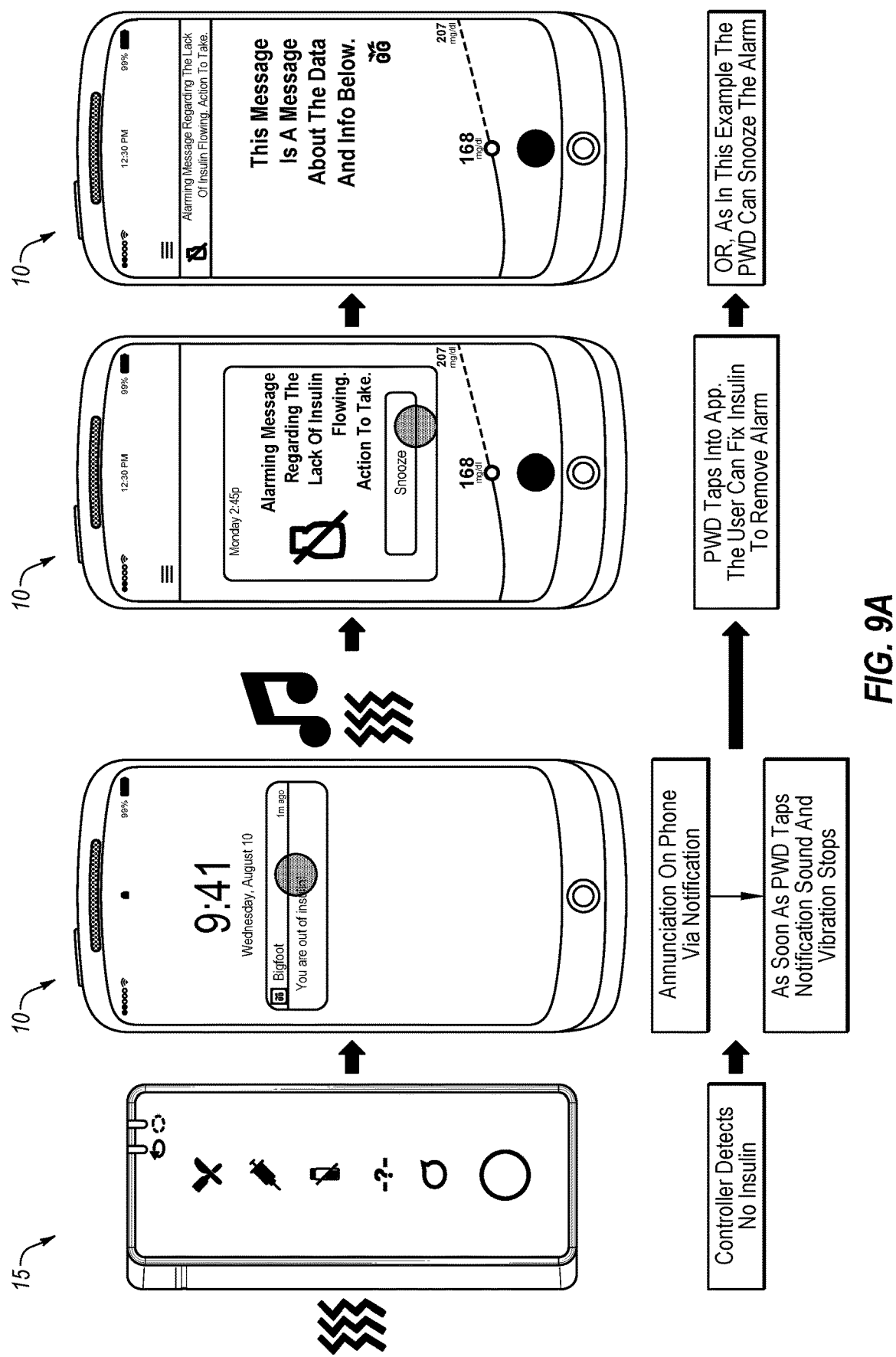
FIG. 9A depicts an example progression of alarm notifications for a lack of insulin flowing if the user acknowledges the alarm condition within a predetermined period of time.

FIG. 9A depicts an example progression of alarm notifications for a lack of insulin flowing if the user acknowledges the alarm condition within a predetermined period of time (where user clicks or acknowledgements are indicated with a circle). As shown, the medication delivery device 15 first detects that there is no insulin or a blockage of insulin and then sends a wireless message to remote user-interface device 10. In some cases, medication delivery device 15 can vibrate upon detecting the alarm condition and/or upon sending the wireless communication. This vibration may be short in duration, and be present in order to let the user know that a notification from the remote user-interface device 10 (e.g., a smartphone, such as an iPHONE®) is from the medication delivery device. After receiving the wireless communication, a message (e.g., an iOS message) can appear on a smartphone version of a remote user-interface device along with sound and/or vibration, assuming that the user permits such notices, vibrations, or sounds for the app of the medication delivery system. The user can then select the message to be brought to the app, where the user can snooze the message and click on the banner to learn how to resolve the issue. In some cases, the user will know how to resolve the issue from experience and not need to click on the banner to resolve the alarm condition.

Figure 9B:
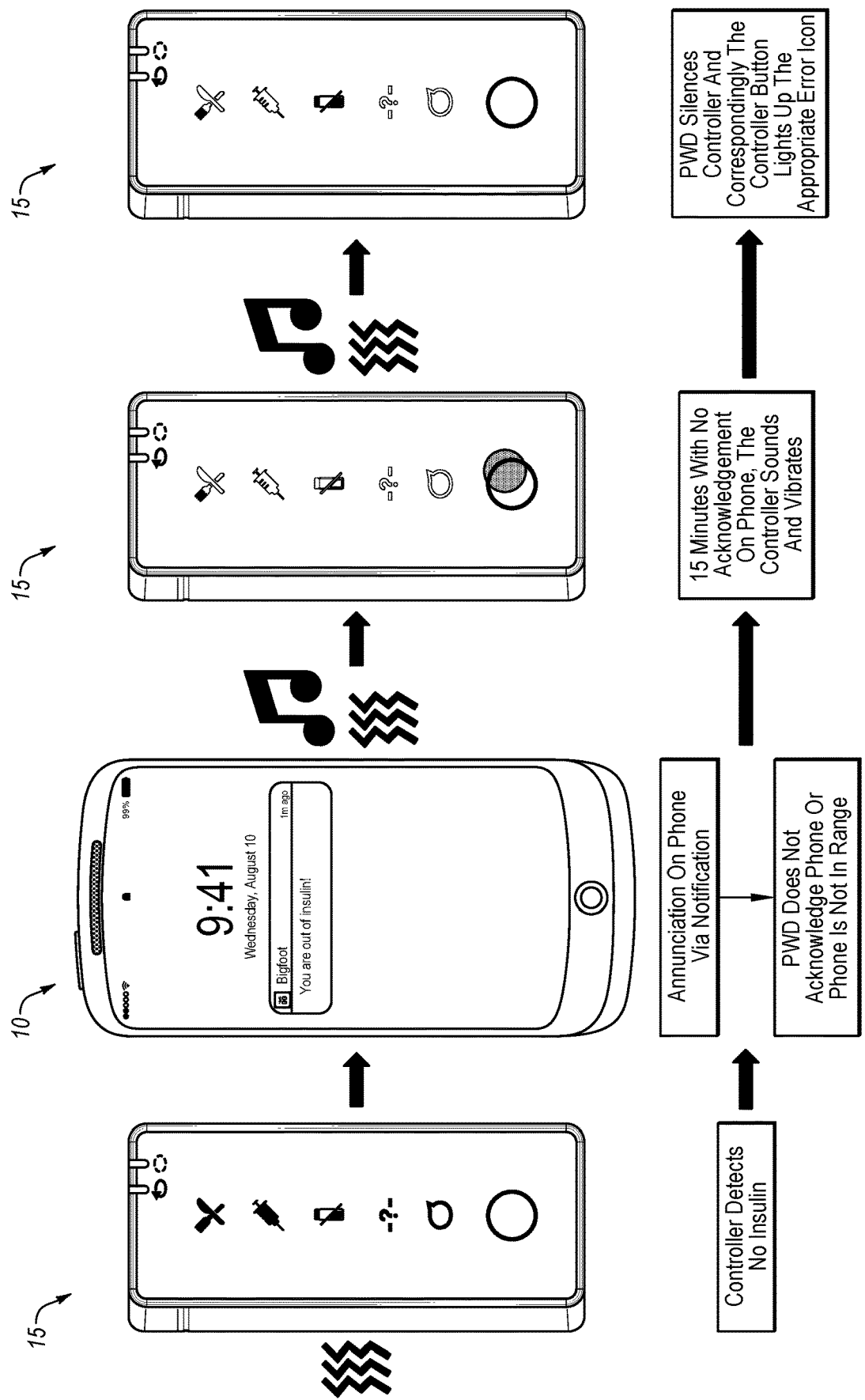
FIG. 9B depicts an example progression of alarm notifications for a lack of insulin flowing if the user fails to acknowledge the alarm condition within a predetermined period of time.

FIG. 9B depicts an example progression of alarm notifications for a lack of insulin flowing if the user fails to acknowledge the alarm condition within a predetermined period of time. This may be due to the smartphone being out of battery, left at home, or having settings on the smartphone that do not allow alarms to be announced. Regardless, if the medication delivery device 15 fails to receive an acknowledgement within a predetermined period of time, which may depend on the type of alarm condition, the medication delivery device can start to vibrate and sound an alarm tone, until the user presses the button to quiet the alarm sound and/or vibration, upon which an icon 243 will illuminate to tell the user that the alarm condition relates to the supply of insulin. In such a situation, an experienced user of the system may know to check to see if there is insulin remaining in the medication delivery device and/or to change out the insulin cartridge for a new cartridge and/or to check for occlusions. In some cases, a user will know to retrieve the remote user-interface device for help in determining how to resolve the alarm condition. After a predetermined period of time (e.g., between 5 seconds and 30 seconds) illuminated icon 243 may be turned off, but the user can again press the button to check the status of the medication delivery device. Additionally of note, neither of the mode lights 236 or 237 is illuminated, indicating that insulin is not being delivered. The alarm on the pump can have a greater duration and/or volume than any sound/vibration made on pump when pump first sends the wireless communication to the smartphone.

While FIGS. 9A-14B illustrate a smartphone as the remote user-interface device, it will be appreciated that any device with any notification scheme with locked devices, unlocked devices, messaging technologies, etc., are contemplated within the scope of the present disclosure. For example, the same approach may be used with ANDROID® devices, iPHONES®, other smartphones, music-playing devices such as an iPOD®, tablet computers, etc.

Figure 10A:
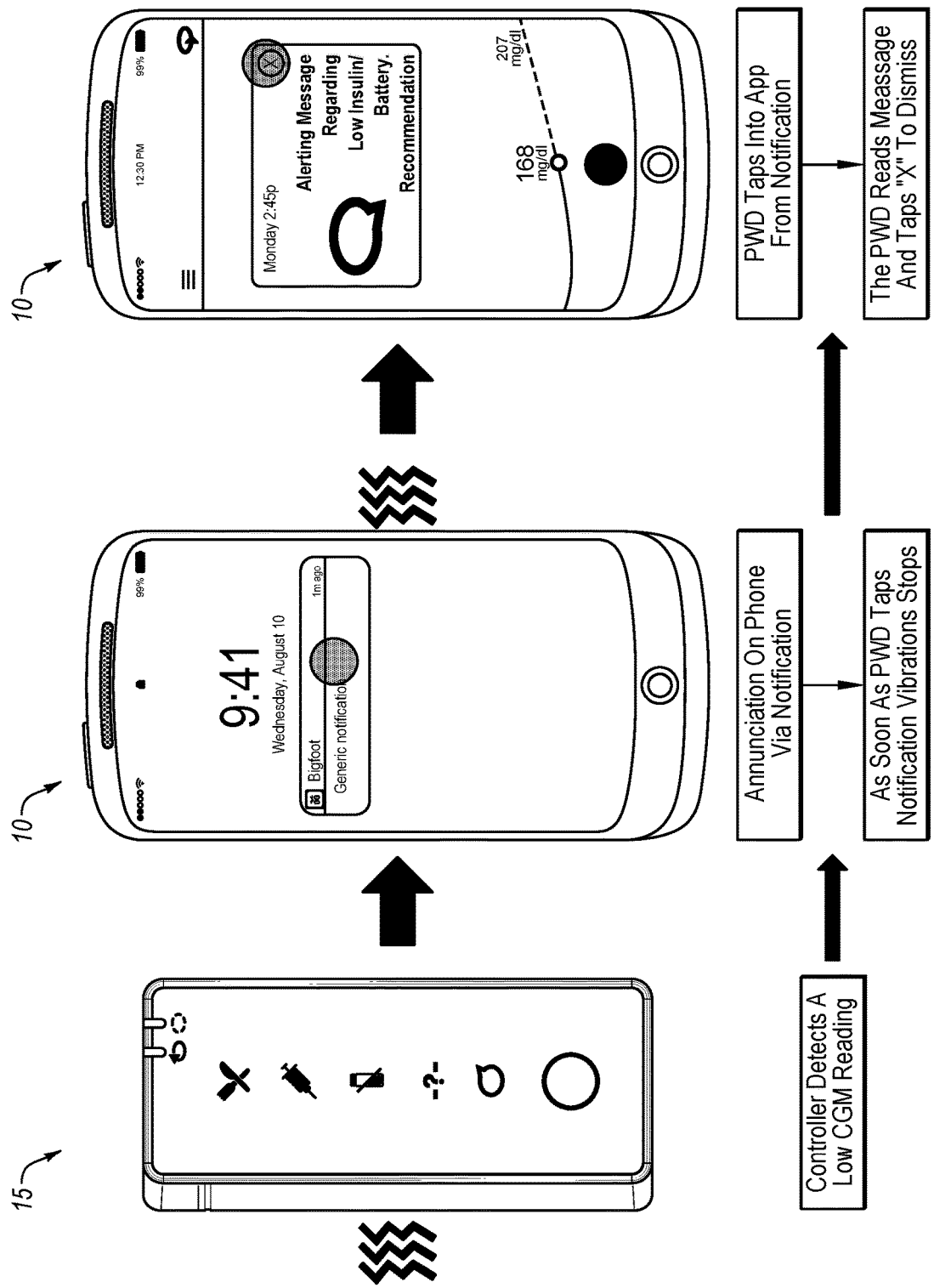
FIG. 10A depicts an example progression of an alert notification regarding battery or insulin levels if the user acknowledges the alert condition within a predetermined period of time.
Figure 10B:
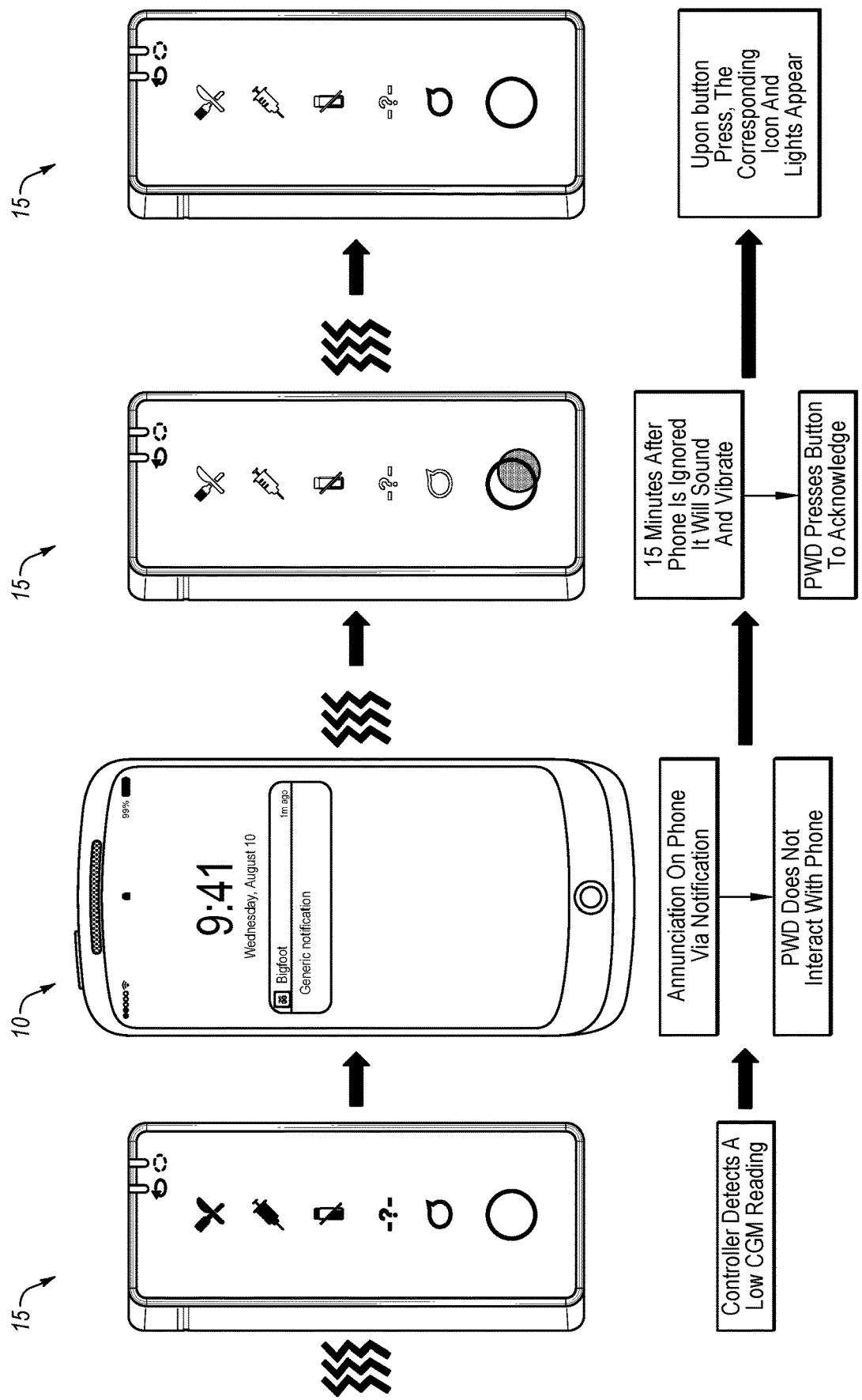
FIG. 10B depicts an example progression of an alert notification regarding battery or insulin levels if the user fails to acknowledge the alarm condition within a predetermined period of time.

FIG. 10A depicts an example progression of an alert notification regarding battery or insulin levels if the user acknowledges the alert condition within a predetermined period of time. FIG. 10B depicts an example progression of an alert notification regarding battery or insulin levels if the user fails to acknowledge the alarm condition within a predetermined period of time. These progressions are similar to that depicted in FIGS. 9A and 9B for an alarm, but involve an alert message, thus the message icon 245 illuminates, with the automation mode indicator light 236 still illuminated if the alarm is snoozed on the medication delivery device or the status is checked. As noted above, the icon displayed for the alert message on the remote user-interface device matches the icon illuminated on the medication delivery device.

Figure 11A:
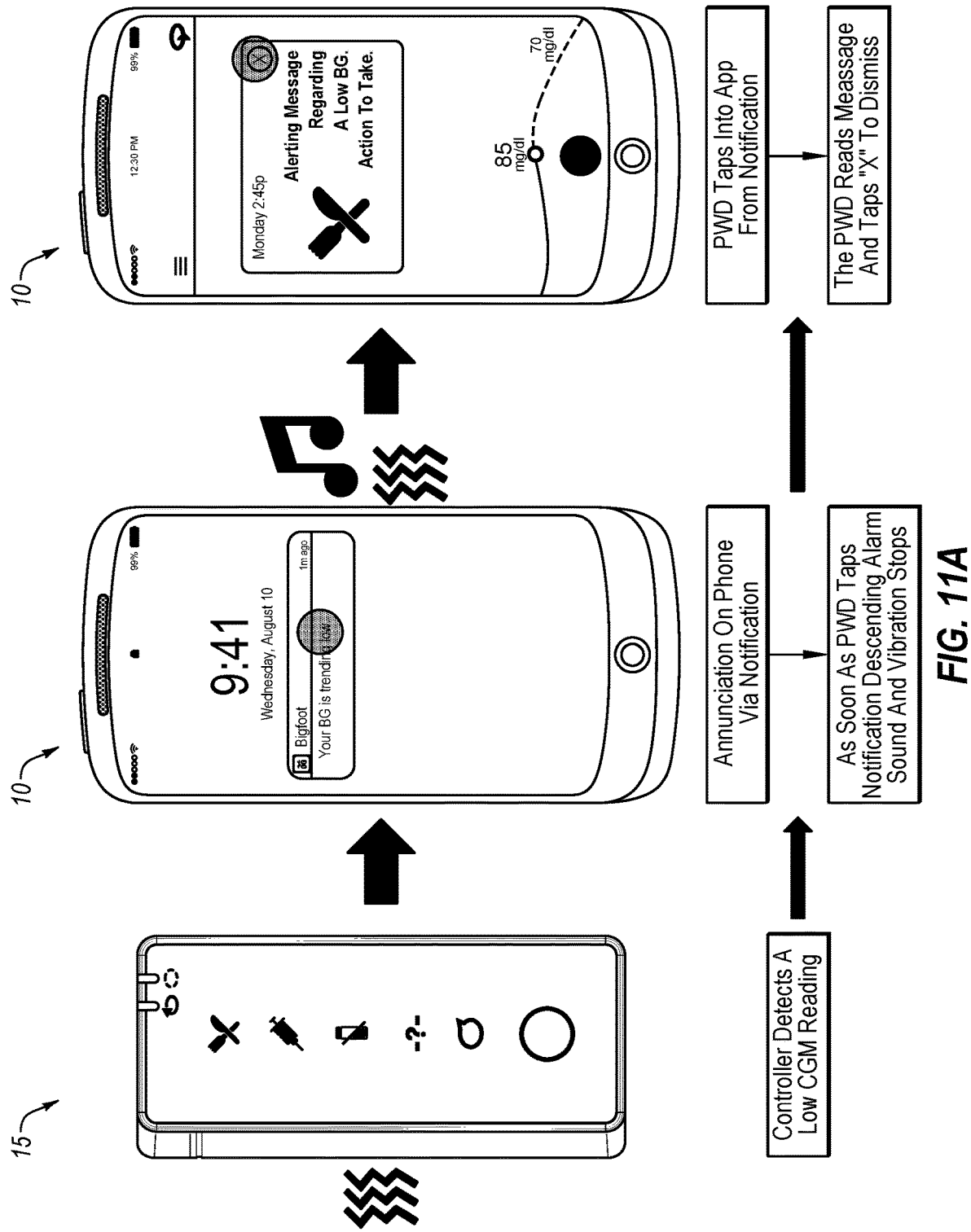
FIG. 11A depicts an example progression of an alert notification regarding a first blood glucose event if the user acknowledges the alert condition within a predetermined period of time.
Figure 11B:
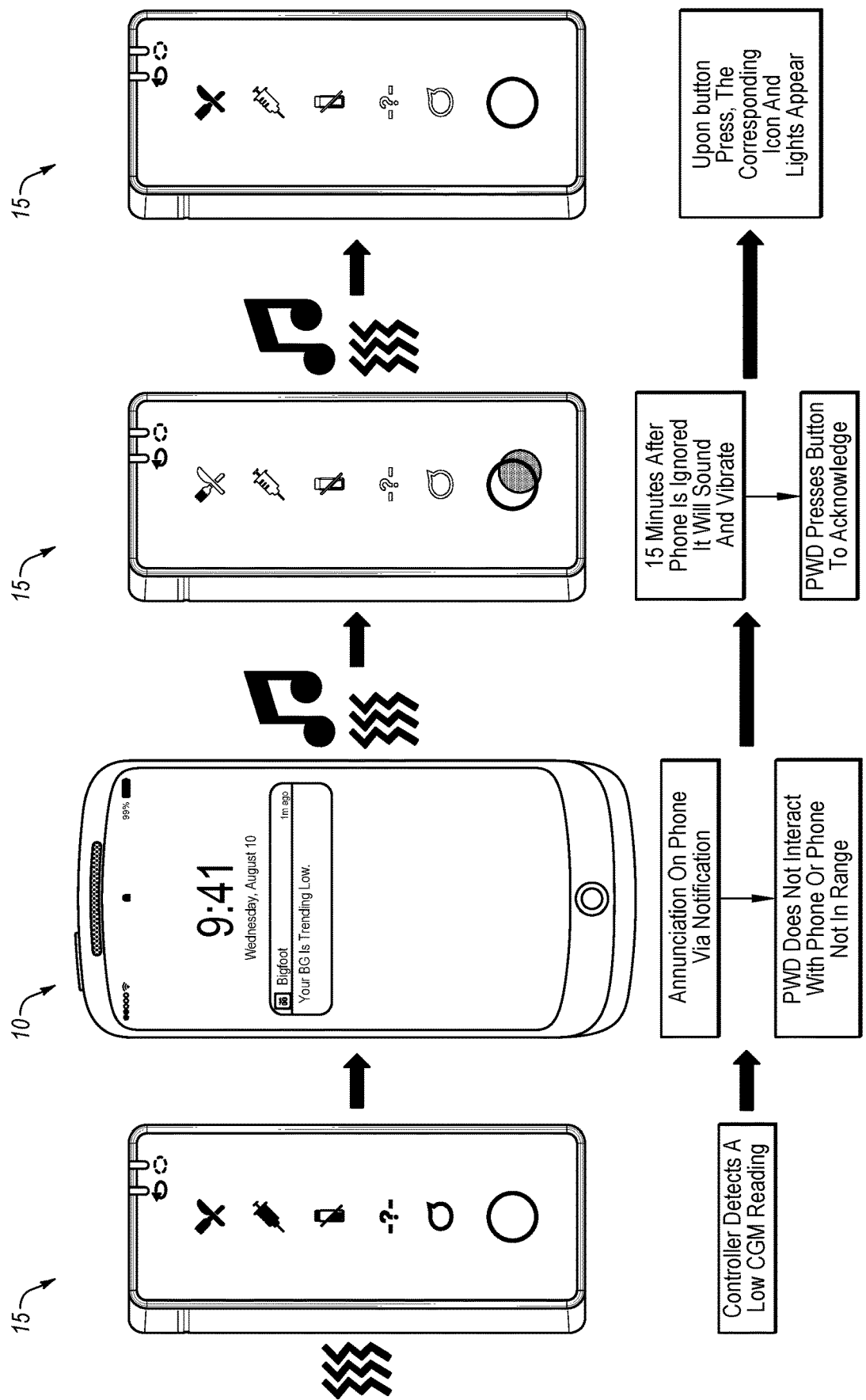
FIG. 11B depicts an example progression of an alert notification regarding a first blood glucose event if the user fails to acknowledge the alarm condition within a predetermined period of time.

FIG. 11A depicts an example progression of an alert notification regarding a first blood glucose event if the user acknowledges the alert condition within a predetermined period of time. FIG. 11B depicts an example progression of an alert notification regarding a first blood glucose event if the user fails to acknowledge the alarm condition within a predetermined period of time. FIGS. 11A and 11B involve an alert regarding a predicted low glucose event that indicates that the user should consume carbohydrates in order to avoid a hypoglycemic condition. Any suitable predictive technique can be used to trigger this alert, which may escalate to an alarm condition if the user reaches a hypoglycemia threshold. The illuminable icon 241 indicating a need to eat on the medication delivery device is again reinforced on the remote user-interface device by using the same icon in the message.

Figure 12A:
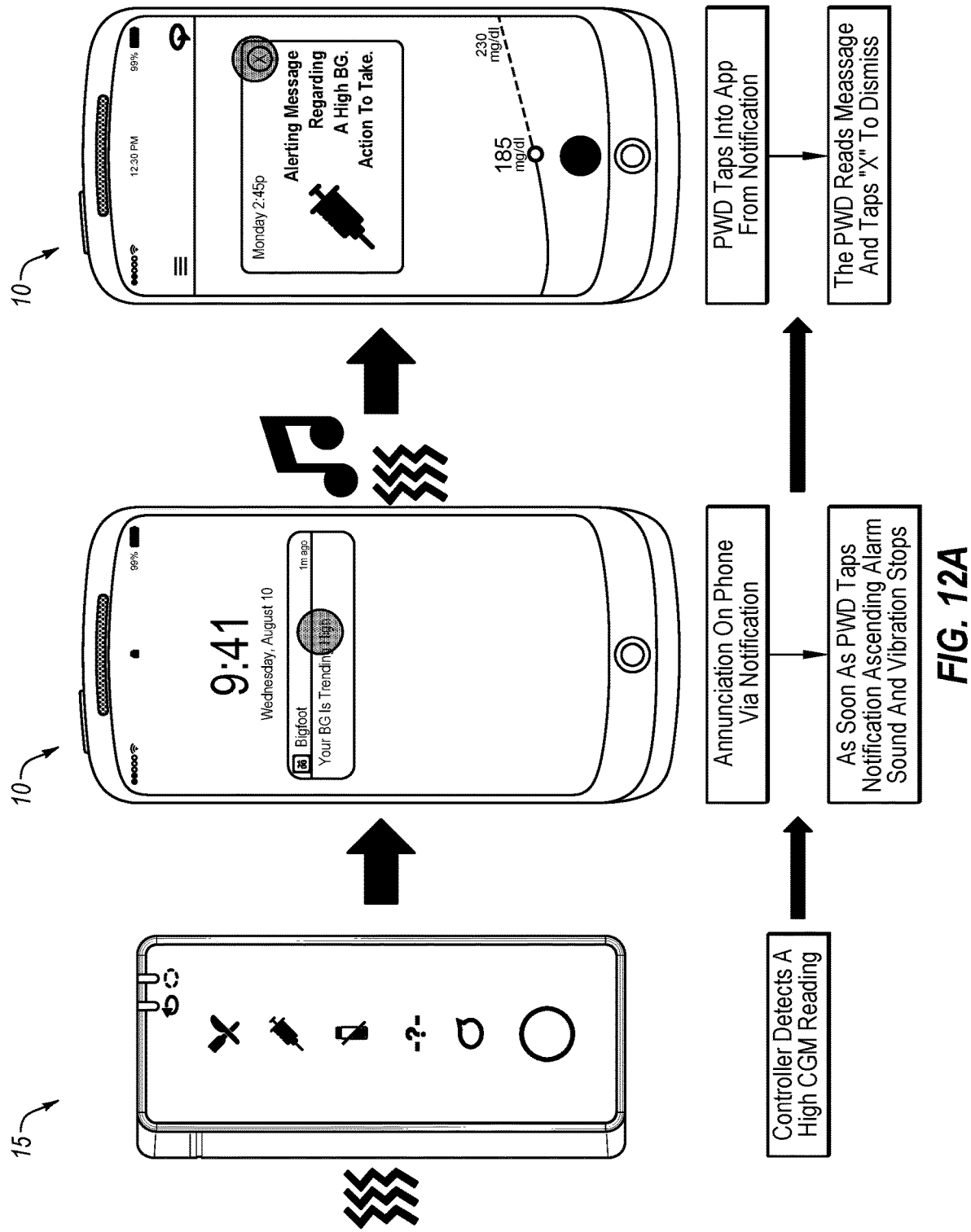
FIG. 12A depicts an example progression of an alert notification regarding a second blood glucose event if the user acknowledges the alert condition within a predetermined period of time.
Figure 12B:
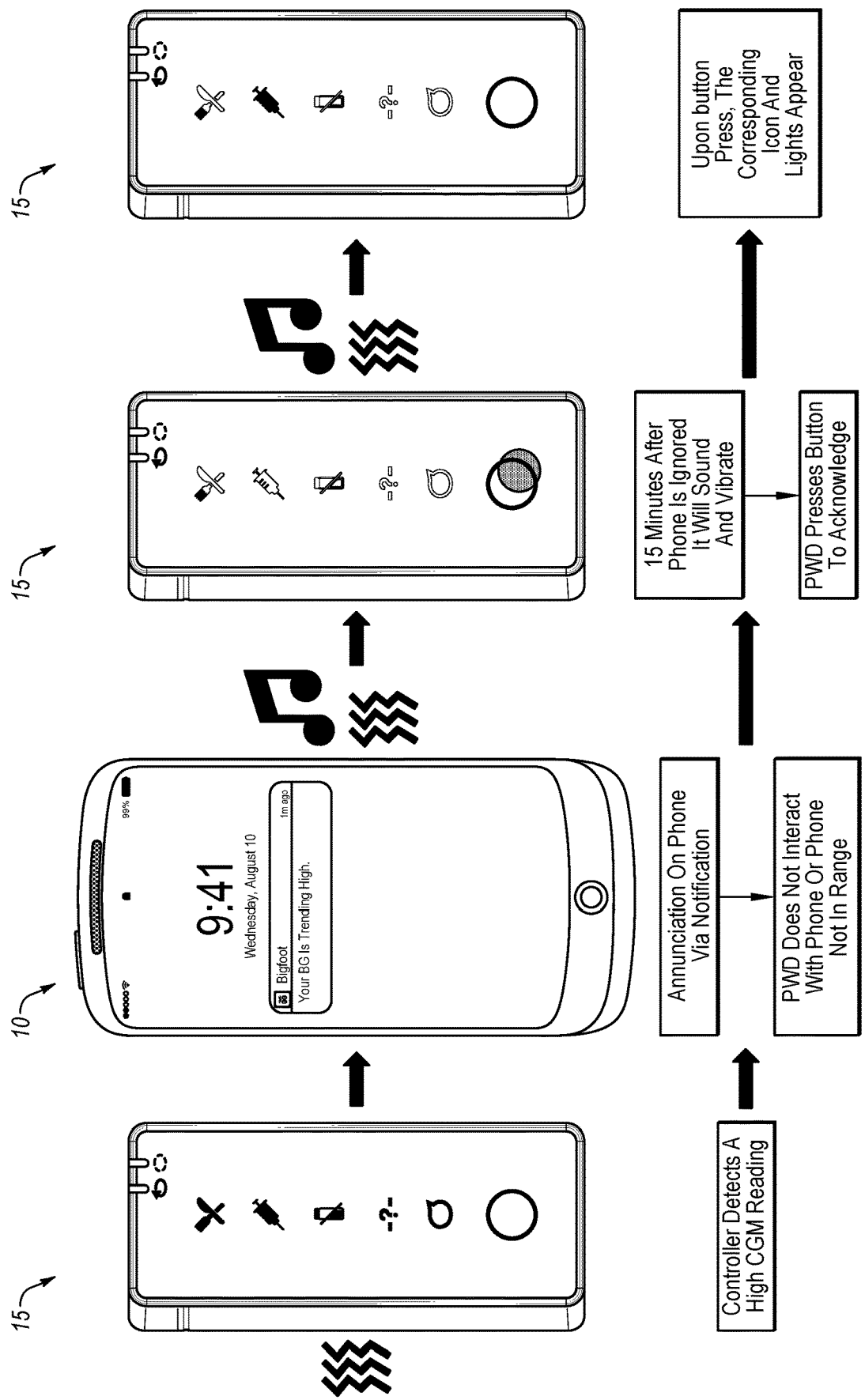
FIG. 12B depicts an example progression of an alert notification regarding a second blood glucose event if the user fails to acknowledge the alarm condition within a predetermined period of time.

FIG. 12A depicts an example progression of an alert notification regarding a second blood glucose event if the user acknowledges the alert condition within a predetermined period of time. FIG. 12B depicts an example progression of an alert notification regarding a second blood glucose event if the user fails to acknowledge the alarm condition within a predetermined period of time. FIGS. 12A and 12B involve an alert condition where the user is predicted to reach and/or stay in a hypoglycemic state without a corrective dose of insulin. In some cases, this alert condition can consider whether the user has announced and/or bolused for a meal. In some cases, this alert condition may be triggered if a meal is consumed and the user neglected to announce or bolus for the meal. Insulin injection icon 242 can indicate the need for the user to administer a bolus of insulin, and again the use of the same icon on the remote user-interface device 10 can reinforce the types of actions the user should take when seeing the icon when the remote user-interface device is not available.

Figure 13A:
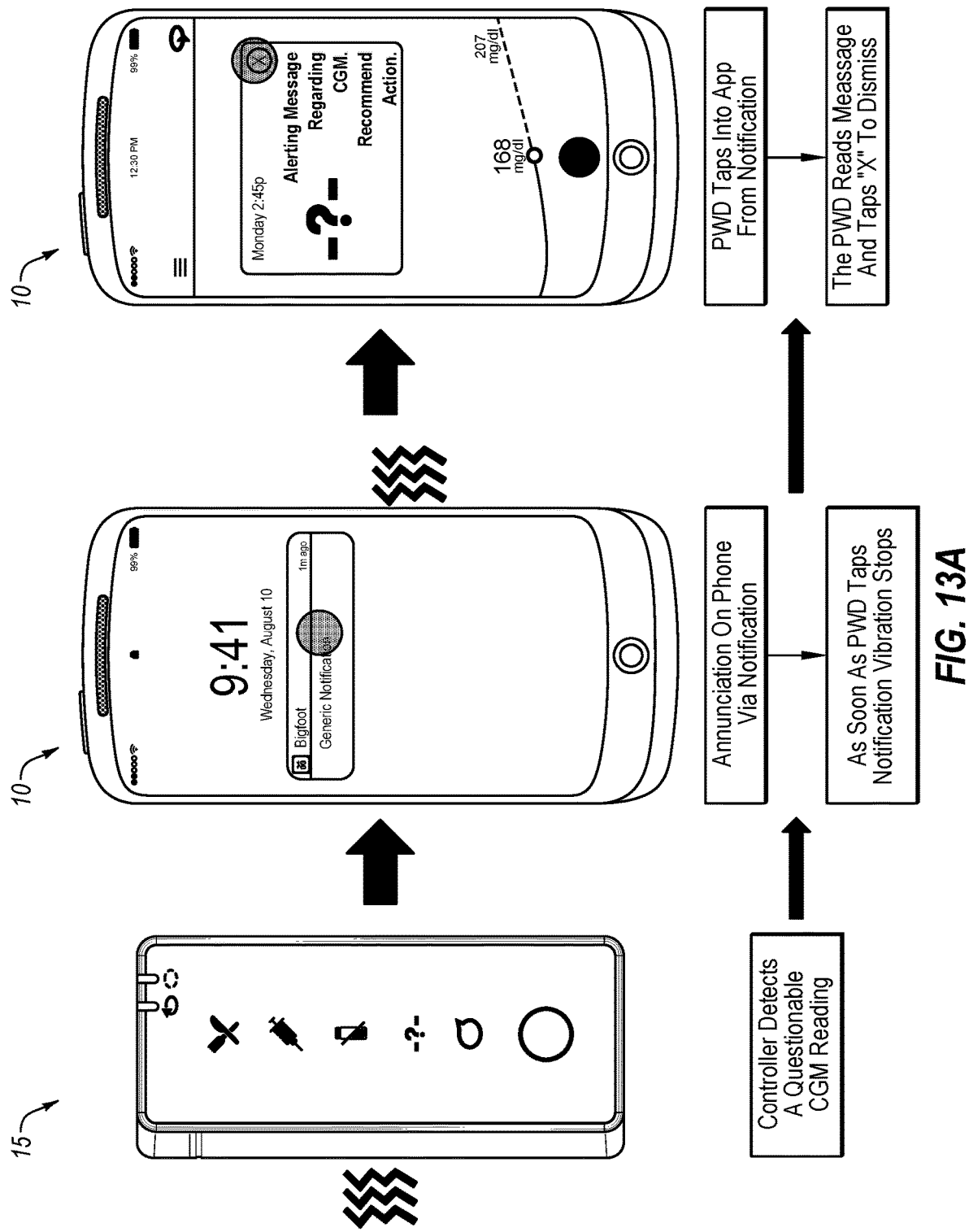
FIG. 13A depicts an example progression of an alert notification regarding a CGM event if the user acknowledges the alert condition within a predetermined period of time.

FIG. 13A depicts an example progression of an alert notification regarding a CGM event if the user acknowledges the alert condition within a predetermined period of time.

Figure 13B:
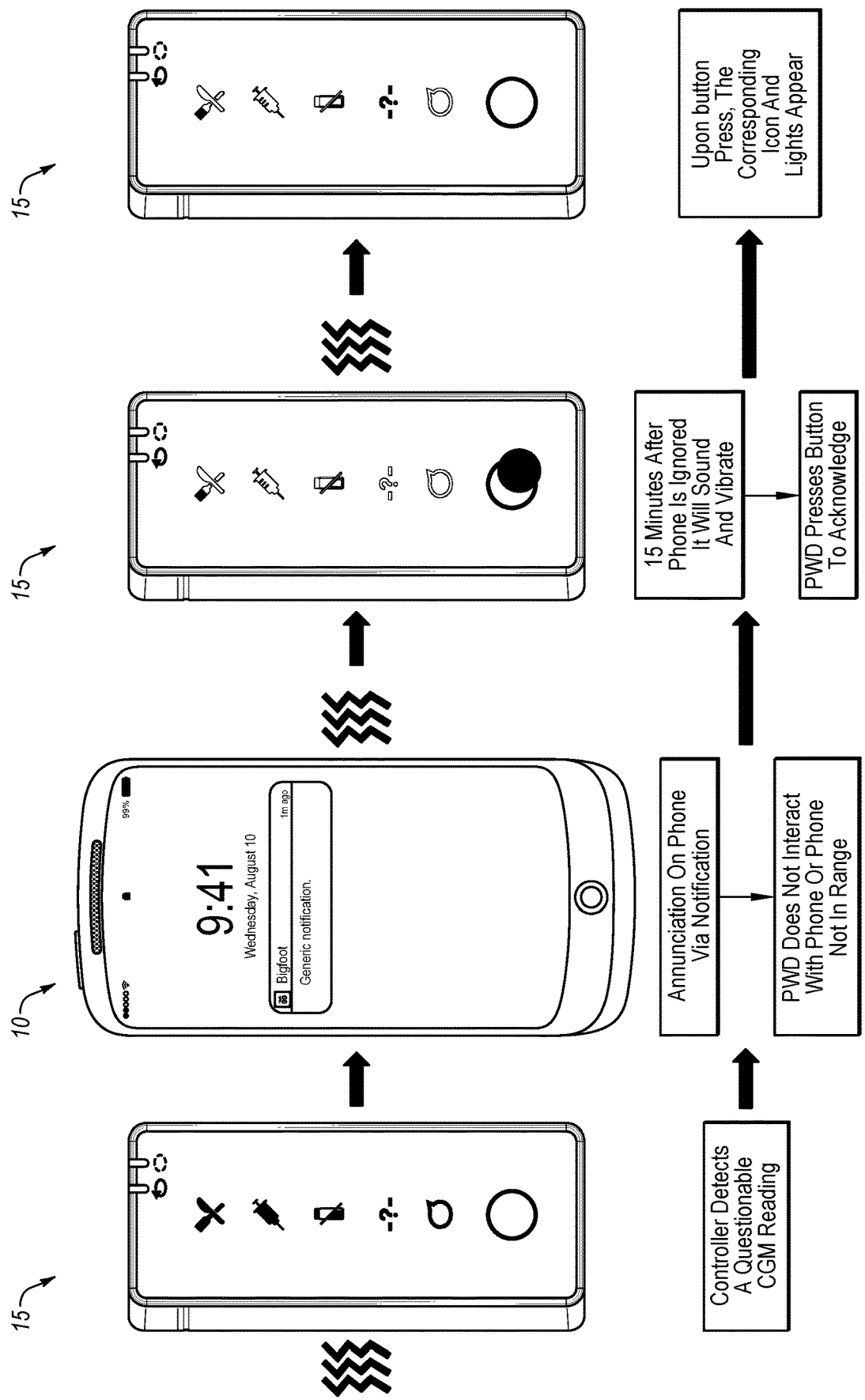
FIG. 13B depicts an example progression of an alert notification regarding a CGM event if the user fails to acknowledge the alarm condition within a predetermined period of time.

FIG. 13B depicts an example progression of an alert notification regarding a CGM event if the user fails to acknowledge the alarm condition within a predetermined period of time. The -?- icon 244 can indicate that the CGM is providing questionable or nonexistent data. In some cases, other icons, such as a triple question mark, can be used to indicate that the CGM is providing unreliable data. Again, the meaning of icon 244 is reinforced by the use of the same icon on the remote user-interface device.

Figure 14A:
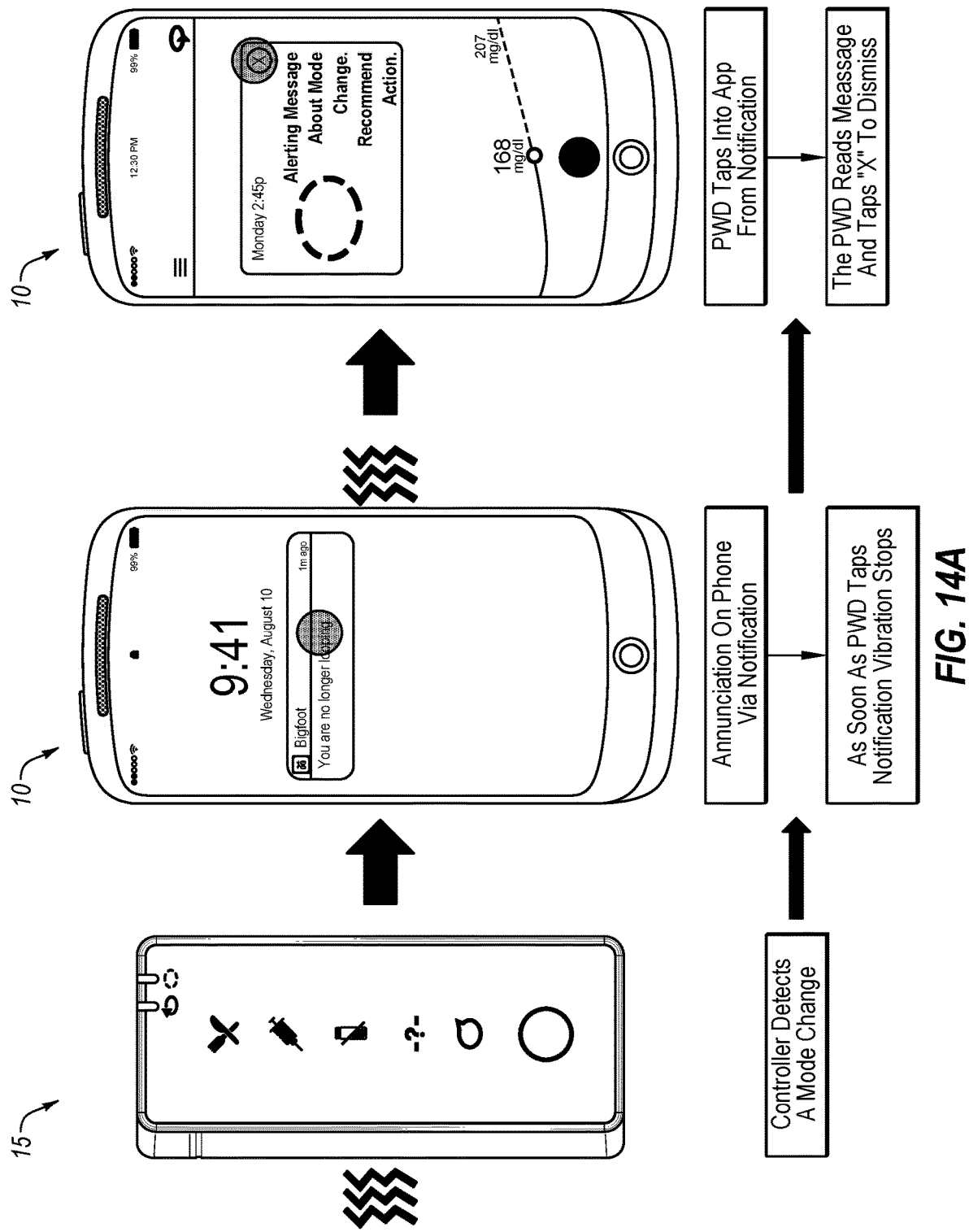
FIG. 14A depicts an example progression of an alert notification regarding a mode change event if the user acknowledges the alert condition within a predetermined period of time.
Figure 14B:
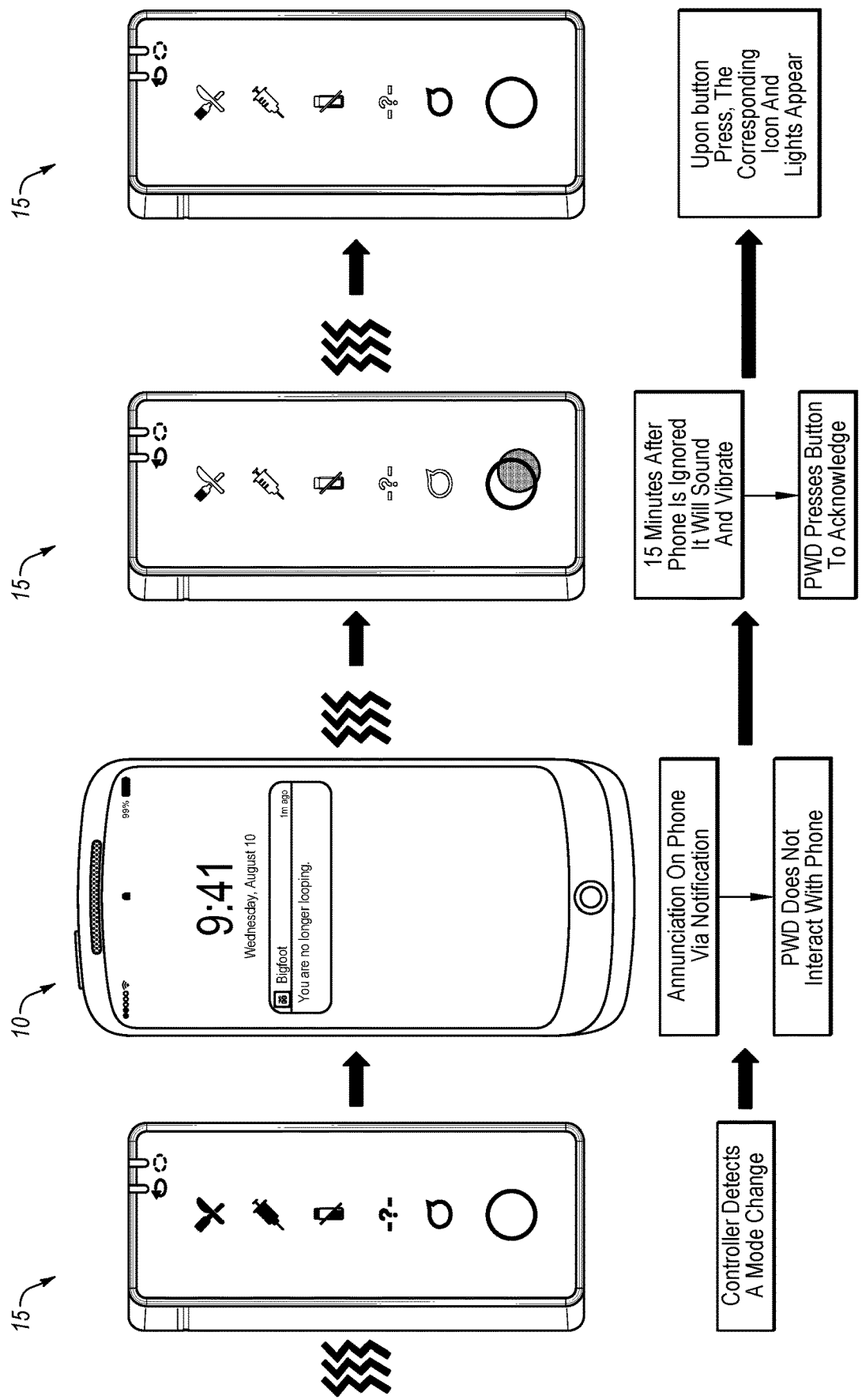
FIG. 14B depicts an example progression of an alert notification regarding a mode change event if the user fails to acknowledge the alarm condition within a predetermined period of time.

FIG. 14A depicts an example progression of an alert notification regarding a mode change event if the user acknowledges the alert condition within a predetermined period of time. FIG. 14B depicts an example progression of an alert notification regarding a mode change event if the user fails to acknowledge the alarm condition within a predetermined period of time. As shown, message icon 245 is issued along with a change of the mode indicator lights to indicate the current mode.

In some cases, alarms may be accompanied by audible alarms (optionally with haptic feedback) while alerts are accompanied by only haptic feedback. As shown in FIGS. 9-14, medication delivery devices can provide some haptic feedback when they send a wireless communication about an alarm or alert condition to a remote user-interface device, which can help a user understand that an alarm or alert coming from the remote user-interface device is coming from the medication delivery device.

In some cases, mode indicator lights 236 and 237 can be positioned along a top surface of the medication delivery device so that a user having the medication delivery device in their pocket can quickly check to ensure that the system is in automated mode without fully removing the medication delivery device from the user's pocket. It is envisioned that these lights will be the most frequently checked, as it will confirm that the medication delivery device is operational, delivering insulin, and indicate the current mode, while other message, alarms, and alerts can be readily evaluated using a remote user-interface device. Additionally or alternatively, any of the lights or icons may be placed at any location on the surface of the medication delivery device to facilitate observation of the icons or lights. The location and arrangement of the various icons and/or lights may be arranged based on any number of factors, including importance to user safety, frequency of use, etc.

Although FIGS. 2-14 depict a certain configuration and use of notification lights, other light configurations and signaling techniques are also envisioned. For example, FIGS. 15A-15C symbolically illustrate how an example pair of notification lights on an automated medication infusion pump can inform a user about the status of the medication delivery system, even without access to the remote user-interface device 10. By pushing a button on or double tapping on the housing of medication delivery device 15 or 15' will illuminate medication delivery indicator light 232 if insulin is being delivered. In some cases, medication delivery indicator light 232 can display different colors to indicate a mode of insulin delivery. In some cases, medication delivery indicator light 232 can remain continuously illuminated or blink to indicate a mode of insulin delivery. In some cases, medication delivery indicator light 232 can display different colors or blink using a different frequency to indicate whether real-time analyte sensor data is being received by medication delivery device 15 or 15'. Message indicator light 234 can be included on medication delivery device 15 or 15' to provide lights indicative of whether there is a message for the user available on remote user-interface device 60. In some cases, the urgency of the message can be conveyed by the color of message indicator light 234 and/or whether message indicator light 234 is blinking. For example, in some cases, message indicator light 234 can be yellow to indicate that a medication delivery device or analyte sensor maintenance activity is due within the next 3 hours. In some cases, message indicator light 234 can illuminate red to indicate that the system requires immediate maintenance and/or that the user has a high or low blood glucose reading. FIG. 15B symbolically illustrates a situation where the analyte sensor and/or the medication delivery device vibrates to indicate the change in mode and/or the presence of a message. As shown, after the vibration pattern, the user can tap the device using a tap pattern (such as a double tap) to stop the vibration and trigger the illumination of indicator lights 232 and 234. In some cases, the vibration will repeat until the user stops the alarm with a tap pattern, which in some cases may be required to match the vibration pattern within a predetermined margin of error. For example, FIGS. 16A and 16B illustrate example alarms and how a user can snooze the alarm or alarms by matching a vibration pattern and/or an alarm pattern (e.g., an alarm pattern of musical notes) with a tap pattern.

As shown in FIG. 15B, medication delivery indicator light 232 is blinking to indicate that the system is not automating medication delivery and message indicator light 234 is yellow to indicate that a message is waiting for the user on the remote user-interface device 10. For example, the message could be a message that the system has entered a non-automated mode because of a loss of analyte sensor data reaching the medication delivery device.

Methods, systems, and devices provided herein can additionally supply an audible alarm or alert to the analyte sensor and/or the medication delivery device (instead of or with vibration) to indicate that the system requires immediate attention. For example, an audible alarm could be triggered if there is an occlusion, if the user has a high or low analyte sensor data point, if the medication delivery device is out of insulin or is expected to be out of insulin in the next hour. FIG. 15C symbolically illustrates a situation where the analyte sensor and/or the medication delivery device vibrates and issues an audible alarm to indicate the need for immediate user interaction with the system. As shown, after the vibration and alarm sound, the user can tap the device using a tap pattern (such as a double tap) to temporarily quiet the vibration and alarm sound and trigger the illumination of indicator lights 232 and 234. In some cases, the tapping will not quiet the alarm if the alarm is more urgent. As shown in FIG. 15C, medication delivery indicator light 232 is off to indicate that the system is not delivering insulin and message indicator light 234 is red to indicate that the system requires immediate attention. In this situation, the user will know that they need to immediately find their remote user-interface device and/or take over responsibility to manage their blood glucose values. In some cases, if the user is unable to find their remote user-interface device, the user will know to check their blood glucose level (e.g., with a blood glucose meter) and find insulin from another source if additional insulin is needed.

Further example embodiments are listed below.

Embodiment 1: An on-body networked medication-delivery system comprising: an analyte sensor adapted to generate analyte data for a user and wirelessly transmit the analyte data; a medication delivery device in wireless communication with the analyte sensor, the medication delivery device comprising: a medication reservoir or a space to receive a medication reservoir; a drive system adapted to meter the administration of medication out of the medication delivery device; a feature to provide audible, visual, or haptic feedback to a user; a controller adapted to change a dosage of medication based at least in part on the analyte sensor data and adapted to issue alarm and alert wireless communications based on a detection of an alarm or alert condition; and a tap detector or button adapted to permit the user to check the status of the medication delivery device or to acknowledge alert or alarm conditions; and a remote user-interface device in wireless communication with the medication delivery device, the remote user-interface device being adapted to receive the alarm and alert wireless communications from the controller and provide an audible, visual, or haptic alarm or alert message to the user and permit the user to acknowledge an associated alarm or alert condition, the remote user-interface device being adapted to wirelessly communicate each acknowledgement to the controller, wherein the controller is adapted to trigger an audible, visual, or haptic alarm or alert message via a feature to provide audible, visual, or haptic feedback if the controller fails to receive an acknowledgement of the alert or alarm condition within a predetermined period of time after the controller issues the alarm and alert wireless communication.

Embodiment 2: The system of Embodiment 1, wherein the system is a diabetes management system, the medication delivery device is an insulin pump, and the analyte sensor is a continuous glucose monitor.

Embodiment 3: The system of Embodiment 1 or Embodiment 2, wherein the medication delivery device is a patch pump.

Embodiment 4: The system of one of Embodiments 1-3, wherein the medication delivery device comprises a durable controller and a disposable pump body, each having a housing and being removably connectable, the disposable pump body comprising at least the medication reservoir or a space to receive a medication reservoir and the durable controller comprising at least the feature(s) to provide audible, visual, or haptic feedback, the controller, and the tap detector or button.

Embodiment 5: The system of one of Embodiments 1-4, wherein the medication delivery device comprise a button.

Embodiment 6: The system of one of Embodiments 1-5, wherein the feature(s) to provide audible, visual, or haptic feedback to a user comprises at least one light associated with an icon.

Embodiment 7: The system of Embodiment 6, wherein the remote user-interface device is adapted to present the icon for an alarm or alert condition.

Embodiment 8: The system of Embodiment 7, wherein the at least one light associated with the icon does not illuminate on the housing until the tap detector detects a tap, or the button is pressed, or until the predetermined period of time.

Embodiment 9: The system of one of Embodiments 1-8, wherein a user can acknowledge an audible, visual, or haptic alarm or alert message provided by a remote user-interface device by tapping the medication delivery device or pressing the button on the medication delivery device even before the medication delivery device triggers the audible, visual, or haptic alarm or alert message via the feature(s) to provide audible, visual, or haptic feedback.

Embodiment 10: The system of one of Embodiments 1-9, wherein the feature(s) to provide audible, visual, or haptic feedback comprises a vibration motor adapted to provide haptic feedback, wherein the controller is adapted to provide haptic feedback or audible feedback, upon issuing the alarm and alert wireless communications, wherein the audible alarm or alert message triggered if the controller fails to receive an acknowledgement of the alert or alarm condition within a predetermined period of time is louder or longer in duration than the haptic feedback or audible feedback provided when the controller issues the alarm and alert wireless communications.

Embodiment 11: The system of one of Embodiments 1-10, wherein the predetermined period of time is at least 30 seconds and no greater than 1 hour, between 1 minute and 30 minutes, between 3 minutes and 20 minutes, or between 5 minutes and 15 minutes, wherein the predetermined period of time for an alarm or alert condition can depend on the alarm or alert condition.

Embodiment 12: The system of one of Embodiments 1-11, wherein an acknowledgement of an alarm or alert will quiet audible or haptic feedback for the alarm or alert condition for a predetermined snooze period of time, wherein the controller is adapted to issue new alarm and alert wireless communications after the predetermined snooze period of time if the alarm or alert condition is still detected as being present.

Embodiment 13: The system of one of Embodiments 1-12, wherein the remote user-interface device is adapted to present the user with troubleshooting instructions using text, audio, or video to remove the alarm or alert condition, wherein the medication delivery device does not present any troubleshooting instructions using text, audio, or video.

Embodiment 14: The system of one of Embodiments 1-13, wherein the medication delivery device comprises a housing that contains a non-rechargeable, non-replaceable battery.

Embodiment 15: The system of one of Embodiments 1-4, wherein the remote user-interface device is adapted to allow a user to send instructions to the medication delivery device using the remote user-interface device, wherein the remote user-interface device can prompt the user to confirm the instructions by pressing the button or tapping the controller under certain conditions.

Embodiment 16: The system of Embodiment 15, wherein the controller is adapted to require a user to confirm a bolus delivery by pressing the button or tapping the controller if the dosage is determined by the controller to be unusual based on typical dosage amounts administered by the user, based on the timing the dosage or the timing of a previous dosage, or based on a prediction of how the dosage will change analyte levels for the user.

Embodiment 17: The system of one of Embodiments 1-16, wherein the medication delivery device comprises one or more icons, and one or more lights associated with those one or more icons, indicating whether the medication is being delivered based on the analyte sensor or not or whether there is an error with the analyte sensor.

Embodiment 18: The system of one of Embodiments 1-17, wherein the medication delivery device comprises one or more icons, and one or more lights associated with those one or more icons, indicating that an amount of medication in the medication delivery device is below a threshold level.

Embodiment 19: The system of one of Embodiments 1-18, wherein the medication delivery device comprises one or more icons, and one or more lights associated with those one or more icons, indicating that the user should administer more medication or consume carbohydrates.

Embodiment 20: The system of one of Embodiments 1-19, wherein the medication delivery device comprises one or more icons, and one or more lights associated with those one or more icons, indicating that a more detailed message for the user is awaiting the user on the remote user-interface device.

Embodiment 21: A method for issuing alarms and alerts in an on-body networked diabetes management system, the method comprising: receiving glucose sensor data from a continuous glucose monitor; determining a dosage of insulin delivery based at least in part on the glucose sensor data; detecting an alarm or alert condition; sending a wireless communication regarding the alarm or alert condition to a remote user-interface device; triggering an audible, visual, or haptic alarm or alert on the insulin delivery device if the insulin delivery device does not receive an acknowledgement of the alarm or alert condition within a predetermined period of time.

Embodiment 22: The method of Embodiment 21, wherein the user can acknowledge the alarm by pressing a button on the insulin delivery device or by tapping the insulin delivery device and by interacting with the remote user-interface device, wherein the insulin delivery device can receive an acknowledgement of the alarm or alert condition as part of a wireless communication from the remote user-interface device.

Embodiment 23: The method of Embodiment 21 or Embodiment 22, further comprising triggering audible or haptic feedback of the insulin delivery device when sending the wireless communication regarding the alarm or alert condition to the remote user-interface device, wherein the audible, visual, or haptic alarm or alert on the insulin delivery device after the predetermined period of time is louder or longer in duration than the feedback initiated when sending the wireless communication.

Embodiment 24: The method of one of Embodiments 21-23, further comprising stopping the audible, visual, or haptic alarm or alert on the insulin delivery device when a button on the insulin delivery device is pressed.

Embodiment 25: The method of Embodiment 24, wherein the button must be pressed at least twice during a predetermined period of time or according to a predetermined pattern for the audible, visual, or haptic alarm or alert to be stopped.

Embodiment 26: The method of Embodiment 24 or 25, wherein stopping the audible, visual, or haptic alarm or alert on the insulin delivery device prevents the triggering of any audible, visual, or haptic alarms or alerts regarding that alarm or alert condition or the sending of any wireless communication regarding the alarm or alert condition for a predetermined period of time, wherein the process of Embodiment 21 will repeat after the predetermined period of time if the alarm or alert condition is present after the predetermined period of time.

Embodiment 27: The method of one of Embodiments 21-26, wherein the alarm or alert condition is an indication of a change from a first mode of operation to a second mode of operation.

Embodiment 28: The method of one of Embodiments 21-26, wherein the alarm or alert condition is an indication of an amount insulin remaining in the insulin delivery device being below a threshold level.

Embodiment 29: The method of one of Embodiments 21-26, wherein the alarm or alert condition is an indication of a low glucose condition or a high glucose condition.

Embodiment 30: The method of Embodiment 29, wherein the audible, visual, haptic alarm or alert on the insulin delivery device includes the illumination of an icon or next to an icon indicating that the user should eat or should administer insulin.

Embodiment 31: The method of one of Embodiments 21-26, wherein the alarm or alert condition is a notice that the continuous glucose monitor is not working, not in range, or not reliable.

Embodiment 32: The method of one of Embodiments 21-26, wherein the alarm or alert condition is a notice about a possible occlusion, a possible air bubble, a possible missed meal announcement, a possible need to change an infusion set, a possible need to calibrate a CGM, a possible need to replace the CGM, or a possible need to check ketone levels, wherein the audible, visual, haptic alarm or alert on the insulin delivery device includes the illumination of an icon or next to an icon indicating that the user should check the remote user-interface device for information about the alert.

Embodiment 33: An insulin delivery device adapted for wireless communication with a continuous glucose monitor and a remote user-interface device, the insulin delivery device comprising: an insulin reservoir or a space to receive an insulin reservoir; a drive system adapted to meter the administration of insulin out of the insulin delivery device; a wireless transmitter and receiver adapted to send and receive wireless communications from at least a continuous glucose monitor and a remote user-interface device; a controller adapted to change a dosage of medication based at least in part on data from the continuous glucose monitor and adapted to issue alarm and alert wireless communications based on a detection of an alarm or alert condition; a housing containing at least the controller and the wireless transmitter and receiver; a tap detector within the housing or a button on the housing adapted to permit the user to check the status of the insulin delivery device or to acknowledge alert or alarm conditions; and one or more lights adapted to illuminate icons or adjacent to icons on the housing indicating a mode of operation of the insulin delivery device and whether insulin is being delivered to the user.

Embodiment 34: The device of Embodiment 33, further comprising one or more lights adapted to illuminate icons or adjacent to icons on the housing indicating that a message is awaiting the user on the remote user-interface device.

Embodiment 35: The device of Embodiment 33 or Embodiment 34, further comprising one or more lights adapted to illuminate icons or adjacent to icons on the housing indicating that the user has a blood glucose condition requiring the consumption of carbohydrates or the administration of additional insulin.

Embodiment 36: The device of Embodiment 35, wherein the user cannot administer additional insulin using the insulin delivery device without accessing the remote user-interface device.

Embodiment 37: The device of Embodiment 36, wherein the controller is adapted to evaluate whether a wireless communication from a remote user-interface device is within one or more predefined parameters.

Embodiment 38: The device of Embodiment 37, wherein the controller is adapted to send a wireless communication to the remote user-interface device indicating that a bolus is outside of one or more predefined parameters, or indicating the user must confirm the bolus on the insulin delivery device by tapping or pressing the button.

Embodiment 39: The device of one of Embodiments 33-38, further comprising one or more lights adapted to illuminate icons or adjacent to icons on the housing indicating that the insulin delivery device has less than a threshold amount of insulin remaining.

Embodiment 40: The device of one of Embodiments 33-39, further comprising one or more lights adapted to illuminate icons or adjacent to icons on the housing indicating that there is a problem with the data being received, or a lack of data being received, from the continuous glucose monitor.

Embodiment 41: A medication delivery system comprising a medication delivery device and a remote user-interface device, the medication delivery device and the remote user-interface device being in wireless communication, the medication delivery device being adapted to automatically administer medication according to programmed rate, a programmed schedule, or based on analyte sensor data without user input, the remote user-interface device being adapted to receive user commands for the medication delivery device to administer additional doses of medication, adjust the programmed delivery rate or schedule, or adjust an algorithm that determines a dosage based on the analyte sensor data, wherein both the remote user-interface device and the medication delivery device are adapted to provide audible, visual, or haptic feedback to issue an alarm or alert regarding the ability of the medication delivery device to deliver medication, wherein the medication delivery device is adapted to detect a condition that prevents the delivery of medication and is adapted to send an alarm wireless communication to the remote user-interface device regarding the condition, wherein the remote user-interface device issues an audible, visual, or haptic alarm when the alarm wireless communication is received and provides a feature for the user to acknowledge the alarm, wherein the remote user-interface device sends an acknowledgement wireless communication to the medication delivery device upon the user acknowledging the alarm, wherein the medication delivery device is adapted to issue an audible, visual, or haptic alarm after a predetermined period of time after the alarm wireless communication is sent unless the medication delivery device receives the acknowledgement wireless communication during the predetermined period of time.

Embodiment 42: The medication delivery system of Embodiment 41, wherein the medication delivery device includes a feature to receive a user's acknowledgement an audible, visual, or haptic alarm to silence the alarm.

Embodiment 43: The medication delivery system of Embodiment 41 or Embodiment 42, wherein the medication delivery device is an insulin infusion pump, wherein the medication is insulin, and wherein the remote user-interface device is a smartphone.

Embodiment 44: The medication delivery system of Embodiment 43, further comprising a continuous glucose monitor in wireless communication with the insulin infusion pump, wherein the insulin infusion pump delivers different amounts or rates of insulin based on glucose data from the continuous glucose monitor.

Embodiment 45: The medication delivery system of Embodiment 44, wherein the insulin infusion pump is not adapted to display specific concentrations of the glucose data, but is adapted to send glucose data wireless communications to the smartphone, wherein the smartphone is adapted to display specific concentrations of the glucose data.

Embodiment 46: The medication delivery system of Embodiment 45, wherein the insulin infusion pump is adapted to illuminate one or more icons, or a light next to one or more icons, that indicate that the user is in or expected to experience hypoglycemic state or a hyperglycemic state, that indicate that the user should administer more insulin, or that indicate that the user should consume food, wherein the light becomes illuminated when the insulin infusion pump issues an issue an audible, visual, or haptic alarm or when the user acknowledges the alarm on the insulin infusion pump.

Embodiment 47: The medication delivery system of one of Embodiments 43-46, wherein the insulin infusion pump is adapted to illuminate one or more icons, or a light next to one or more icons, that indicate that the user is in out of insulin, wherein the light becomes illuminated when the insulin infusion pump issues an issue an audible, visual, or haptic alarm or when the user acknowledges the alarm on the insulin infusion pump.

While certain embodiments have been described and shown in the accompanying drawings, such embodiments are merely illustrative and not restrictive of the scope of the disclosure, and this disclosure is not limited to the specific constructions and arrangements shown and described, since various other additions and modifications to, and deletions from, the described embodiments will be apparent to one of ordinary skill in the art. Thus, the scope of the disclosure is only limited by the literal language, and legal equivalents, of the claims that follow.

What is claimed is:

1. A networked medication-delivery system comprising:
   an analyte sensor adapted to generate analyte data for a user and transmit the analyte data;
   a medication delivery device in communication with the analyte sensor, the medication delivery device configured to receive a medication reservoir, the medication delivery device comprising:
      a drive system adapted to administer medication from the medication delivery device;
      a feedback feature configured to provide audible, visual, or haptic feedback to a user;
      a controller adapted to change a dosage of medication based at least in part on the analyte sensor data and adapted to issue alarm and alert communications based on a detection of an alarm or alert condition;
      a detector or button adapted to permit the user at least one of to check a status of the medication delivery device, or to acknowledge alert conditions, or to acknowledge alarm conditions; and
      a user interface comprising:
         an icon; and
         an indicator light associated with the icon; and
   a remote user-interface device in communication with the medication delivery device, the remote user-interface device being adapted to receive the alarm and alert communications from the controller and provide an audible, visual, or haptic alarm or alert message to the user and to permit the user to acknowledge an associated alarm or alert condition, the remote user-interface device being adapted to communicate each acknowledgement to the controller,
   wherein the medication delivery device is configured to indicate, via the icon and the indicator light of the user interface, that a message related to medication delivery is waiting at the remote user-interface device.

2. The networked medication-delivery system of claim 1, wherein the system is a diabetes management system, the medication delivery device is an insulin pump, and the analyte sensor is a continuous glucose monitor.

3. The networked medication-delivery system of claim 1, wherein the medication delivery device is a patch pump.

4. The networked medication-delivery system of claim 1, wherein the medication delivery device comprises a durable controller and a disposable pump body, each having a housing and being removably connectable, the disposable pump body comprising at least the medication reservoir or a space to receive a medication reservoir, and the durable controller comprising at least the feedback feature to provide audible, visual, or haptic feedback, the icon, the indicator light associated with the icon, the controller, and the detector or button.

5. The networked medication-delivery system of claim 1, wherein the controller is adapted to trigger the icon and the indicator light associated with the icon, or the audible, visual, or haptic alarm or alert message via the feedback feature to provide audible, visual, or haptic feedback if the controller fails to receive an acknowledgement of the alert or alarm condition within a predetermined period of time after the controller issues the alarm and alert communication.

6. The networked medication-delivery system of claim 1, wherein the feedback feature to provide audible, visual, or haptic feedback to a user comprises another light associated with another icon.

7. The networked medication-delivery system of claim 6, wherein the remote user-interface device is adapted to present the another icon for an alarm or alert condition.

8. The networked medication-delivery system of claim 7, wherein the another light associated with the another icon is configured not to illuminate until the detector detects a tap, or the button is pressed, or until a predetermined period of time.

9. The networked medication-delivery system of claim 1, wherein the system is configured to enable a user to acknowledge an audible, visual, or haptic alarm or alert message provided by the remote user-interface device by tapping the medication delivery device or pressing the button on the medication delivery device before the medication delivery device triggers the audible, visual, or haptic alarm or alert message via the feedback feature.

10. The networked medication-delivery system of claim 1, wherein the feedback feature comprises a vibration motor adapted to provide haptic feedback, wherein the controller is adapted to provide haptic feedback or audible feedback, upon issuing the alarm and alert communications, wherein the audible alarm or alert message triggered if the controller fails to receive an acknowledgement of the alert or alarm condition within a predetermined period of time is louder or longer in duration than the haptic feedback or audible feedback provided when the controller issues the alarm and alert communications.

11. The networked medication-delivery system of claim 1, wherein the system is configured such that an acknowledgement of an alarm or alert will quiet audible or haptic feedback for the alarm or alert condition for a predetermined snooze period of time, and wherein the controller is adapted to issue new alarm and alert communications after the predetermined snooze period of time if the alarm or alert condition is still detected as being present.

12. The networked medication-delivery system of claim 1, wherein the remote user-interface device is adapted to present the user with troubleshooting instructions using at least one of text, audio, or video to remove the alarm or alert condition, and wherein the medication delivery device is configured to not present any troubleshooting instructions using text, audio, or video.

13. The networked medication-delivery system of claim 1, wherein the medication delivery device comprises a housing configured to contain a non-rechargeable, non-replaceable battery.

14. The networked medication-delivery system of claim 1, wherein the remote user-interface device is adapted to enable a user to send instructions to the medication delivery device using the remote user-interface device, wherein the remote user-interface device is configured to prompt the user to confirm the instructions by pressing the detector or button or tapping the controller under certain conditions.

15. The networked medication-delivery system of claim 14, wherein the controller is adapted to require a user to confirm a bolus delivery by pressing the detector or button or tapping the controller if the dosage is determined by the controller to be unusual based on typical dosage amounts administered by the user, based on a timing of dosage or a timing of a previous dosage, or based on a prediction of how the dosage will change analyte levels for the user.

16. The networked medication-delivery system of claim 1, wherein the medication delivery device is configured to indicate via the icon at least one of:
    whether the dosage of the medication is being delivered based on the analyte sensor or not or whether there is an error with the analyte sensor;
    that an amount of medication in the medication delivery device is below a threshold level;
    that the user should administer more medication or consume carbohydrates; or
    that a more detailed message for the user is awaiting the user on the remote user-interface device.

17. A method for issuing alarms and alerts in a networked diabetes management system, the method comprising:
    receiving glucose sensor data from a continuous glucose monitor;
    determining a dosage of insulin delivery based at least in part on the glucose sensor data;
    detecting an alarm or alert condition;
    sending a wireless communication regarding the alarm or alert condition to a remote user-interface device;
    triggering an audible, visual, or haptic alarm or alert on at least one of an insulin delivery device or the remote user-interface device if the insulin delivery device does not receive an acknowledgement of the alarm or alert condition within a predetermined period of time; and
    triggering an audible, visual, or haptic alarm or alert on at least one of the insulin delivery device or the remote user-interface device when the insulin delivery device changes from an automation mode of operation to a programmed mode of operation.

18. The method of claim 17, further comprising receiving acknowledgement of the alarm or alert from the user when the user presses a button on the insulin delivery device or taps the insulin delivery device and interacts with the remote user-interface device, wherein the insulin delivery device receives the acknowledgement of the alarm or alert condition as part of a wireless communication from the remote user-interface device.

19. The method of claim 17, further comprising triggering audible or haptic feedback of the insulin delivery device when sending the communication regarding the alarm or alert condition to the remote user-interface device, wherein the audible, visual, or haptic alarm or alert on the insulin delivery device after the predetermined period of time is louder or longer in duration than the feedback initiated when sending the communication.

20. The method of claim 17, further comprising stopping the audible, visual, or haptic alarm or alert on the insulin delivery device when a button on the insulin delivery device is pressed.

21. The method of claim 20, further comprising requiring the button to be pressed at least twice during a predetermined period of time or according to a predetermined pattern for the audible, visual, or haptic alarm or alert to be stopped.

22. The method of claim 17, further comprising:
    preventing the triggering of an additional audible, visual, or haptic alarms or alerts or the sending of another communication after stopping the audible, visual, or haptic alarm or alert for a predetermined period of time; and
    triggering an audible, visual, or haptic alarm or alert after the predetermined period of time if the alarm or alert condition is present after the predetermined period of time.

23. The method of claim 17, further comprising triggering the alarm or alert condition when at least one of:
    an amount insulin remaining in the insulin delivery device being below a threshold level; or
    when a low glucose condition or a high glucose condition occurs.

24. The method of claim 23, wherein triggering the alarm or alert condition comprises illuminating an icon or an area next to an icon indicating that the user should eat or should administer insulin.

25. The method of claim 17, further comprising triggering the alarm or alert condition when the continuous glucose monitor is at least one of not working, not in range, or not reliable.

26. The method of claim 17, further comprising triggering the alarm or alert condition as a notice about at least one of a possible occlusion, a possible air bubble, a possible missed meal announcement, a possible need to change an infusion set, a possible need to calibrate a CGM, a possible need to replace the CGM, or a possible need to check ketone levels, wherein the audible, visual, haptic alarm or alert on the insulin delivery device includes illumination of an icon or next to an icon indicating that the user should check the remote user-interface device for information about the alert.

27. An insulin delivery device adapted for wireless communication with a continuous glucose monitor and a remote user-interface device, the insulin delivery device comprising:
    a drive system adapted to be in communication with an insulin reservoir and to meter administration of insulin out of the insulin delivery device;
    a wireless transmitter and receiver adapted to send and receive wireless communications from at least a continuous glucose monitor and a remote user-interface device;
    a controller adapted to change a dosage of medication based at least in part on data from the continuous glucose monitor and adapted to issue alarm and alert wireless communications based on a detection of an alarm or alert condition;

a housing containing at least the controller and the wireless transmitter and receiver;

a tap detector within the housing or a button on the housing adapted to permit the user to check a status of the insulin delivery device or to acknowledge alert or alarm conditions; and one or more lights adapted to illuminate icons or adjacent to icons on the housing indicating that a message related to insulin delivery is waiting at the remote user-interface device.

28. The device of claim 27, wherein the one or more lights are adapted to illuminate the icons or adjacent to the icons on the housing indicating that there is a problem with data being received, or a lack of data being received, from the continuous glucose monitor.

29. A medication delivery system comprising a medication delivery device and a remote user-interface device, the medication delivery device and the remote user-interface device being in wireless communication, the medication delivery device being adapted to automatically administer medication based on analyte sensor data without user input, the remote user-interface device being adapted to receive user commands for the medication delivery device to administer additional doses of medication, adjust programmed delivery rate or schedule, or adjust an algorithm that determines a dosage based on the analyte sensor data, wherein both the remote user-interface device and the medication delivery device are adapted to provide audible, visual, or haptic feedback to issue an alarm or alert regarding an ability of the medication delivery device to deliver medication, wherein the medication delivery device is adapted to detect a condition that prevents the delivery of medication and is adapted to send an alarm wireless communication to the remote user-interface device regarding the condition, wherein the remote user-interface device issues an audible, visual, or haptic alarm when the alarm wireless communication is received and provides a feedback feature for the user to acknowledge the alarm or alert, wherein the remote user-interface device is configured to send an acknowledgement wireless communication to the medication delivery device upon the user acknowledging the alarm or alert, wherein the medication delivery device is adapted to issue an audible, visual, or haptic alarm after a predetermined period of time after the alarm wireless communication is sent unless the medication delivery device receives the acknowledgement wireless communication during the predetermined period of time.

30. The medication delivery system of claim 29, wherein the medication delivery device is an insulin infusion pump, wherein the medication is insulin, and wherein the remote user-interface device is a smartphone.

31. The medication delivery system of claim 30, further comprising a continuous glucose monitor in wireless communication with the insulin infusion pump, wherein the insulin infusion pump is configured to deliver different amounts or rates of insulin based on glucose data from the continuous glucose monitor.

32. The medication delivery system of claim 31, wherein the insulin infusion pump is not adapted to display specific concentrations of the glucose data, but is adapted to send glucose data wireless communications to the smartphone, wherein the smartphone is adapted to display specific concentrations of glucose data.

33. The medication delivery system of claim 32, wherein the insulin infusion pump is adapted to illuminate one or more icons, or a light next to one or more icons, the one or more icons and the light configured to indicate that the user is in or expected to experience hypoglycemic state or a hyperglycemic state, to indicate that the user should administer more insulin, or to indicate that the user should consume food, wherein the light becomes illuminated when the insulin infusion pump issues an issue an audible, visual, or haptic alarm or when the user acknowledges the alarm on the insulin infusion pump.

* * * * *

UNITED STATES PATENT AND TRADEMARK OFFICE
CERTIFICATE OF CORRECTION

PATENT NO. : 11,096,624 B2  
APPLICATION NO. : 16/335163  
DATED : August 24, 2021  
INVENTOR(S) : Bryan Mazlish et al.

Page 1 of 1

It is certified that error appears in the above-identified patent and that said Letters Patent is hereby corrected as shown below:

In the Specification

| | | |
|---|---|---|
| Column 1, | Line 57, | change "DISCLOSURE" to --BRIEF SUMMARY-- |
| Column 2, | Line 53, | change "((e.g.," to --(e.g.,-- |
| Column 2, | Line 63, | change "(e.g.," to --((e.g.,-- |
| Column 13, | Lines 56-57, | change "MODE(S) FOR CARRYING OUT THE INVENTION" to --DETAILED DESCRIPTION-- |

Signed and Sealed this  
Nineteenth Day of October, 2021

Drew Hirshfeld  
*Performing the Functions and Duties of the*  
*Under Secretary of Commerce for Intellectual Property and*  
*Director of the United States Patent and Trademark Office*